(12) United States Patent
Cooper et al.

(10) Patent No.: US 11,459,296 B2
(45) Date of Patent: Oct. 4, 2022

(54) ANTIBACTERIAL COMPOUNDS

(71) Applicant: INFEX Therapeutics Limited, Macclesfield (GB)

(72) Inventors: Ian Cooper, Macclesfield (GB); David Orr, Macclesfield (GB); Andrew Wilkinson, Macclesfield (GB); Jonathan Finlayson, Macclesfield (GB); Adam Bunt, Macclesfield (GB); Pia Appelqvist, Trosa (SE); Hans Wallberg, Huddinge (SE); Fredrik Wångsell, Mölndal (SE)

(73) Assignee: INFEX Therapeutics Limited, Macclesfield (GB)

( * ) Notice: Subject to any disclaimer, the term of this patent is extended or adjusted under 35 U.S.C. 154(b) by 0 days.

(21) Appl. No.: 17/055,506

(22) PCT Filed: May 16, 2019

(86) PCT No.: PCT/GB2019/051349
§ 371 (c)(1),
(2) Date: Nov. 13, 2020

(87) PCT Pub. No.: WO2019/220125
PCT Pub. Date: Nov. 21, 2019

(65) Prior Publication Data
US 2021/0230115 A1 Jul. 29, 2021

(30) Foreign Application Priority Data

May 16, 2018 (GB) .................................. 1807966
Apr. 11, 2019 (GB) .................................. 1905174

(51) Int. Cl.
| | | |
|---|---|---|
| C07D 401/04 | (2006.01) |
| C07D 401/10 | (2006.01) |
| C07D 401/12 | (2006.01) |
| C07D 401/14 | (2006.01) |
| C07D 207/48 | (2006.01) |
| C07D 403/04 | (2006.01) |
| C07D 403/12 | (2006.01) |
| C07D 403/14 | (2006.01) |
| C07D 487/04 | (2006.01) |
| C07D 417/04 | (2006.01) |
| A61P 31/04 | (2006.01) |
| C07D 207/36 | (2006.01) |

(52) U.S. Cl.
CPC ............ *C07D 207/48* (2013.01); *A61P 31/04* (2018.01); *C07D 207/36* (2013.01); *C07D 401/04* (2013.01); *C07D 401/10* (2013.01); *C07D 401/12* (2013.01); *C07D 401/14* (2013.01); *C07D 403/04* (2013.01); *C07D 403/12* (2013.01); *C07D 403/14* (2013.01); *C07D 417/04* (2013.01); *C07D 487/04* (2013.01)

(58) Field of Classification Search
CPC .. C07D 401/04; C07D 401/10; C07D 401/12; C07D 401/14; C07D 207/48; C07D 403/04; C07D 403/12; C07D 403/14; C07D 487/04; C07D 417/04; A61P 31/04
See application file for complete search history.

(56) References Cited

FOREIGN PATENT DOCUMENTS

| | | |
|---|---|---|
| CN | 105452220 A | 3/2016 |
| WO | WO-2014/184350 A1 | 11/2014 |
| WO | WO-2014/198849 A1 | 12/2014 |
| WO | WO-2015/112441 A1 | 7/2015 |
| WO | WO-2016/187521 A1 | 11/2016 |
| WO | WO-2018/015445 A1 | 1/2018 |
| WO | WO-2018/215799 A1 | 11/2018 |

OTHER PUBLICATIONS

Biedenbach et al., "Dissemination of NDM Metallo-β-Lactamase Genes among Clinical Isolates of Enterobacteriaceae Collected during the SMART Global Surveillance Study from 2008 to 2012," Antimicrobial Agents and Chemotherapy, 59(2): 826-830 (2015).
Elbrolosy et al., "New Delhi metallo-β-lactamase-producing Acinetobacter isolates among late-onset VAR patients: multidrug-resistant pathogen and poor outcome," Infection and Drug Resistance, 12: 373-384 (2019).

(Continued)

*Primary Examiner* — Laura L Stockton
(74) *Attorney, Agent, or Firm* — Foley Hoag LLP; Dana M. Gordon

(57) ABSTRACT

This invention relates to compounds of formula (I) and methods of treatment using the compounds. The compounds of the invention can be used in combination with antibacterial agents to treat bacterial infections. More specifically, the compounds of formula (I) can be used in combination with a class of antibacterial agents known as carbapenems. The novel compounds of the present invention are enzyme inhibitors and more particularly are metallo-β-lactamase inhibitors.

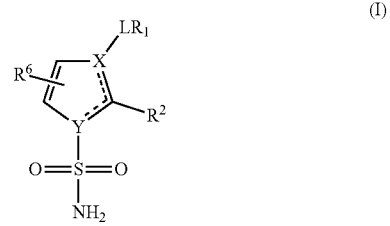

(I)

18 Claims, No Drawings

(56) References Cited

OTHER PUBLICATIONS

Falcone et al., "Infections with VIM-1 Metallo-β-Lactamase-Producing Enterobacter cloacae and Their Correlation with Clinical Outcome," Journal of Clinical Microbiology, 47(11): 3514-3519 (2009).
International Search Report and Written Opinion for International Application No. PCT/GB2019/051349 dated Jun. 26, 2019.
Sanctis et al., "Complex prosthetic joint infections due to carbapenemase-producing Klebsiella pneumoniae: a unique challenge in the era of untreatable infections," International Journal of Infectious Diseases, 25: 73-78 (2014).
Search and Examination Report for GB Application No. 1807966.5 dated Dec. 18, 2018.
CA Office Action for Indian Patent Application No. 202047046476 dated Jun. 6, 2022.

ical intermediate. MBLs coordinate water molecules and zinc ions to His, Cys and Asp residues in their active site, where water molecules facilitate nucleophilic attack and bond cleavage within the β-lactam ring. The subclasses of MBLs are structurally divergent, with B1 and B3 enzymes containing two zinc ions in the active site and displaying a broad substrate profile. Group B2 enzymes rely upon a single zinc ion and hydrolyse only carbapenems. Clinically, MBLs of the B1 class, including NDM, VIM and IMP, are most prevalent and are frequently identified within mobile genetic elements.

ANTIBACTERIAL COMPOUNDS

RELATED APPLICATIONS

This application is the U.S. national phase of International Patent Application No. PCT/GB2019/051349, filed May 16, 2019; which claims the benefit of priority of United Kingdom Patent Application Nos. GB 1807966.5 filed May 16, 2018; and GB 1905174.7 filed Apr. 11, 2019.

INTRODUCTION

This invention relates to compounds that can be used to treat bacterial infections in combination with other antibacterial agents, and more specifically in combination with a class of antibacterial agents known as carbapenems. The novel compounds of the present invention are enzyme inhibitors and more particularly are metallo-β-lactamase inhibitors.

Each year, throughout Europe, over 4 million people contract a healthcare associated bacterial infection, resulting in ~37,000 deaths (Public Health England). The increasing prevalence of multi-drug resistant bacteria has worsened patient outcomes, prolonged hospital stays and necessitated use of 'last resort' and potentially toxic antimicrobials, such as colistin and polymyxin B. It has been estimated that by 2050, without intervention, antibiotic-resistant bacteria will cause the death of over 10 million people each year, and this will equate to an economic burden of 100 trillion US dollars.

In the clinic, antibiotic-resistant Gram-negative pathogens cause diverse infections, including pneumonia, blood stream infections, surgical site infections, skin and soft tissue infections, and urinary tract infections. There are limited effective treatment options for these organisms and empirical antibiotic therapy often fails in patients infected with Gram-negative organisms of the ESKAPE pathogen group (*Enterococcus faecium, Staphylococcus aureus, Klebsiella pneumoniae, Acinetobacter baumannii, Pseudomonas aeruginosa,* and *Enterobacter* species).

In February 2017, the World Health Organisation (WHO) issued a prioritised list of bacterial pathogens to assist member states in focusing research and development to the areas of greatest need. Of these bacteria, the WHO classed the following Gram-negative organisms as a critical priority: carbapenem resistant *A. baumannii*; carbapenem resistant *P. aeruginosa*; carbapenem resistant and ESBL-producing Enterobacteriaceae (including *K. pneumoniae* and *E. coli*). Consequently, carbapenem-resistant Gram-negative bacteria have been defined as a critical unmet medical need. The mode of action of β-lactams, such as carbapenems, involves covalently binding to the active site of transpeptidases that link peptidoglycan chains of the bacterial cell wall. This results in inhibition of cell wall synthesis and ultimately cell death. The advantage of carbapenems is a broader spectrum of activity compared with most other β-lactams and until recently their use had not been significantly impacted by resistance development.

The use of carbapenems as a last line of defense against multi-drug resistant Gram-negatives has been compromised by the emergence of carbapenemases from the metallo-β-lactamase (MBL) class. These enzymes bind to carbapenems and cleave the β-lactam ring, resulting in antibiotic deactivation. The Ambler classification system divides known β-lactamase enzymes into four classes according to amino acid sequence. Classes A, C and D β-lactamases cleave β-lactams through transient binding of a serine group within the enzyme's active site to the carbonyl of the β-lactam ring. This results in formation of an acyl-enzyme and cleavage of the β-lactam ring. Subsequently, an activated water molecule deacylates the acyl-enzyme intermediate, hydrolysing the bond between serine and carbonyl, releasing the deactivated β-lactam. MBLs are mechanistically and structurally discrete from class A, C and D serine-β-lactamases. In this case, cleavage of β-lactams occurs in a single step, without formation of a covalent intermediate. MBLs coordinate water molecules and zinc ions to His, Cys and Asp residues in their active site, where water molecules facilitate nucleophilic attack and bond cleavage within the β-lactam ring. The subclasses of MBLs are structurally divergent, with B1 and B3 enzymes containing two zinc ions in the active site and displaying a broad substrate profile. Group B2 enzymes rely upon a single zinc ion and hydrolyse only carbapenems. Clinically, MBLs of the B1 class, including NDM, VIM and IMP, are most prevalent and are frequently identified within mobile genetic elements.

Pre-existing serine-β-lactamase inhibitors (effective against Ambler Class A, C and some Class D β-lactamases) have successfully restored activity of numerous β-lactams. Inhibitors bind to the active site of the enzyme transiently or permanently with high affinity, effectively outcompeting binding of β-lactams. Marketed β-lactam/β-lactamase inhibitor combinations include amoxicillin and clavulanic acid (Co-amoxiclav) and ceftazidime and avibactam (Avycaz). Currently, there are no metallo-β-lactamase inhibitors (MBLIs) in clinical development or clinically available, indicating commercial potential for a broad spectrum MBLI that restores the activity of carbapenems.

The first carbapenem used clinically was imipenem, for the treatment of complex microbial infections. A disadvantage of imipenem is its hydrolysis in the mammalian kidney by dehydropeptidase I (DHPI) necessitating co-formulation with the dehydropeptidase inhibitor cilastatin. Subsequent carbapenem iterations, including meropenem, are insusceptible to DHPI hydrolysis due to the presence of a methyl group at the 1-β position of the carbapenem moiety. Meropenem is less potent than imipenem against Gram-positive pathogens but has enhanced potency against Gram-negative organisms and is employed widely in the clinic. To combat resistance to carbapenems, we have discovered a series of compounds that inhibit metallo-β-lactamase enzymes. The compounds significantly improve the efficacy of meropenem against drug resistant bacteria when co-administered with meropenem. The invention relates specifically to these compounds and to combinations of these compounds with a carbapenem such as meropenem. The invention also relates to methods of using said compounds and to pharmaceutical formulations comprising said compounds.

It is contemplated that other approved carbapenems might also benefit from co-formulation with the compounds of the invention. Other currently approved carbapenems include: ertapenem, doripenem, panipenem, biapenem and tebipenem.

BACKGROUND

Until comparatively recently, bacterial infections were one of the most common causes of death, disfigurement and disablement. During the 19$^{th}$ century a series of antibiotic drug classes were developed, meaning that the successful treatment of bacterial infections has become routine. However, microbial resistance to antibiotics is becoming a significant problem and many consider that this will become one of the most significant challenges to human health.

Indeed, in some bacterial pathogens, multidrug resistance has already become common.

The greatest unmet medical need is the dearth of effective treatments for multidrug resistant Gram-negative bacteria. Therefore discovery of novel antibiotics that are active against WHO listed pathogens of critical concern, or drugs that circumvent existing bacterial resistance mechanisms is essential.

WO2015/112441 discloses a series of novel metallo-β-lactamase inhibitors and their uses which are intended for reducing bacterial β-lactam antibiotic resistance. The compounds are a series of substituted 1H and 2H-tetrazol-5-yl phenylsulphonamides.

US2016/0272601 also discloses a series of novel compounds and their use as metallo-β-lactamase inhibitors for use in combination with β-lactam antibiotics. The compounds of this disclosure are thiazole-4-carboxylic acid derivatives.

WO2017/093727 discloses another series of compounds which are inhibitors of metallo-β-lactamases and may be used in the treatment of bacterial infections. The exemplified compounds of this disclosure are a series of substituted 1H-indoles.

It is an aim of certain embodiments of this invention to provide compounds which can prevent or slow unwanted metabolism of β-lactams such as carbapenems, and in particular meropenem. A further aim is to provide formulations of a carbapenem, for example meropenem, with a compound of the invention which is active against Gram-negative bacteria including antibiotic-resistant organisms. It is an aim of certain embodiments of this invention to provide compounds that can be included in the formulations which are active against bacterial strains that are resistant to one or more other antibiotics. In spite of the numerous different antibiotics known in the art for a variety of different infections, there continues to be a need to develop antibiotics that can provide effective treatment in a reliable manner. In addition, there remains a need for drugs which can avoid or reduce the side-effects associated with known antibiotics. A further aim of certain embodiments is to provide treatment which is effective in a selective manner at a chosen site of interest. Another aim of certain embodiments is to develop drugs with a suitable pharmacokinetic profile and duration of action following dosing.

The present invention seeks to overcome the disadvantages of known carbapenems. The present invention also aims to improve the efficacy of existing carbapenems such as meropenem. In certain embodiments, the present invention aims to provide a compound that can restore or prolong the activity of antibiotics (particularly carbapenems) against antibiotic resistant bacterial strains. It is also an aim of certain embodiments of the present invention to increase the antibiotic efficacy of an antibiotic against bacterial strains having a wide spectrum of metallo-β-lactamase enzymes, for example some or all of VIM, NDM, and IMP.

It is an aim of certain embodiments of this invention to provide new antibiotic formulations which are active against resistant strains of Gram-negative bacteria. A further aim of certain embodiments of the present invention is to provide antibiotic formulations in which the metabolised fragment or fragments of the drug after absorption are GRAS (Generally Regarded As Safe). A further aim of the invention is to provide prodrugs which are not species dependent and/or which reduce inter-patient variability due to differences in metabolism. Another aim of the invention is to provide prodrugs which are able to overcome the food effect in the sense that they can be administered to fed or fasted patients without the need to control carefully the dosing schedule relative to meal times.

The novel compounds of the present invention satisfy some or all of the above aims.

DETAILED DESCRIPTION OF THE INVENTION

In a first aspect, the invention provides a compound of formula (I), or pharmaceutically acceptable salts thereof:

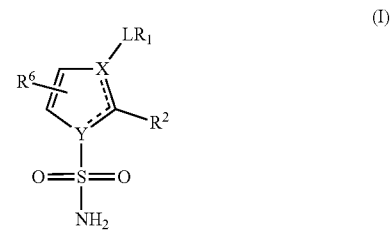

wherein
one of X and Y is N and the other is C;
L is a linker group selected from —$(CH_2)_a$-Q-$(CH_2)_b$— in which, Q is selected from the group comprising: O, NH, $SO_2$, C=C, and C≡C or Q is absent;
$R^1$ is selected from a ring:

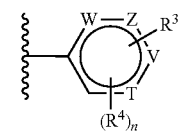

in which: (a) all of T, V, W and Z are C, or (b) T is C and one or two of V, W and Z is N and the remainder of them is/are C, or (c) T is absent, and one of V, W and Z is C and the other two are N; or $R^1$ is a mono- or bi-cyclic ring substituted by one $R^3$ group and 0, 1, or 2 $R^4$ groups;
$R^2$ is —C(O)OH, —C(O)OM or

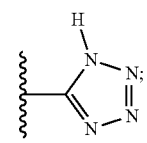

wherein M is a group 1 cation;
$R^3$ is either absent or is selected as appropriate to satisfy valence requirements from the group comprising: H, halo, CN, oxo, $C_{1-6}$ alkyl, $C_{1-6}$ alkoxy, $C_{2-6}$ alkenyl, $C_{2-6}$ alkynyl, $C_{3-8}$ cycloalkyl, —$(CH_2)_d$-aryl, —$(CH_2)_d$-heteroaryl, —$(CH_2)_e$-heterocyclyl, —$OR^5$, —$N(R^5)_2$, —$SO_2R^5$, —$SO_2N(R^5)_2$, —$NHSO_2R^7$, —$NHCOR^5$, —$CON(R^5)_2$ and —$COR^5$ wherein each of the above substituents apart from H may themselves be optionally substituted where chemically possible with one, two or three groups independently selected at each occurrence from the group comprising: halo, —$N(R^5)_2$, —OH, —C(=O)$C_{1-6}$ alkyl, —$SO_2N(C_{1-6}$ alkyl$)_2$, —$(CH_2)_nOR^5$, $C_{1-6}$ alkyl, $C_{2-6}$ alkenyl, $C_{2-6}$ alkynyl, $C_{3-8}$ cycloalkyl, and $C_{3-8}$ cycloalkenyl;

$R^4$ and $R^5$ are independently selected at each occurrence from the group comprising: H, halo, —OH, $C_{1-6}$ alkyl, $C_{1-6}$ haloalkyl, $C_{2-6}$ alkenyl, $C_{2-6}$ alkynyl, $C_{3-8}$ cycloalkyl, $C_{3-8}$ cycloalkenyl, —$(CH_2)_f$-aryl, —$(CH_2)_d$-heteroaryl, —$(CH_2)_g$-heterocyclyl; wherein each of $R^4$ and $R^5$ may themselves be optionally substituted where chemically possible with one, two or three groups independently selected at each occurrence from the group comprising: halo, —$NH_2$, —$N(C_{1-4}alkyl)_2$, —OH, —$SO_2N(C_{1-4}alkyl)_2$, —NHC(=O)O$C_{1-6}$ alkyl and —C(=O)O$C_{1-6}$ alkyl;

$R^6$ is selected from the group comprising: H, $C_{1-4}$alkyl, and $C_{1-4}$ haloalkyl;

$R^7$ is selected from the group comprising: H, $C_{1-4}$ alkyl, $C_{1-4}$ haloalkyl, $C_{1-4}$ alkyl amine, $C_{3-8}$ cycloalkyl and aryl, and 5 to 10 membered heteroaryl;

a, b, d, e, f, g and h are independently selected as integers from 0 to 3;

and n is an integer selected from 0 to 2; and

--- represents a single or a double bond as required to satisfy valence requirements.

In embodiments, the invention provides a compound of formula (I), or pharmaceutically acceptable salts thereof:

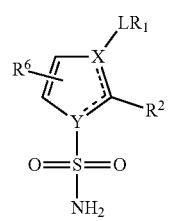

(I)

wherein
one of X and Y is N and the other is C;
L is a linker group selected from —$(CH_2)_a$-Q-$(CH_2)_b$— in which, Q is selected from the group comprising: O, NH, $SO_2$, C=C, and C≡C or Q is absent;
$R^1$ is selected from a ring:

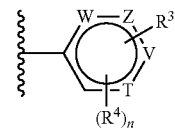

in which: (a) all of T, V, W and Z are C, or (b) T is C and one or two of V, W and Z is N and the remainder of them is/are C, or (c) T is absent, and one of V, W and Z is C and the other two are N; or $R^1$ is a mono- or bi-cyclic ring substituted by one $R^3$ group and 0, 1, or 2 $R^4$ groups;

$R^2$ is —C(O)OH, —C(O)OM or

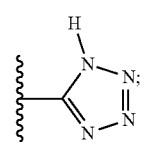

wherein M is a group 1 cation;

$R^3$ is either absent or is selected as appropriate to satisfy valence requirements from the group comprising: H, halo, CN, oxo, $C_{1-6}$ alkyl, $C_{1-6}$ alkoxy, $C_{2-6}$ alkenyl, $C_{2-6}$ alkynyl, $C_{3-8}$ cycloalkyl, —$(CH_2)_d$-aryl, —$(CH_2)_d$-heteroaryl, —$(CH_2)_e$-heterocyclyl, —$OR^5$, —$N(R^5)_2$, —$SO_2R^5$, —$SO_2N(R^5)_2$, —$NHSO_2R^7$, —$NHCOR^5$, —$CON(R^5)_2$ and —$COR^5$ wherein each of the above substituents apart from H may themselves be optionally substituted where chemically possible with one, two or three groups independently selected at each occurrence from the group comprising: halo, —$N(R^5)_2$, —OH, —C(=O)$C_{1-6}$ alkyl, —$SO_2N(C_{1-6}$ alkyl$)_2$, $C_{1-6}$ alkyl, $C_{2-6}$ alkenyl, $C_{2-6}$ alkynyl, $C_{3-8}$ cycloalkyl, and $C_{3-8}$ cycloalkenyl;

$R^4$ and $R^5$ are independently selected at each occurrence from the group comprising: H, halo, $C_{1-6}$ alkyl, $C_{2-6}$ alkenyl, $C_{2-6}$ alkynyl, $C_{3-8}$ cycloalkyl, $C_{3-8}$ cycloalkenyl, —$(CH_2)_f$-aryl, —$(CH_2)_d$-heteroaryl, —$(CH_2)_g$-heterocyclyl; wherein each of $R^4$ and $R^5$ may themselves be optionally substituted where chemically possible with one, two or three groups independently selected at each occurrence from the group comprising: halo, —$NH_2$, —$N(C_{1-4}$ alkyl$)_2$, —OH, —$SO_2N(C_{1-4}$ alkyl$)_2$, and —C(=O)O$C_{1-6}$ alkyl;

$R^6$ is selected from the group comprising: H, $C_{1-4}$alkyl, and $C_{1-4}$ haloalkyl;

$R^7$ is selected from the group comprising: H, $C_{1-4}$ alkyl, $C_{1-4}$ haloalkyl, $C_{3-8}$ cycloalkyl and aryl, and 5 to 10 membered heteroaryl;

a, b, d, e, f and g are independently selected as integers from 0 to 3;

and n is an integer selected from 0 to 2; and

--- represents a single or a double bond as required to satisfy valence requirements.

In embodiments, the invention provides a compound of formula (I):

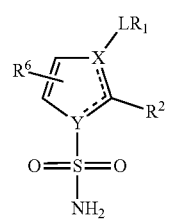

(I)

wherein
one of X and Y is N and the other is C;
L is a linker group selected from —$(CH_2)_a$-Q-$(CH_2)_b$— in which, Q is selected from the group comprising: O, NH, $SO_2$, C=C, and C≡C or Q is absent;
$R^1$ is selected from a ring:

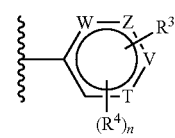

in which: (a) all of T, V, W and Z are C, or (b) T is C and one or two of V, W and Z is N and the remainder of them is/are C, or (c) T is absent, and one of V, W and Z is C and the other two are N; or $R^1$ is a mono- or bi-cyclic ring substituted by one $R^3$ group and 0, 1, or 2 $R^4$ groups;

$R^2$ is —C(O)OH, or

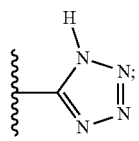

$R^3$ is either absent or is selected as appropriate to satisfy valence requirements from the group comprising: H, halo, CN, oxo, $C_{1-6}$ alkyl, $C_{1-6}$ alkoxy, $C_{2-6}$ alkenyl, $C_{2-6}$ alkynyl, $C_{3-8}$ cycloalkyl, —$(CH_2)_d$-aryl, —$(CH_2)_d$-heteroaryl, —$(CH_2)_e$-heterocyclyl, —$N(R^5)_2$, —$SO_2R^5$, —$SO_2N(R^5)_2$, —$NHSO_2R^5$, —$NHCOR^5$, —$CON(R^5)_2$ wherein each of the above substituents apart from H may themselves be optionally substituted where chemically possible with one, two or three groups independently selected at each occurrence from the group comprising: halo, —$N(R^5)_2$, —OH, $C_{1-6}$ alkyl, $C_{2-6}$ alkenyl, $C_{2-6}$ alkynyl, $C_{3-8}$ cycloalkyl, and $C_{3-8}$ cycloalkenyl;

$R^4$ and $R^5$ are independently selected at each occurrence from the group comprising: H, $C_{1-6}$ alkyl, $C_{2-6}$ alkenyl, $C_{2-6}$ alkynyl, $C_{3-8}$ cycloalkyl, $C_{3-8}$ cycloalkenyl, —$(CH_2)_f$-aryl, —$(CH_2)_d$-heteroaryl, —$(CH_2)_g$-heterocyclyl; wherein each of $R^4$ and $R^5$ may themselves be optionally substituted where chemically possible with one, two or three groups independently selected at each occurrence from the group comprising: halo, —$N(C_{1-4}$ alkyl$)_2$, —OH, and —$SO_2N(C_{1-4}$ alkyl$)_2$;

$R^6$ is selected from the group comprising: H, $C_{1-4}$alkyl, and $C_{1-4}$ haloalkyl;

$R^7$ is selected from the group comprising: H, $C_{1-4}$alkyl, $C_{1-4}$ haloalkyl and aryl;

a, b, d, e, f and g are independently selected as integers from 0 to 3;

and n is an integer selected from 0 to 2; and

--- represents a single or a double bond as required to satisfy valence requirements.

In an embodiment, the compound of Formula (I) is a compound of Formula (II):

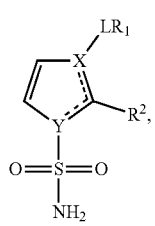

(II)

in which the previous definitions of Formula (I) apply.

In an embodiment, the compound of Formula (I) may be a compound of Formula (III):

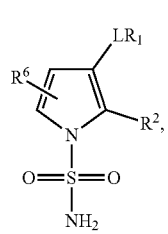

(III)

in which the previous definitions of Formula (I) apply.

In an embodiment, the compound of Formula (III) may be a compound of Formula (IV):

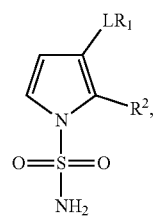

(IV)

in which the previous definitions of Formula (I) apply.

In an embodiment, the compound of Formula (I) may be a compound of Formula (V):

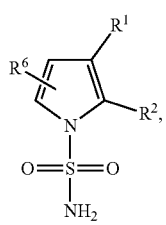

(V)

in which the previous definitions of Formula (I) apply.

In an embodiment, the compound of Formula (I) may be a compound of Formula (VI):

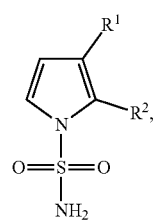

(VI)

in which the previous definitions of Formula (I) apply.

Hence, in an embodiment, Y is N and X is C.

In an alternate embodiment, Y is C and X is N.

In an embodiment, $R^1$ is a 3 to 10 membered mono- or bi-cyclic ring. In an embodiment, $R^1$ is a mono- or bi-cyclic ring (optionally a 3 to 10 membered mono- or bi-cyclic ring substituted by one $R^3$ group and 0, 1, or 2 $R^4$ groups. $R^1$ may be a carbocyclic or heterocyclic mono- or bi-cyclic ring. The $R^3$ group and the or each $R^4$ groups, when present, are substituted on ring atoms in the mono-cyclic or bi-cyclic ring system where valence considerations allow. As would be appreciated by the skilled person, the bi-cyclic ring may be a fused ring system. Preferred fused ring systems are [6,5] and [6,6] fused ring systems. These may be aromatic, partially saturated or fully saturated. Preferred mono-cyclic rings systems contain 5 or 6 ring atoms.

Accordingly, $R^1$ may be an aromatic, partially saturated or fully saturated ring system wherein the ring system is selected from: a [6,5] fused ring system; a [6,6] fused ring system; a 3 membered ring; a 4 membered ring; a 5 membered ring or a 6 membered ring.

Accordingly, $R^1$ may be an aromatic, partially saturated or fully saturated ring system wherein the ring system is selected from: a [6,5] fused ring system; a [6,6] fused ring system; a 5 membered ring or a 6 membered ring. Furthermore, accordingly, $R^1$ may be an aromatic, partially saturated or fully saturated ring system wherein the ring system is selected from: a [6,5] carbocyclic or heterocyclic fused ring system; a [6,6] carbocyclic or heterocyclic fused ring system; a 3 membered carbocyclic ring; a 4 membered carbocyclic or heterocyclic ring; a 5 membered carbocyclic or heterocyclic ring or a 6 membered ring.

When $R^1$ is a 6-membered ring, the $R^3$ substituent, when present, is preferably para with respect to its point of attachment in the compound of Formula (I).

In an embodiment, $R^1$ is an aromatic ring system. In one embodiment, $R^1$ is a fused bicyclic aromatic ring system. $R^1$ may also be a monocyclic aromatic ring system. The aromatic ring system may be carbocyclic or heterocyclic. In certain cases, a fused bicyclic ring is partially aromatic in the sense that only one of the two rings is aromatic. In some embodiments, $R^1$ is a fused bicyclic ring system which is partially aromatic.

$R^1$ may be a 5-membered heteroaryl, a 6-membered heteroaryl, a 6-membered aryl, a 10-membered heteroaryl, a 6-membered cycloalkyl, a 6-membered heterocycloalkenyl, a 6-membered heterocycloalkyl, a 5-membered cycloalkyl, a 3-membered cycloalkyl, or a 4-membered heterocycloalkyl.

Substituted or unsubstituted quinolines, isoquinolines, tetrahydroquinolines, and tetrahydroisoquinolines are examples of such rings.

In some cases, a bicyclic ring system may comprise two rings joined together via a single bond.

In some embodiments, $R^1$ is selected from:

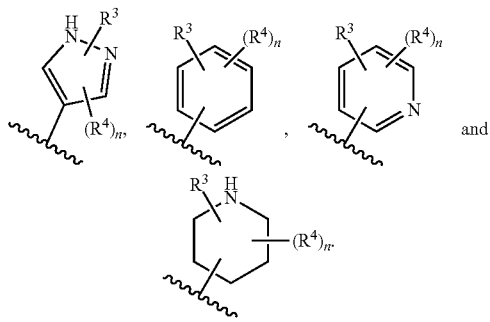

In some embodiments, $R^1$ is selected from:

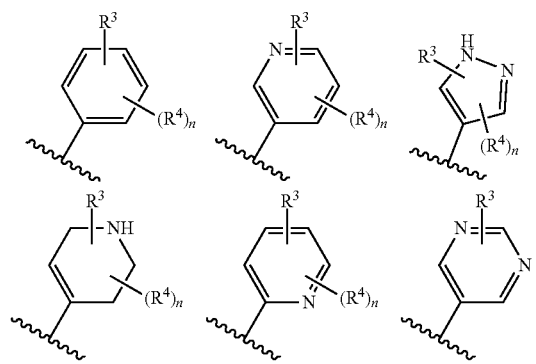

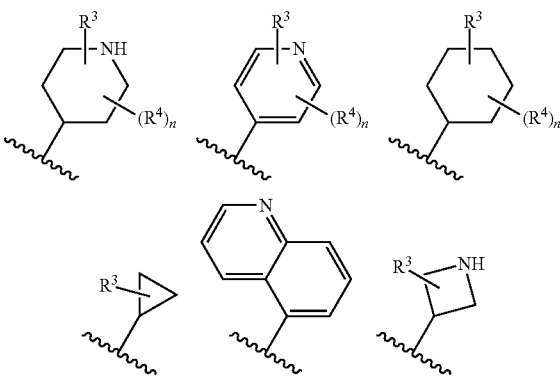

In some embodiments, $R^1$ is selected from:

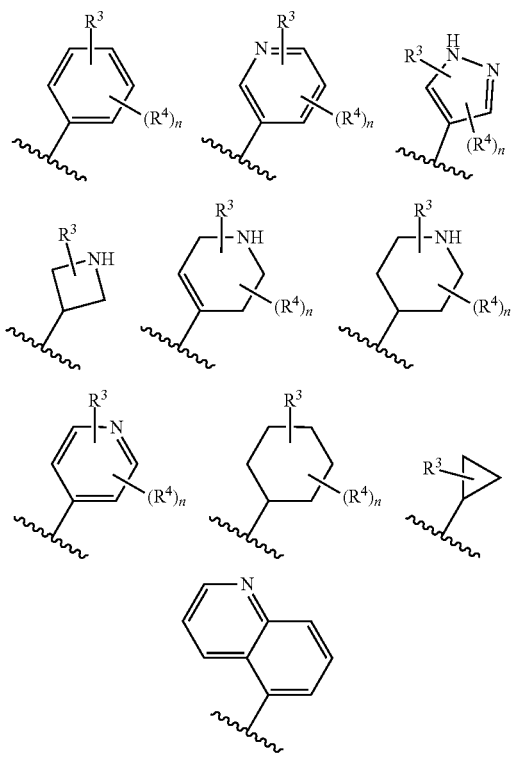

In some embodiments, $R^1$ is aryl, and is preferably substituted or unsubstituted phenyl.

$R^1$ may be selected from: phenyl, pyridine, pyrazole, cyclohexyl, quinoline, tetrahydropyridine, pyridinone, cyclopentyl, piperidine, pyrimidine, and azetidinyl.

In some embodiments, $R^1$ is selected from:

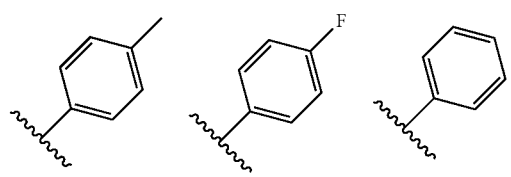

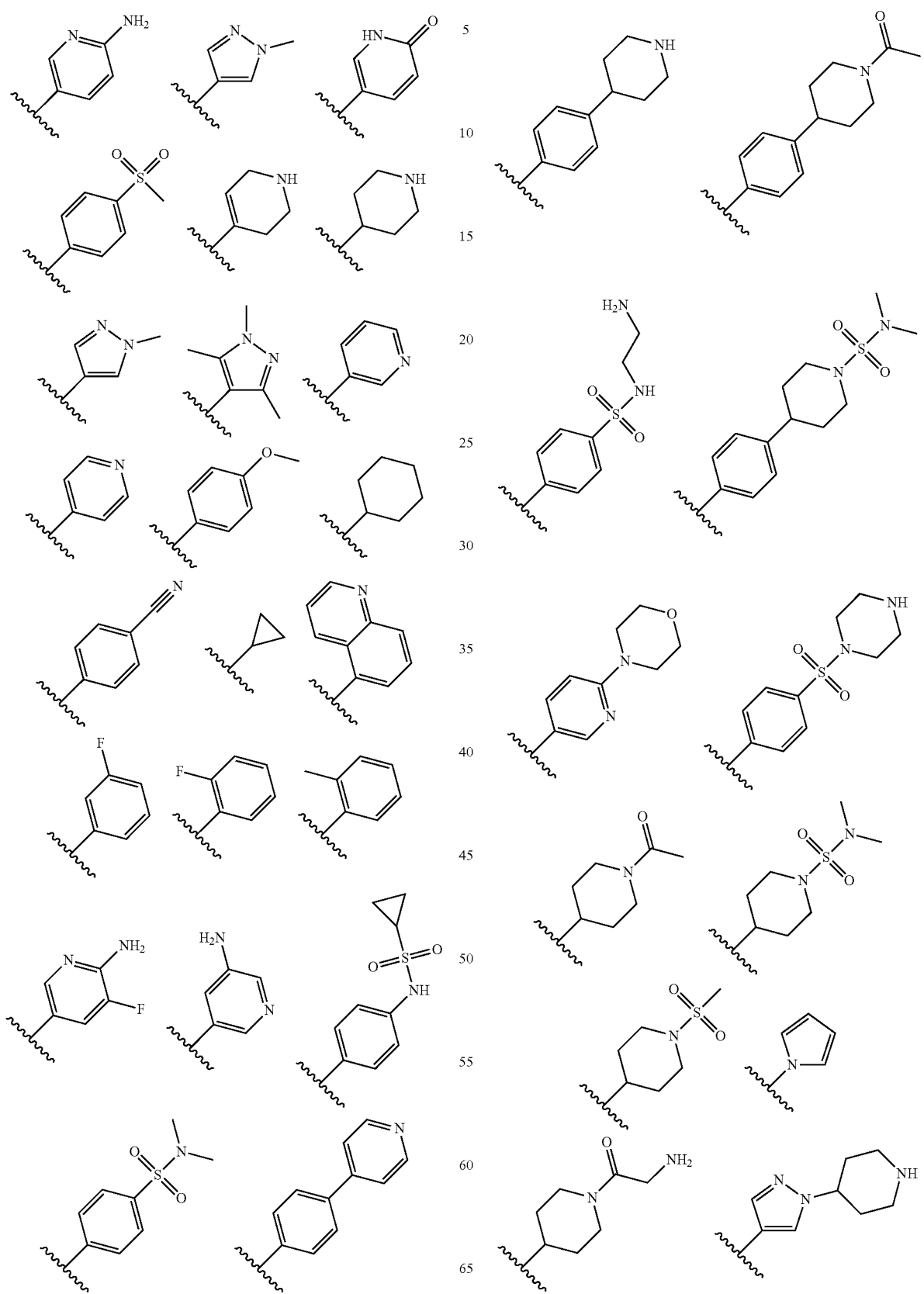

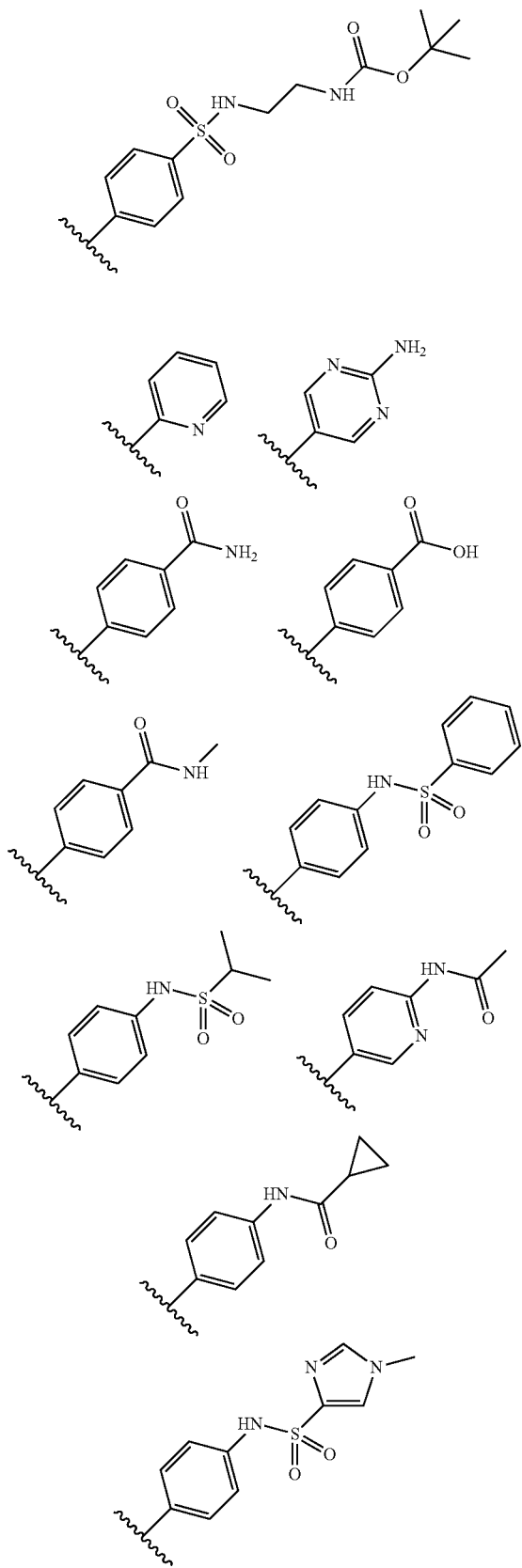
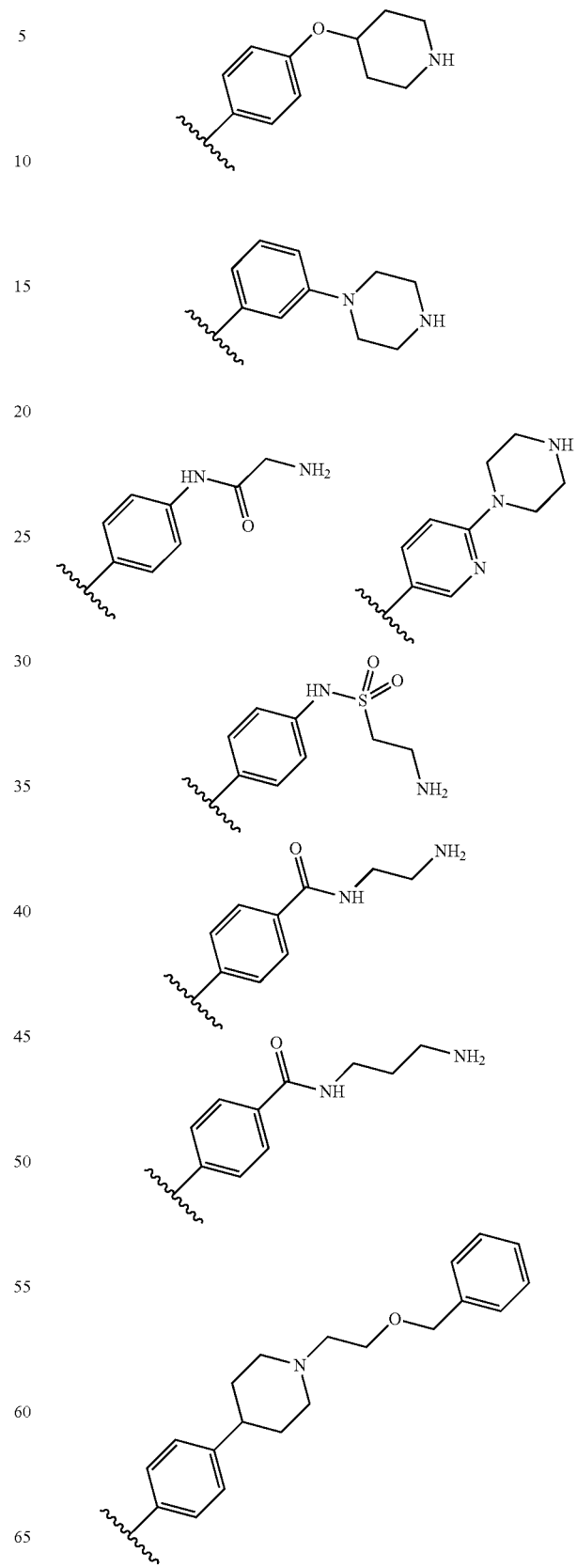

-continued

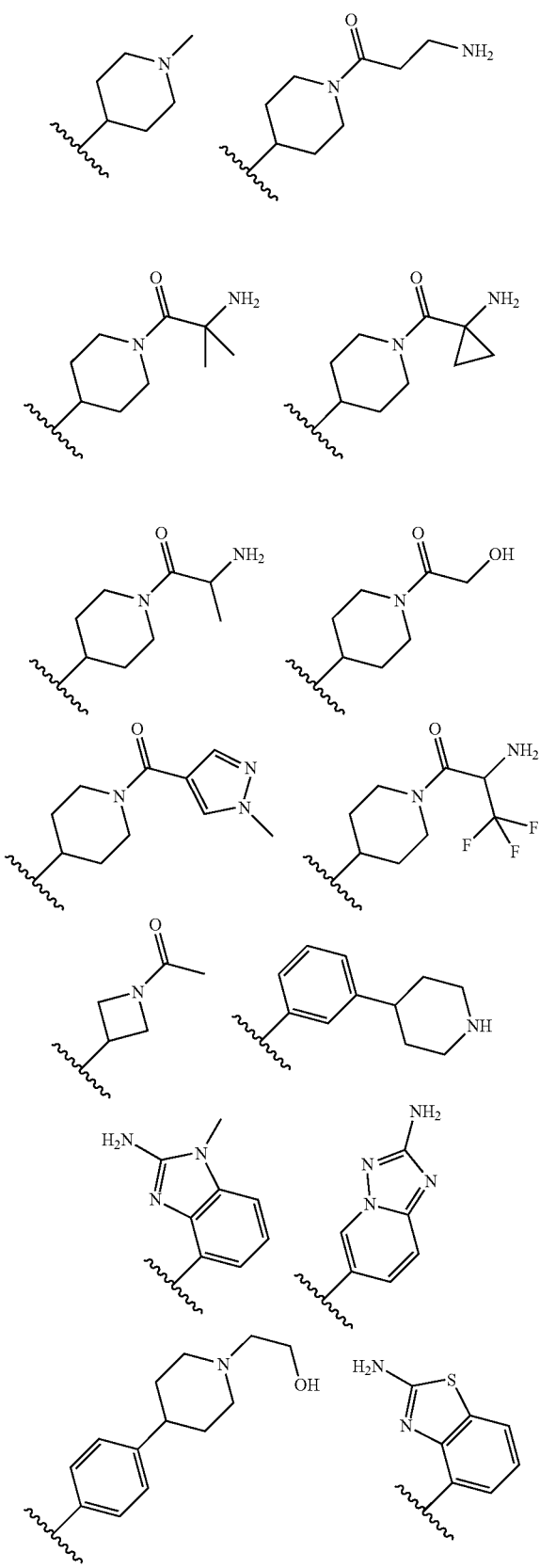

Other preferred examples of R¹ include:

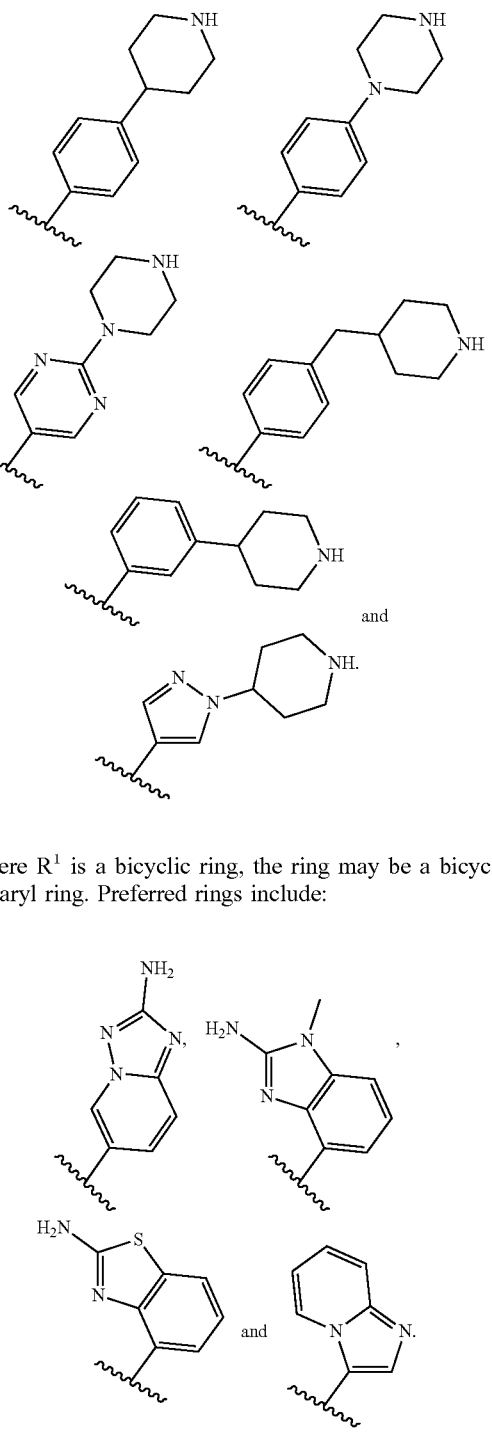

Where R¹ is a bicyclic ring, the ring may be a bicyclic heteroaryl ring. Preferred rings include:

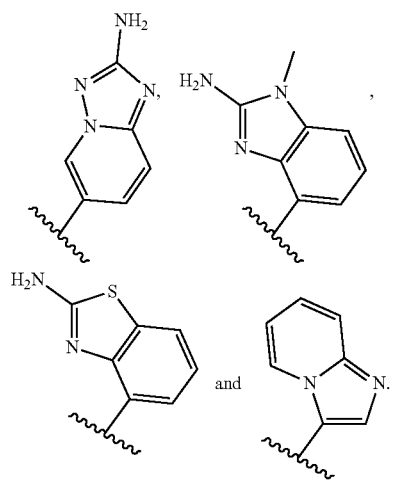

In an alternative embodiment, R¹ is a saturated or partially saturated ring system. In one embodiment, R¹ is a fused bicyclic ring system. R¹ may also be a monocyclic ring system. The ring system may be carbocyclic or heterocyclic.

When R¹ is a saturated ring, the ring may be carbocyclic or heterocyclic and consequently the ring may be carbon-linked or nitrogen linked to the pyrrole core. In the case of carbon-linked rings, preferred rings include:

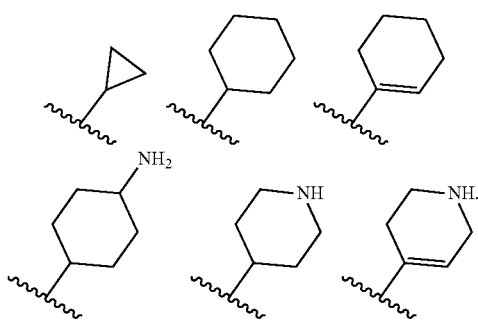

In the case of nitrogen-linked rings, preferred $R^1$ groups include:

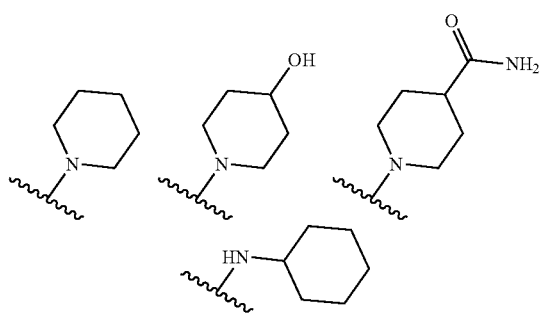

In an alternative preferred embodiment, $R^1$ is

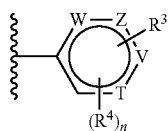

in which all of T, V, W and Z are C and n is 1 or 2.

In an alternate embodiment of $R^1$, T is C, V is C, W is N and Z is C.

In another alternative embodiment of $R^1$, T is C, V is C, W is C and Z is N.

In another alternative embodiment of $R^1$, T is C, V is N, W is C and Z is C.

In another preferred embodiment of $R^1$, T is absent, V is N, W is C and Z is N.

In an embodiment, $R^2$ is —C(O)OH or —C(O)OM. In an embodiment, $R^2$ is —C(O)OH. In an embodiment, $R^2$ is —C(O)OM.

Alternatively, $R^2$ may be:

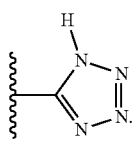

In embodiments $R^3$ is either absent or is selected as appropriate to satisfy valence requirements from the group comprising: H, halo, CN, oxo, $C_{1-6}$ alkyl, $C_{1-6}$ alkoxy, $C_{2-6}$ alkenyl, $C_{2-6}$alkynyl, $C_{3-8}$ cycloalkyl, —$(CH_2)_d$—$C_{6-10}$ aryl, —$(CH_2)_d$-5 to 10 membered heteroaryl, —$(CH_2)_e$-3 to 10 membered heterocyclyl, —$OR^5$, —$N(R)_2$, —$SO_2R^5$, —$SO_2N(R)_2$, —$NHSO_2R^7$, —$NHCOR^5$, —$CON(R^5)_2$ and —$COR^5$ wherein each of the above substituents apart from H may themselves be optionally substituted where chemically possible with one, two or three groups independently selected at each occurrence from the group comprising: halo, —$N(R)_2$, —OH, —C(=O)$C_{1-6}$ alkyl, —$SO_2NC_{1-6}$ alkyl, —$(CH_2)_nOR^5$, $C_{1-6}$ alkyl, $C_{2-6}$ alkenyl, $C_{2-6}$ alkynyl, $C_{3-8}$ cycloalkyl, and $C_{3-8}$ cycloalkenyl.

In embodiments $R^3$ is either absent or is selected as appropriate to satisfy valence requirements from the group comprising: H, halo, CN, oxo, $C_{1-6}$ alkyl, $C_{1-6}$ alkoxy, $C_{2-6}$ alkenyl, $C_{2-6}$alkynyl, $C_{3-8}$ cycloalkyl, —$(CH_2)_d$—$C_{6-10}$ aryl, —$(CH_2)_d$-5 to 10 membered heteroaryl, —$(CH_2)_e$-3 to 10 membered heterocyclyl, —$OR^5$, —$N(R)_2$, —$SO_2R^5$, —$SO_2N(R)_2$, —$NHSO_2R^7$, —$NHCOR^5$, —$CON(R^5)_2$ and —$COR^5$ wherein each of the above substituents apart from H may themselves be optionally substituted where chemically possible with one, two or three groups independently selected at each occurrence from the group comprising: halo, —$N(R^5)_2$, —OH, —C(=O)$C_{1-6}$ alkyl, —$SO_2NC_{1-6}$ alkyl, $C_{1-6}$ alkyl, $C_{2-6}$ alkenyl, $C_{2-6}$ alkynyl, $C_{3-8}$ cycloalkyl, and $C_{3-8}$ cycloalkenyl.

In embodiments $R^3$ is either absent or is selected as appropriate to satisfy valence requirements from the group comprising: halo, CN, oxo, $C_{1-6}$ alkyl, $C_{1-6}$ alkoxy, 3 to 10 membered heterocyclyl, —$OR^5$, —$N(R^5)_2$, —$SO_2R^5$, —$SO_2N(R^5)_2$, —$NHSO_2R^7$, and —$COR^5$ wherein each of the above substituents (preferably 3 to 10 membered heterocyclyl) may themselves be optionally substituted where chemically possible with one, two or three groups (preferably 1 or 2 groups) independently selected at each occurrence from the group comprising: halo, —C(=O)$C_{1-6}$ alkyl or —$SO_2N(C_{1-6}$ alkyl$)_2$.

In embodiments $R^3$ is either absent or is selected as appropriate to satisfy valence requirements from the group comprising: methyl, fluoro, —CN, =O, —OH, —OMe —$NH_2$, —COOH, —C(=O)Me, —$SO_2Me$, —$SO_2NMe_2$, —$SO_2NH(CH_2)_2NH_2$, —$SO_2NH(CH_2)_2NHC(=O)O^tBu$, —C(=O)$CH_2NH_2$, —C(=O)$CH_2OH$, —C(=O)$CH_2NH_2$, —C(=O)$(CH_2)_2NH_2$, —C(=O)C$(CH_3)_2NH_2$, —C(=O)C(cyclopropyl)$NH_2$, —C(=O)CH$(CH_3)NH_2$, —C(=O)$NH_2$, —C(=O)NHMe, —C(=O)NH$(CH_2)_2NH_2$, —C(=O)NH$(CH_2)_3NH_2$, —C(=O)-pyrazolyl, —C(=O)-methylpyrazolyl, —C(=O)CH$(NH_2)CF_3$, —NHC(=O)Me, —NHC(=O)-cyclopropyl, —$NHSO_2(CH_2)_2NH_2$, —$NHSO_2$-imidazolyl, —$NHSO_2$-phenyl, —$NHSO_2$-isopropyl, —$NHSO_2$-cyclopropyl, —$CH_2$-morpholine, pyridine, piperidine, tetrahydropyridine, piperazine, —O-piperidine, piperidine substituted with —$SO_2NMe_2$, piperidine substituted with —C(=O)Me, piperidine substituted with —$(CH_2)_{2O}$-benzyl, piperidine substituted with —$(CH_2)_2OH$, morpholine, —$NHSO_2$-cyclopropyl, or —$SO_2$-piperazine.

In embodiments $R^3$ is either absent or is selected as appropriate to satisfy valence requirements from the group comprising: methyl, fluoro, —CN, =O, —OH, —OMe —$NH_2$, —$SO_2Me$, —$SO_2NMe_2$, —$SO_2NH(CH_2)_2NH_2$, —C(=O)$CH_2NH_2$ pyridine, piperidine, piperidine substituted with —$SO_2NMe_2$, piperidine substituted with —C(=O)Me, morpholine, —$NHSO_2$— cyclopropyl, or —$SO_2$-piperazine.

In an embodiment, $R^3$ is aryl or heterocyclyl. In an embodiment, $R^3$ is $C_{6-10}$ aryl or 5 to 10 membered heterocyclyl (optionally heteroaryl). In one embodiment, $R^3$ is phenyl. In an alternative embodiment, $R^3$ is heterocyclyl i.e. it is a heterocyclic ring. The heterocyclic ring may be a substituted or unsubstituted pyridine ring. In another embodiment, $R^3$ is substituted or unsubstituted piperidine.

In embodiments, $R^3$ is a substituted or unsubstituted phenyl, pyridyl, or pyrazole. The pyridyl group may be a 3-pyridyl or 4-pyridyl group.

Preferred examples of $R^3$ are selected from: —$NH_2$, oxo, methyl, —$SO_2Me$, —$SO_2N(Me)_2$, and 4-piperidinyl.

$R^4$ is independently selected at each occurrence from the group comprising: H, halo, $C_{1-6}$ alkyl, $C_{2-6}$ alkenyl, $C_{2-6}$ alkynyl, $C_{3-3}$ cycloalkyl, $C_{3-3}$ cycloalkenyl, —$(CH_2)_f$—$C_{6-10}$ aryl, —$(CH_2)_d$-5 to 10 membered heteroaryl, —$(CH_2)_g$-3 to 10 membered heterocyclyl; wherein each $R^4$ may themselves be optionally substituted where chemically possible with one, two or three groups independently selected at each occurrence from the group comprising: halo, —$NH_2$, —$N(C_{1-4}$ alkyl$)_2$, —OH, —$SO_2N(C_{1-4}$ alkyl$)_2$, and —C(=O)Otert-butyl.

In embodiments, $R^4$ is selected at each occurrence from the group comprising: H, halo, substituted or unsubstituted $C_{1-6}$ alkyl, and substituted or unsubstituted $C_{3-8}$ cycloalkyl.

In embodiments, $R^4$ is selected at each occurrence from the group comprising: H, halo, unsubstituted $C_{1-6}$ alkyl, and unsubstituted $C_{3-8}$ cycloalkyl.

Preferably $R^4$ is H, fluoro or Me.

$R^5$ is independently selected at each occurrence from the group comprising: H, —OH, $C_{1-6}$ alkyl, $C_{1-6}$ haloalkyl, $C_{2-6}$ alkenyl, $C_{2-6}$ alkynyl, $C_{3-3}$ cycloalkyl, $C_{3-3}$ cycloalkenyl, —$(CH_2)_f$—$C_{6-10}$ aryl, —$(CH_2)_d$-5 to 10 membered heteroaryl, —$(CH_2)_g$-3 to 10 membered heterocyclyl; wherein each $R^5$ may themselves be optionally substituted where chemically possible with one, two or three groups independently selected at each occurrence from the group comprising: halo, —$NH_2$, —$N(C_{1-4}$ alkyl$)_2$, —OH, —$SO_2N(C_{1-4}$ alkyl$)_2$, —NHC(=O)Otert-butyl and —C(=O)Otert-butyl.

$R^5$ is independently selected at each occurrence from the group comprising: H, —OH, $C_{1-6}$ alkyl, $C_{1-6}$ haloalkyl, 3 to 10 membered heterocyclyl, $C_{3-8}$ cycloalkyl; wherein each $R^5$ may themselves be optionally substituted where chemically possible with one or two groups independently selected at each occurrence from the group comprising: —$NH_2$, —OH, —$SO_2N(C_{1-4}$alkyl$)_2$, —NHC(=O)Otert-butyl and —C(=O)Otert-butyl.

$R^5$ is independently selected at each occurrence from the group comprising: H, —OH, methyl, propyl, methylamine, ethylamine, n-propylamine, iso-propylamine, trifluoroethylamine, piperidine, cyclopropyl, cyclopropylamine, —$CH_2OH$, —$(CH_2)_2NHC(=O)Otert$-butyl, methylpyrazole, piperazine, piperazine substituted with —C(=O)Otert-butyl, In an embodiment, $R^5$ is selected from the group comprising: H, substituted or unsubstituted $C_{1-6}$ alkyl, and substituted or unsubstituted $C_{3-8}$ cycloalkyl. Preferably $R^5$ is H.

In an embodiment, $R^6$ is H, Me, ethyl or $CF_3$. In an embodiment, $R^6$ is H, Me or $CF_3$. In some embodiments $R^6$ is H.

In other embodiments, $R^7$ is $C_{1-4}$ alkyl or $C_{6-10}$ aryl or 5 to 10 membered heteroaryl or $C_{1-4}$ alkyl amine or $C_{3-3}$ cycloalkyl. In embodiments, $R^7$ is iso-propyl, ethylamine cyclopropyl, phenyl, methylimidazolyl or pyridyl. In embodiments $R^7$ is $C_{3-3}$ cycloalkyl. Optionally, $R^7$ is cyclopropyl.

In embodiments, L is absent, —$CH_2$—, —$CH_2NH$—, —O—, or —$OCH_2$—. In embodiments, L is absent. In alternative embodiments L is O or NH. In embodiments, L may be —$CH_2$— or —$CH_2CH_2$—.

In embodiments, a is 0 or 1. In embodiments, a is 0.
In embodiments, b is 0 or 1. In embodiments, b is 0.
In embodiments, d is 0 or 1. In embodiments, d is 0.
In embodiments, e is 0 or 1. In embodiments, e is 0.
In embodiments, f is 0 or 1. In embodiments, f is 0.
In embodiments, g is 0 or 1. In embodiments, g is 0.
In embodiments, h is 0, 1 or 2. In embodiments, h is 0. In embodiments, h is 1.

In embodiments M is Na or K, preferably Na.

The various embodiments described above for the various substituents may be applied independently of one another. These embodiments apply similarly to all of the other aspects of the invention which are described below.

In an embodiment of the present invention, the compound according to Formula (I) may be a compound selected from:

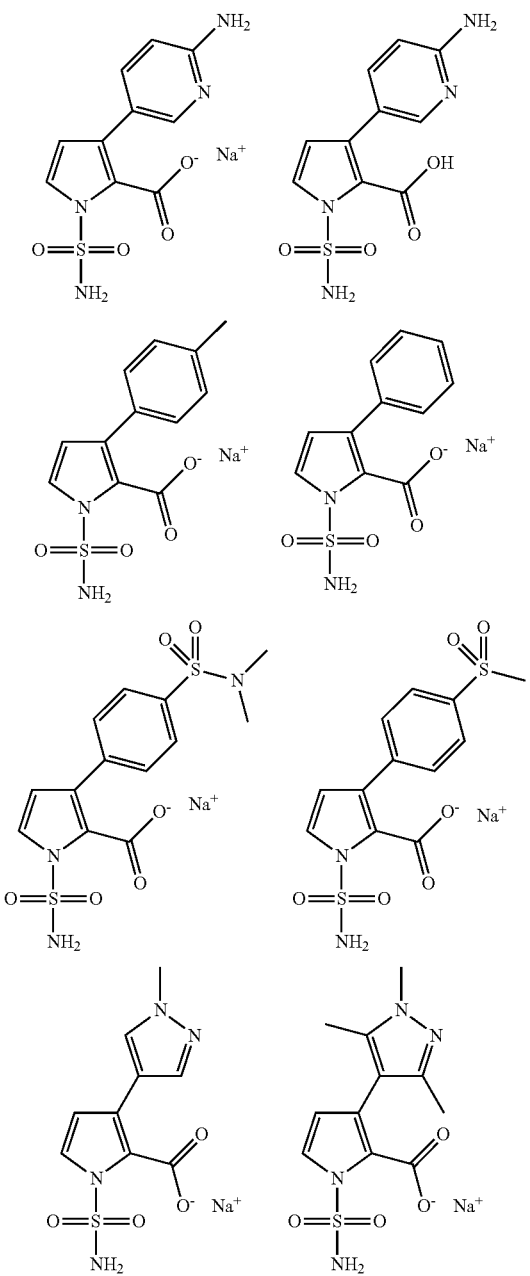

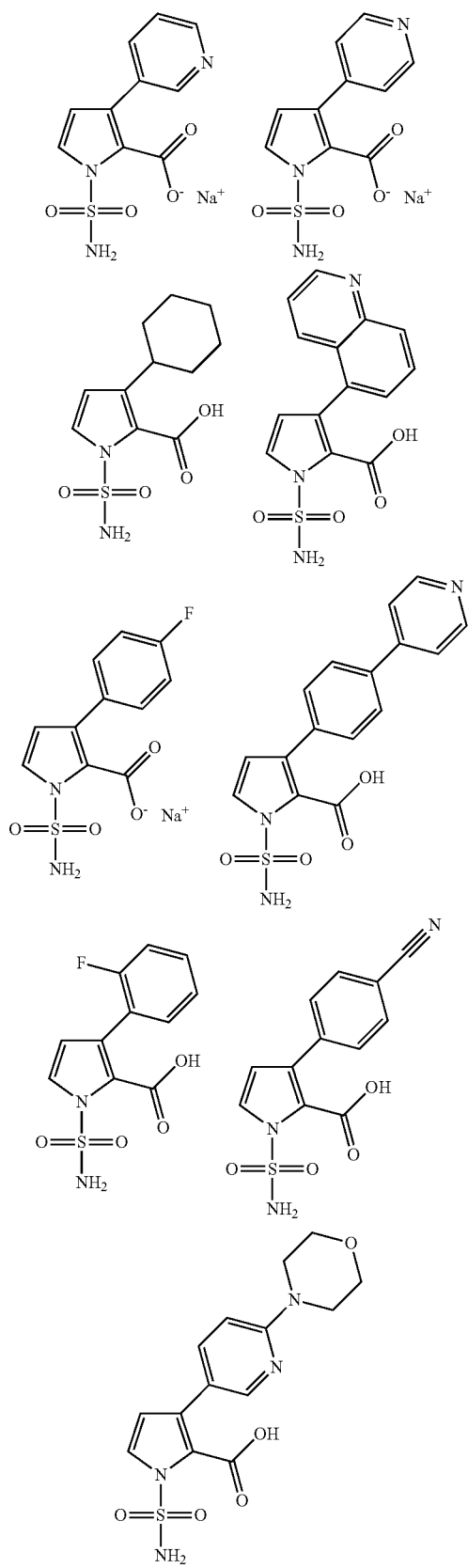
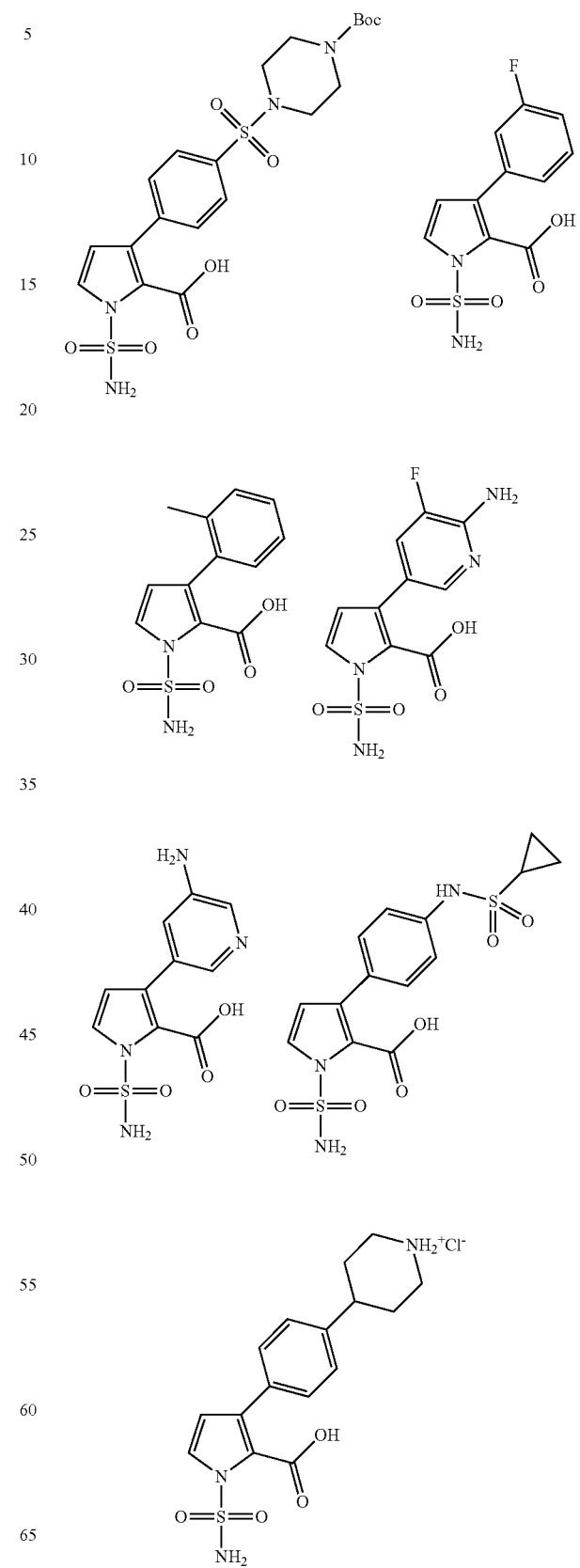

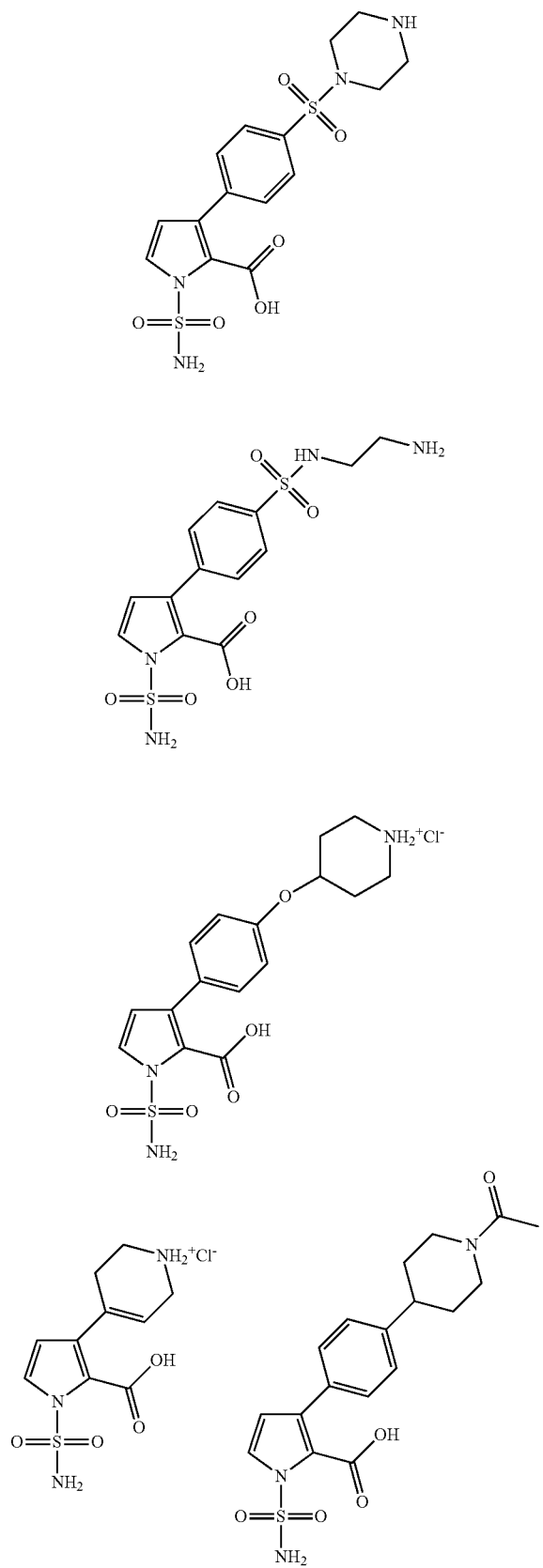
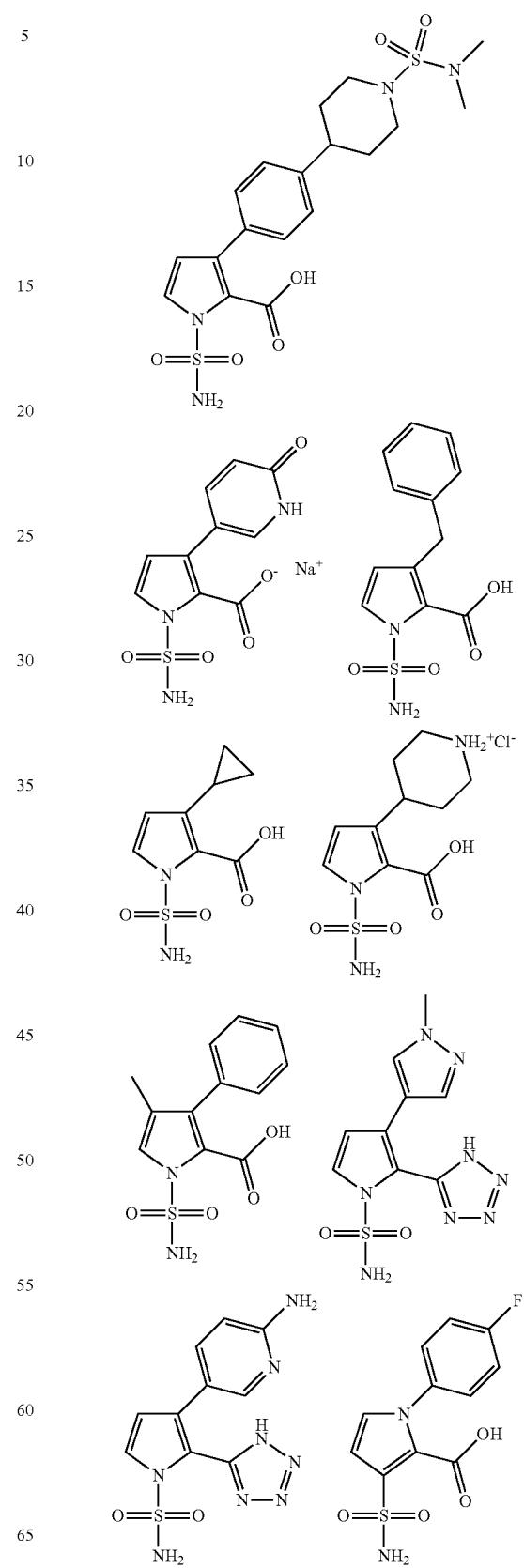

25
-continued
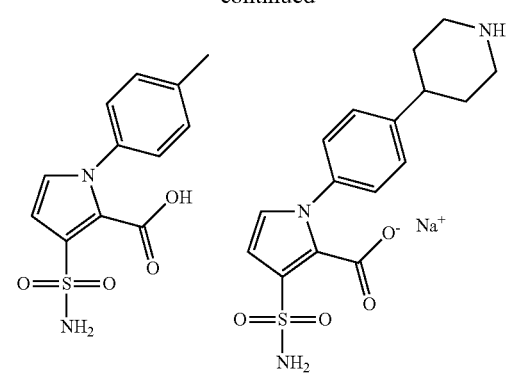
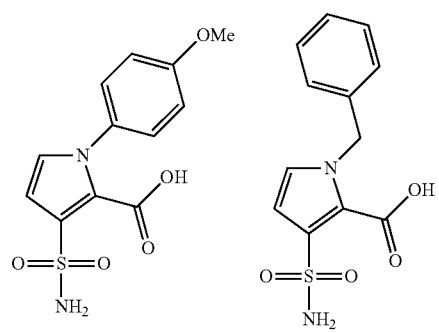
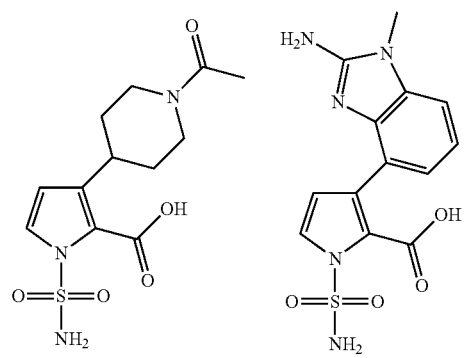
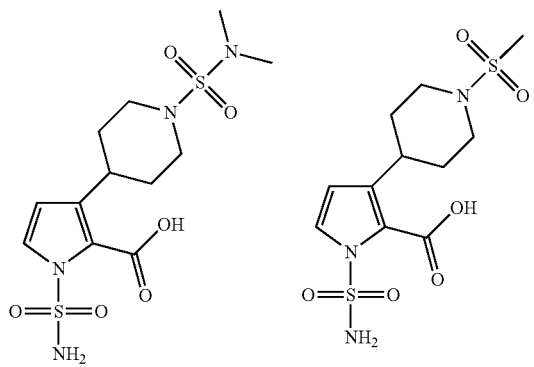
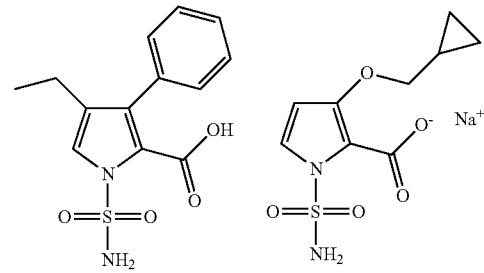
26
-continued
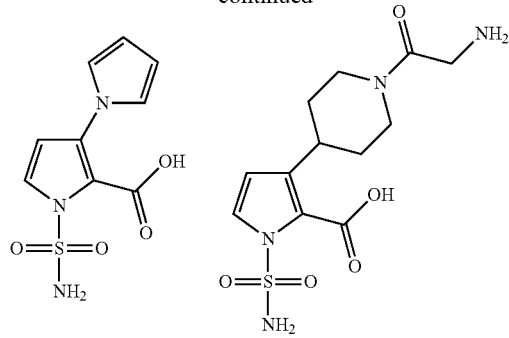
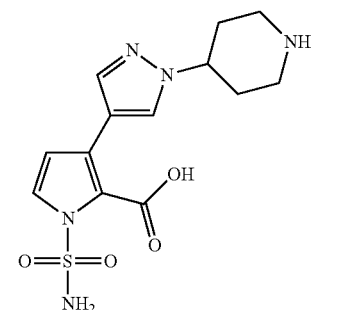
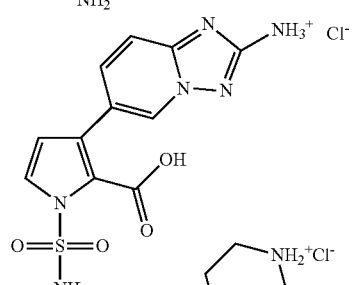
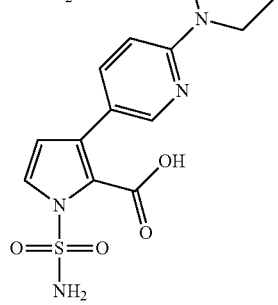
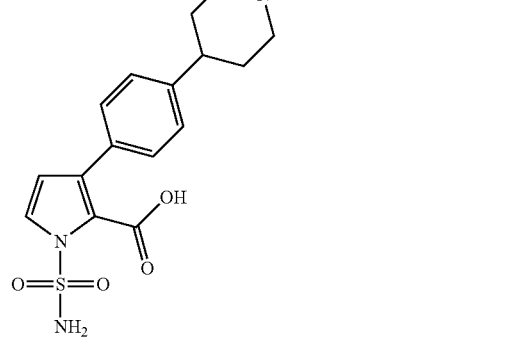

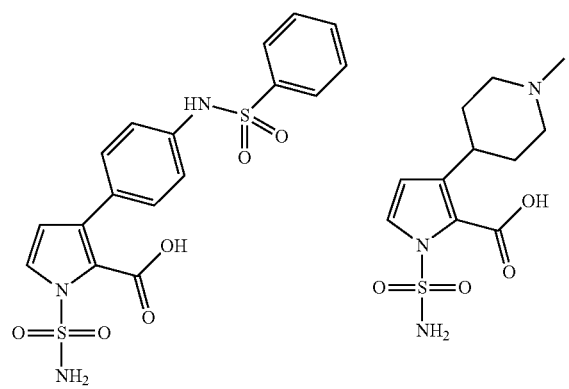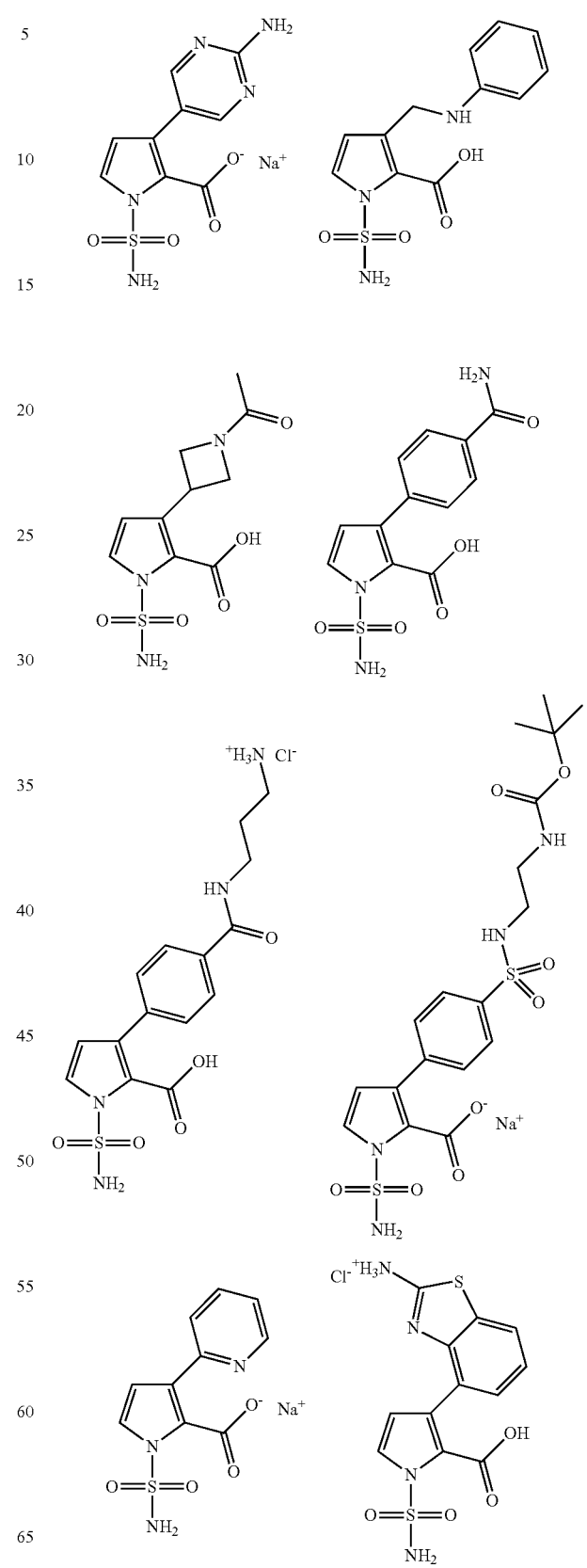

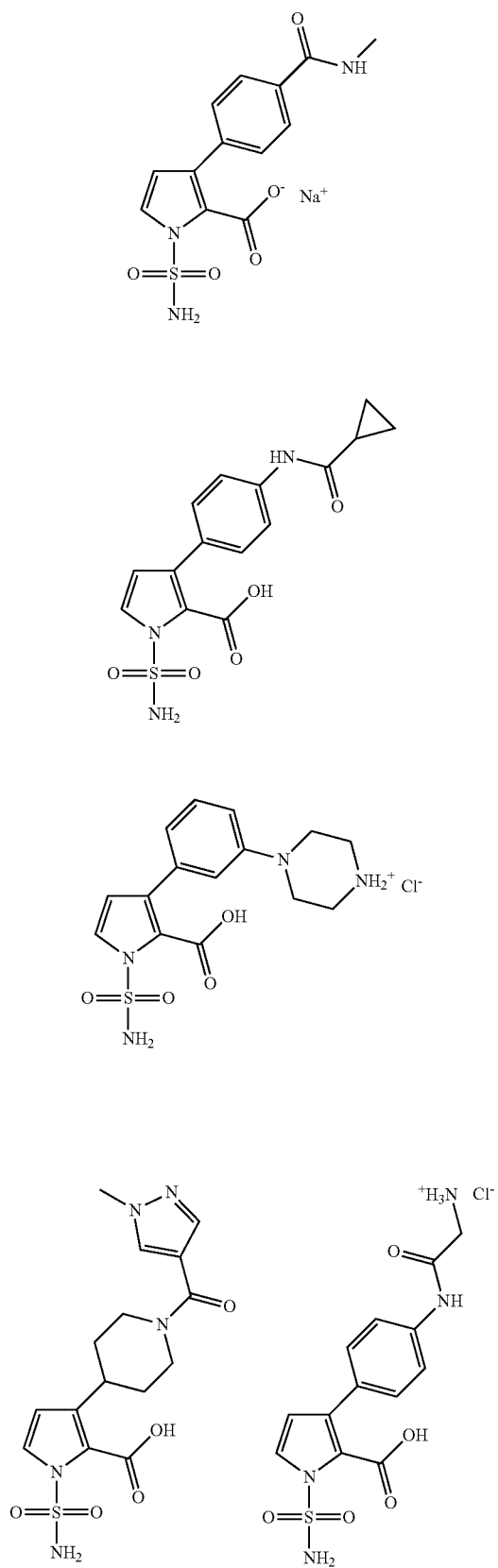
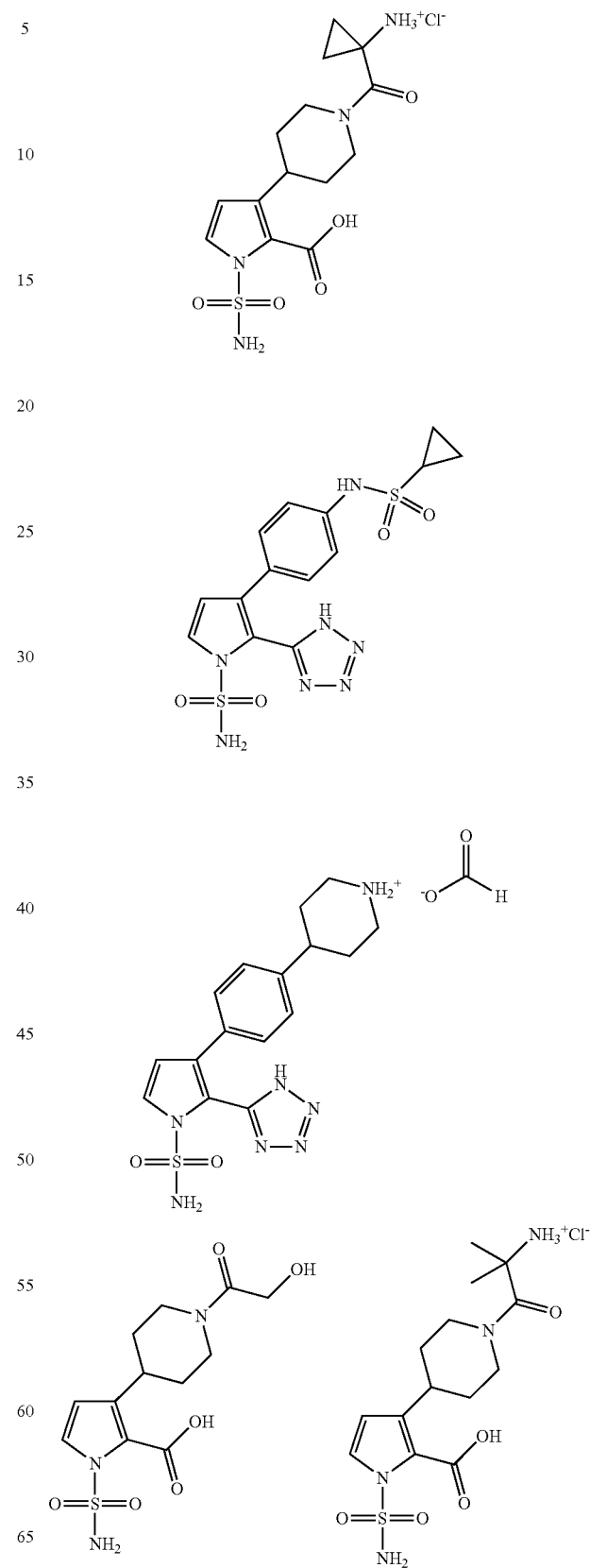

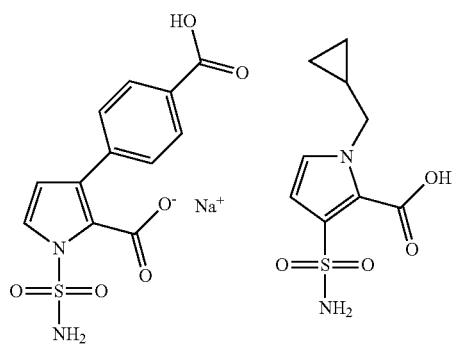
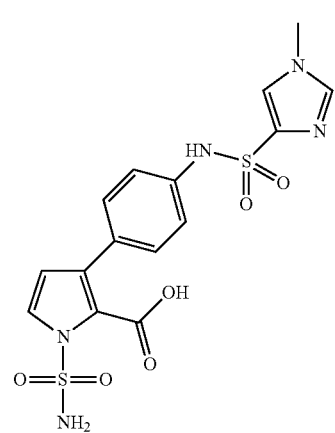
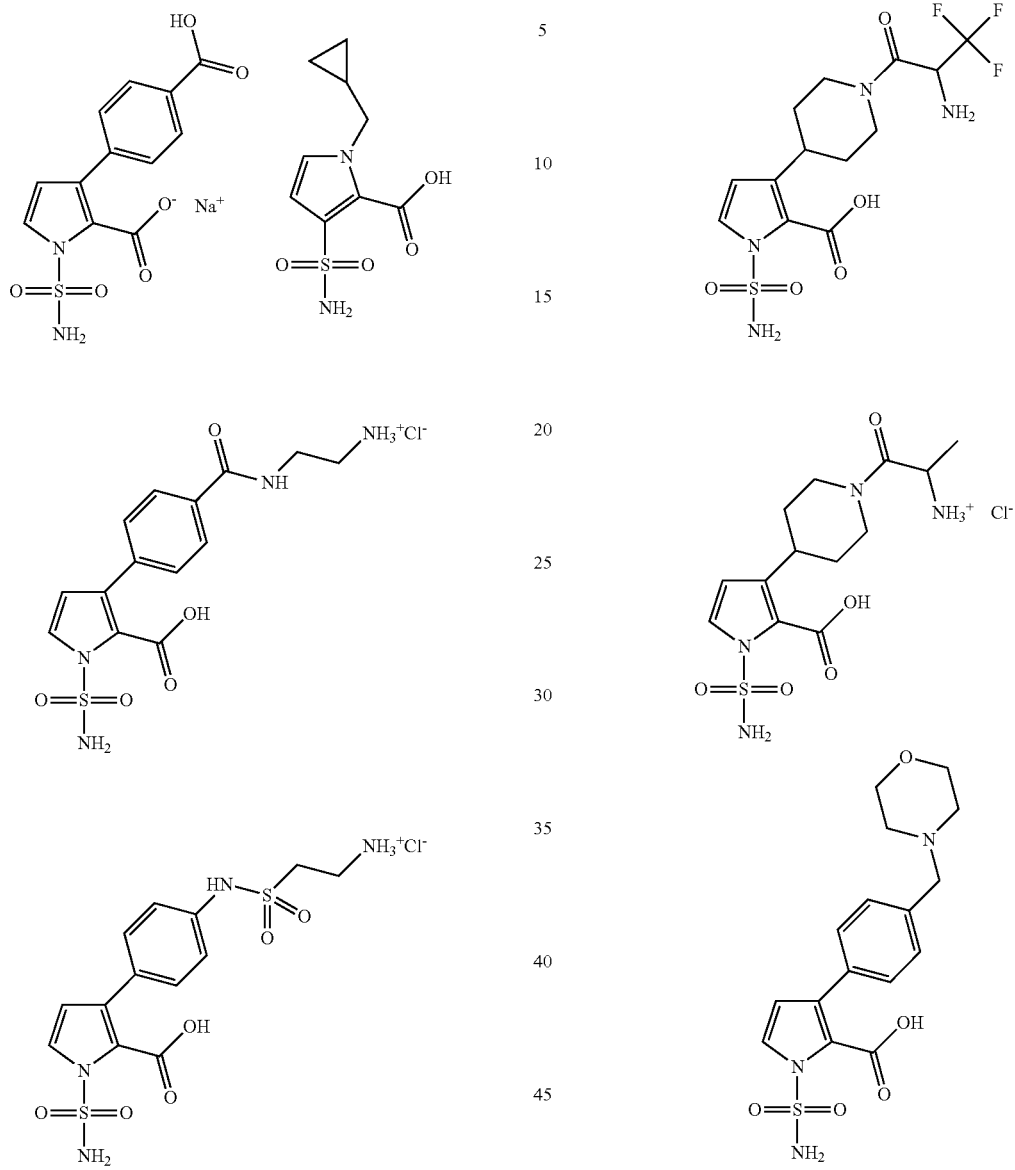

According to a further aspect of the invention there is provided a pharmaceutical composition which comprises a compound of Formula (I), or a pharmaceutically acceptable salt, hydrate or solvate thereof, in association with one or more pharmaceutically acceptable excipients.

Compounds of the invention have been described throughout the present application as a compound or a salt of a compound. It would be understood by the skilled person that a compound can be converted into a salt and a salt can be converted into a compound, in other words the free acid or free base corresponding to the salt. Accordingly, where a compound is disclosed or where a salt is disclosed, the present invention also includes the corresponding salt form, free acid form or free base form, as appropriate. For example, the disclosure of the below salt also covers the disclosure of the corresponding free acid, also shown below. This applies to all compounds or salts disclosed herein.

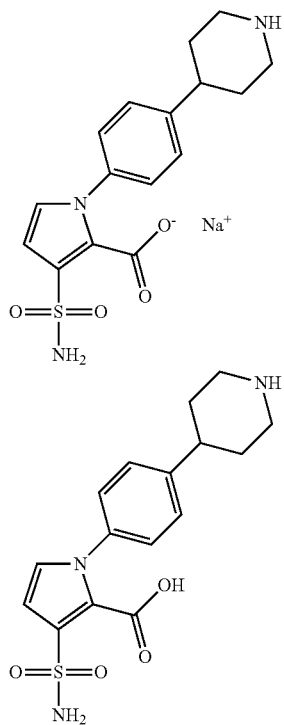

The compounds of the present invention are inhibitors of metallo-beta-lactamases (MBLs). As discussed above, many bacteria have developed resistance to β-lactam antibacterials (BLAs) and one of the main resistance mechanisms is the hydrolysis of BLAs by MBLs. The compounds of the invention address this issue. In particular, the inhibition of bacterial MBLs by the compounds of Formula (I) can significantly enhance the activity of BLAs when one or more of these compounds is administered with a compound of the present invention.

Bacterial infections which can be treated using compounds of Formula (I) and compositions containing compounds of Formula (I) include those caused by Gram-negative or Gram-positive bacteria. For example, the bacterial infection may be caused by bacteria from one or more of the following families; *Streptococcus, Acinetobacter Staphylococcus, Clostridium, Pseudomonas, Escherichia, Salmonella, Klebsiella, Legionella, Neisseria, Enterococcus, Enterobacter, Serratia, Stenotrophomonas, Aeromonas, Mycobacterium, Morganella, Yersinia, Pasteurella, Haemophilus, Citrobacter, Burkholderia, Brucella,* or *Moraxella.*

Particular examples of bacteria which are targeted by this invention include bacterial strains in the following families of bacteria: *Escherichia, Acinetobacter, Pseudomonas,* and *Klebsiella.*

The bacterial infection may, for example, be caused by one or more bacteria selected from *Escherichia coli, Acinetobacter baumannii, Pseudomonas aeruginosa* or *Klebsiella pneumonia.*

In one aspect of the present invention, the present invention provides a compound of Formula (I), or a pharmaceutically acceptable salt, hydrate or solvate thereof, for use in the inhibition of metallo-beta-lactamase activity.

In another aspect, the present invention provides a compound of Formula (I), or a pharmaceutically acceptable salt, hydrate or solvate thereof, for use in the treatment of a disease or disorder in which metallo-beta-lactamase activity is implicated.

In an embodiment, compounds of the present invention may be for use in the treatment of a disease or disorder caused by aerobic or anaerobic Gram-positive or aerobic or anaerobic Gram-negative bacteria. In an embodiment, the disease or disorder is caused by metallo-beta-lactamase producing Gram-positive bacteria.

In an embodiment, compounds of the present invention may be for use in the treatment of a disease or disorder selected from: pneumonia, respiratory tract infections, urinary tract infections, intra-abdominal infections, skin and soft tissue infections, bloodstream infections, septicaemia, intra- and post-partum infections, prosthetic joint infections, endocarditis, acute bacterial meningitis and febrile neutropenia.

In an embodiment, compounds of the present invention may be for use in the treatment of a disease or disorder selected from: community acquired pneumonia, nosocomial pneumonia (hospital-acquired/ventilator-acquired), respiratory tract infections associated with cystic fibrosis, non-cystic fibrosis bronchiectasis, COPD, urinary tract infection, intra-abdominal infections, skin and soft tissue infection, bacteraemia, septicaemia, intra- and post-partum infections, prosthetic joint infections, endocarditis, acute bacterial meningitis and febrile neutropenia.

In an embodiment, compounds of the present invention may be for use in the treatment of a disease or disorder selected from: community acquired pneumonia, nosocomial pneumonia (hospital-acquired/ventilator-acquired), respiratory tract infections associated with cystic fibrosis, non-cystic fibrosis bronchiectasis, COPD, urinary tract infection, intra-abdominal infections, skin and soft tissue infection, bacteraemia and septicaemia.

In embodiments, the compounds of the present invention may be for use in a method of treatment, wherein the compound is administered in combination with one or more BLAs.

Administration of the compound or compounds of Formula (I) may be together with one or more BLAs which are all present in the same dosage form or it may be the case that the one or more BLAs are presented in separate dosage forms and the one or more compounds of Formula (I) are presented in separate dosage forms. In a preferred embodiment, an effective antibacterial treatment will consist of a compound of Formula (I) and a BLA. The BLA will preferably be meropenem. In another preferred embodiment, the compound of Formula (I) is co-administered with the BLA, which can preferably be meropenem, in a single formulation i.e. a single dosage form.

The compounds of Formula (I) may be presented in dosage forms which are suitable for oral use (for example as tablets, lozenges, hard or soft capsules, aqueous or oily suspensions, emulsions, dispersible powders or granules, syrups or elixirs), or they may be suitable for topical use (for example as creams, ointments, gels, or aqueous or oily solutions or suspensions). Other suitable dosage forms also include those intended for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing). In a preferred embodiment oral or intravenous administration is preferred, with intravenous administration being most preferred.

Oral dosage formulations may contain, together with the active compound, one or more of the following excipients: diluents, lubricants, binding agents, desiccants, sweeteners, flavourings, colouring agents, wetting agents, and effervescing agents.

If the MBL and BLA are presented in separate dosage forms, these may be administered simultaneously or sequentially. Usually, it is preferred to administer the MBL i.e. the compound of Formula (I) of the invention and the BLA i.e. the antibacterial compound in a single dosage form. Preferably this is an intravenous dosage form, and more preferably it is a solid dosage form. Tablets, capsules and caplets are particularly preferred.

The process of contacting a cell, or indeed other biological material or samples, which contain bacteria with compounds of the invention effectively means exposing bacteria to compounds of the invention.

Compounds of Formula (I) are inhibitors of metallo-beta-lactamases and the present invention therefore provides a method of inhibiting bacterial metallo-beta-lactamase activity in vitro or in vivo. This method comprises contacting a cell with an effective amount of a compound of Formula (I), or a pharmaceutically acceptable salt, hydrate or solvate thereof, or contacting a cell with a pharmaceutical composition containing a compound of Formula (I) or a pharmaceutically acceptable salt, hydrate or solvate thereof.

Accordingly, in one aspect of the invention, there is provided a method of inhibiting bacterial metallo-beta-lactamase activity in vitro or in vivo, the method comprising contacting a cell with an effective amount of a compound of Formula (I), or a pharmaceutically acceptable salt, hydrate or solvate thereof; or contacting a cell with a pharmaceutical composition containing a compound of Formula (I) or a pharmaceutically acceptable salt, hydrate or solvate thereof.

The present invention also provides a method for the prevention or treatment of bacterial infection in a patient in need of such treatment, said method comprising administering to said patient a therapeutically effective amount of a combination of an antibacterial agent with a compound of Formula (I) or a pharmaceutically acceptable salt, hydrate or solvate thereof; or administering to said patient a therapeutically effective amount of an antibacterial agent in combination with a pharmaceutical composition containing a compound of Formula (I) or a pharmaceutically acceptable salt, hydrate or solvate thereof.

The present invention also provides a method for the prevention or treatment of a disease or disorder, said method comprising administering to a patient in need of such treatment a therapeutically effective amount of a combination of an antibacterial agent with a compound of Formula (I) or a pharmaceutically acceptable salt, hydrate or solvate thereof; or administering to said patient a therapeutically effective amount of an antibacterial agent in combination with a pharmaceutical composition containing a compound of Formula (I) or a pharmaceutically acceptable salt, hydrate or solvate thereof.

In an embodiment, the present invention provides a method for the prevention or treatment of a disease or disorder caused by aerobic or anaerobic Gram-positive or aerobic or anaerobic Gram-negative bacteria. In an embodiment, the disease or disorder is caused by metallo-beta-lactamase producing Gram-positive bacteria.

In an embodiment, the present invention provides a method for the prevention or treatment of a disease or disorder selected from: pneumonia, respiratory tract infections, urinary tract infections, intra-abdominal infections, skin and soft tissue infections, bloodstream infections, septicaemia, intra- and post-partum infections, prosthetic joint infections, endocarditis, acute bacterial meningitis and febrile neutropenia.

In an embodiment, the present invention provides a method for the prevention or treatment of a disease or disorder selected from: community acquired pneumonia, nosocomial pneumonia (hospital-acquired/ventilator-acquired), respiratory tract infections associated with cystic fibrosis, non-cystic fibrosis bronchiectasis, COPD, urinary tract infection, intra-abdominal infections, skin and soft tissue infection, bacteraemia, septicaemia, intra- and post-partum infections, prosthetic joint infections, endocarditis, acute bacterial meningitis and febrile neutropenia.

In an embodiment, the present invention provides a method for the prevention or treatment of a disease or disorder selected from: community acquired pneumonia, nosocomial pneumonia (hospital-acquired/ventilator-acquired), respiratory tract infections associated with cystic fibrosis, non-cystic fibrosis bronchiectasis, COPD, urinary tract infection, intra-abdominal infections, skin and soft tissue infection, bacteraemia and septicaemia.

In an embodiment, the antibacterial agent is a carbapenem. Non limiting examples of carbapenems include: meropenem, faropenem, imipenem, ertapenem, doripenem, panipenem/betamipron and biapenem as well as razupenem, tebipenem, lenapenem and tomopenem.

The present invention also provides a method of inhibiting bacterial infection, said method comprising contacting a cell with an effective amount of a compound of Formula (I), or a pharmaceutically acceptable salt, hydrate or solvate thereof, in combination with a suitable antibacterial agent. The contacting of the cell may occur in vitro or in vivo, with in vivo contact being preferred.

Another aspect of the invention provides a compound of Formula (I), or a pharmaceutically acceptable salt, hydrate or solvate thereof, or a pharmaceutical composition containing a compound of Formula (I) or a pharmaceutically acceptable salt, hydrate or solvate thereof, for use in therapy.

A further aspect of the present invention provides a compound of Formula (I), or a pharmaceutically acceptable salt, hydrate or solvate thereof, or a pharmaceutical containing a compound of Formula (I) or a pharmaceutically acceptable salt, hydrate or solvate thereof, for use in the treatment of a bacterial infection. The treatment may be curative or preventative i.e. prophylactic. In a preferred embodiment, the treatment is curative; this means that the treatment reduces the overall level of bacterial infection.

A further aspect of the invention provides a kit of parts comprising a compound of Formula (I), or a pharmaceutically acceptable salt, hydrate or solvate thereof, or a pharmaceutical composition containing a compound of Formula (I) or a pharmaceutically acceptable salt, hydrate or solvate thereof, and a BLA. The kit may be provided together with instructions for use in treating bacterial infections and/or packaging which provides the combined dose of the compound of Formula (I) and the BLA.

The chemical terms used in the specification have their generally accepted meanings in the art.

The term "halo" refers to fluoro, chloro, bromo and iodo.

The term "alkyl" includes both straight and branched chain alkyl groups and analogues thereof having from 1 to 6 carbon atoms. References to individual alkyl groups such as "propyl" are specific for the straight chain version only and references to individual branched chain alkyl groups such as "isopropyl" are specific for the branched chain version only. Similarly, a C4 alkyl may be straight chain butyl, secondary butyl (sec-butyl) or tertiary butyl (tert-butyl). At each occurrence the term may have any meaning within the above definition independently of any other usage of the term. The same comment applies to other terms defined in this specification which are used on multiple occasions and which are therefore independently chosen on each occasion from within the overall defined meaning.

For the avoidance of doubt, the term "$C_{3-8}$ cycloalkyl" means a hydrocarbon ring containing from 3 to 8 carbon atoms, for example, cyclopropyl, cyclobutyl, cyclopentyl, cyclohexyl, cycloheptyl or bicyclo[2.2.1]heptyl; and the term "$C_{3-8}$cycloalkenyl" means a hydrocarbon ring containing at least one double bond, for example, cyclobutenyl, cyclopentenyl, cyclohexenyl or cycloheptenyl, such as 3-cyclohexen-1-yl, or cyclooctenyl.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The heterocyclic ring may be saturated, unsaturated or aromatic. Aromatic heterocyclic species are generally referred to as heteroaryl rings.

The term "heterocyclyl", "heterocyclic" or "heterocycle" means a non-aromatic saturated or partially saturated monocyclic, fused, bridged, or spiro bicyclic heterocyclic ring system(s).

The term heterocyclyl includes both monovalent species and divalent species. Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocycles contain from about 7 to about 17 ring atoms, suitably from 7 to 12 ring atoms. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro oxathiolyl, tetrahydro oxazolyl, tetrahydro-oxadiazolyl, tetrahydrodioxazolyl, tetrahydro oxathiazolyl, hexahydrotriazinyl, tetrahydrooxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxo-imidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo [2.2.1]heptane, 2-oxa-5-azabicyclo[2.2.1]heptane, aza-bicyclo[2.2.2]octane, aza-bicyclo[3.2.1]octane and quinuclidine.

The term "heteroaryl" or "heteroaromatic" means an aromatic mono-, bi-, or polycyclic ring incorporating one or more (for example 1 to 4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically, the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3 b]furanyl, 2H-furo[3,2-b]pyranyl, 5H-pyrido[2,3-d]oxazinyl, 1H-pyrazolo[4,3-d]oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2 b][1, 4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

5- or 6-membered heterocyclic rings are preferred.

The various functional groups and substituents making up the compounds of the formula I are typically chosen such that the molecular weight of the compound of the formula I does not exceed 1000. More usually, the molecular weight of the compound will be less than 900, for example less than 800, or less than 700, or less than 650, or less than 600. More preferably, the molecular weight is less than 550 and, for example, is 500 or less.

The invention contemplates pharmaceutically acceptable salts of the compounds of the invention. Suitable pharmaceutically acceptable salts of compounds of the present invention include salts with Group 1 cations (for example Na$^+$), Group II cations (for example K$^+$) or ammonium salts (for example NH$_4^+$). The compounds of the present invention may also form a hydrochloride salt, phosphate salt or salts of other inorganic acid when a basic nitrogen is present in the compound of the invention. The salts may also include the acid addition and base salts of the compounds.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of the invention may be prepared by for example, one or more of the following methods:

(i) by reacting the compound of the invention with the desired acid or base;
(ii) by removing an acid- or base-labile protecting group from a suitable precursor of the compound of the invention or by ring-opening a suitable cyclic precursor, for example, a lactone or lactam, using the desired acid or base; or
(iii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised Compounds of the invention i.e. compounds of Formula (I) may in some circumstances exist in a number of different tautomeric forms and references to compounds of the formula I include all such forms.

Compounds that have the same molecular formula but differ in the arrangement of their atoms are termed "isomers".

Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, it is known as a chiral compound. A chiral compound can exist in the form of either one or both of its pair of enantiomers (in the case of a single chiral center). An enantiomer can be characterized by the absolute configuration of its asymmetric centre and is described by the R- and S-sequencing rules of Cahn-Ingold-Prelog. Where there is more than one chiral centre in a molecule then the number of conceivable stereoisomers is $2^n$ where n is the number of chiral centres; the only exception being the existence of symmetry in the molecule leading to a reduction in the number of isomers from the maximum of $2^n$.

The compounds of this invention may possess one or more asymmetric centres; such compounds can therefore be produced as individual (R)- or (S)-stereoisomers or as mixtures thereof.

Some of the compounds of the invention may have geometric isomeric centres (E- and Z-isomers).

It is to be understood that the present invention encompasses all isomeric forms and mixtures thereof that possess metallo-beta-lactamase inhibitory activity.

Methods for the determination of stereochemistry and the separation of stereoisomers are well-known in the art (see discussion in "Advanced Organic Chemistry", 7th edition J. March, John Wiley and Sons, New York, 2013).

Compounds of the Formula I containing an amine function may also form N-oxides. A reference herein to a compound of the Formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid); this is described in general textbooks such as *Advanced Organic Chemistry*, by J. March referred to above. N-oxides can be made in a variety of ways which are known to the skilled person; for example, by reacting the amine compound with m-chloroperoxybenzoic acid (mCPBA) in a solvent such as dichloromethane.

The present invention also encompasses compounds of the invention as defined herein which comprise one or more isotopic substitutions. For example, H may be in any isotopic form, including $^1H$, $^2H$(D), and $^3H$ (T); C may be in any isotopic form, including $^{12}C$, $^{13}C$, and $^{14}C$; and O may be in any isotopic form, including $^{16}O$ and $^{18}O$; and the like. Similarly, isotopic variants of N, S and P may be utilised.

SYNTHESIS AND EXAMPLES

The following compounds represent examples of compounds which can be synthesised in accordance with the invention. Some of the compounds were also tested in a biological assay and the results are presented below. The compounds show activity as inhibitors of metallo-beta-lactamases and thus have utility in the treatment of infections, particularly antibiotic resistant infections.

General Experimental

Microwave assisted reactions were performed using a Biotage Initiator+™ microwave synthesizer in sealed vials.

Throughout this document the following abbreviations have been used:

Bn—benzyl
Boc—tert-butyloxycarbonyl
Cbz—carboxybenzyl
DCM—dichloromethane
DME—1,2-dimethoxyethane
DMF—N,N-dimethylformamide
DMSO—dimethyl sulfoxide
HBTU—N,N,N',N'-tetramethyl-O-(1H-benzotriazol-1-yl)uronium hexafluorophosphate
Hoveyda-Grubbs Catalyst® $2^{nd}$ generation—dichloro[1,3-bis(2,4,6-trimethylphenyl)-2-imidazolidinylidene](2-isopropoxyphenylmethylene)ruthenium(II)
NMP—1-methyl-2-pyrrolidinone
Pd(dppf)$Cl_2$— [1,1'-bis(diphenylphosphino)ferrocene]dichloropalladium(II)
SEM—2-(trimethylsilyl)ethoxymethyl
TFA—trifluoroacetic acid
THF—tetrahydrofuran
XPhos Pd G2—chloro(2-dicyclohexylphosphino-2',4',6'-tri-iso-propyl-1,1'-biphenyl)[2-(2'-amino-1,1'-biphenyl)]palladium(II)

Analytical Methods

All $^1$H and $^{19}$F NMR spectra were obtained on a Bruker AVI 500 with 5 mm QNP. Chemical shifts are expressed in parts per million (δ) and are referenced to the solvent. Coupling constants J are expressed in Hertz (Hz).

LC-MS were obtained on a Waters Alliance ZQ (Methods A, B, C and E) or Waters Acquity H-class UPLC (Method D) using the methods detailed below. Wavelengths were 254 and 210 nm.

Method A

Column: YMC-Triart C18, 2.0×50 mm, 5 μm. Flow rate: 0.8 mL/min. Injection volume: 6 μL Mobile Phase: A=water, B=acetonitrile, C=1:1 water:acetonitrile+1.0% formic acid

| Time | % A | % B | % C |
|---|---|---|---|
| Initial | 90 | 5 | 5 |
| 4.0 | 0 | 95 | 5 |
| 6.0 | 0 | 95 | 5 |

Method B

Column: YMC-Triart C18, 2.0×50 mm, 5 μm. Flow rate: 0.8 mL/min. Injection volume: 6 μL Mobile Phase: A=water, B=acetonitrile, C=1:1 water:acetonitrile+1.0% ammonia (aq.)

| Time | % A | % B | % C |
|---|---|---|---|
| Initial | 90 | 5 | 5 |
| 4.0 | 0 | 95 | 5 |
| 6.0 | 0 | 95 | 5 |

Method C

Column: YMC-Triart C18, 2.0×50 mm, 5 μm. Flow rate: 0.8 mL/min. Injection volume: 6 μL Mobile Phase: A=water, B=acetonitrile, C=1:1 water:acetonitrile+1.0% formic acid

| Time | % A | % B | % C |
|---|---|---|---|
| Initial | 95 | 0 | 5 |
| 2.0 | 95 | 0 | 5 |
| 12.0 | 0 | 95 | 5 |
| 14.0 | 0 | 95 | 5 |

Method D

Column: CSH C18, 2.1×100 mm, 1.7 μm. Flow rate: 0.6 mL/min. Injection volume: 5 μL Mobile Phase: A=water+0.1% formic acid, B=acetonitrile+0.1% formic acid

| Time | % A | % B |
|---|---|---|
| Initial | 98 | 2 |
| 0.5 | 98 | 2 |
| 6.5 | 2 | 98 |
| 7.5 | 2 | 98 |

Method E

Column: YMC-Triart C18, 2.0×50 mm, 5 μm. Flow rate: 0.8 mL/min. Injection volume: 6 μL Mobile Phase: A=water, B=acetonitrile, C=1:1 water:acetonitrile+1.0% ammonia (aq.)

| Time | % A | % B | % C |
|---|---|---|---|
| Initial | 97.5 | 0 | 2.5 |
| 3.0 | 0 | 95 | 5 |
| 5.0 | 0 | 95 | 5 |

Preparative HPLC chromatography was carried out using a Waters Auto Lynx Mass Directed Fraction Collector using the methods detailed below.

Method A

Column: CSH C18, 30×100 mm, 5 μm. Flow rate: 80 mL/min. Injection volume: 2500 μL.

Run Time: 6.5 minutes (gradient range below) then 1.25 minutes 95% (% B in A).

Mobile Phase A=water+0.1% formic acid, B=acetonitrile+0.1% formic acid

| Method Name | Gradient Range (% B in A) |
|---|---|
| 0.60-0.80 min. | 2-12% |
| 0.80-1.00 min. | 5-15% |
| 1.00-1.11 min. | 8-18% |
| 1.22-1.33 min. | 15-25% |
| 1.78-1.90 min. | 40-50% |

Intermediate 1: [(Benzyloxy)carbonyl]({[4-(dimethyliminiumyl)-1,4-dihydropyridin-1-yl]sulfonyl})azanide

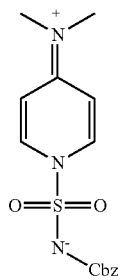

A solution of benzyl alcohol (12.0 mL, 116 mmol) in DCM (200 mL) was cooled to 0° C. followed by the dropwise addition of chlorosulfonyl isocyanate (10.0 mL, 115 mmol). After stirring at 0° C. for 10 minutes, 4-(dimethylamino)pyridine (28.0 g, 230 mmol) was added portionwise and the reaction mixture allowed to warm to room temperature and stirred overnight. The resulting mixture was diluted with DCM (200 mL), washed with water (3×200 mL), dried over MgSO$_4$, filtered and concentrated to dryness under reduced pressure to give the desired product as a white solid (33.9 g, 96%).

$^1$H NMR (500 MHz, DMSO-d$_6$) δ 8.44-8.52 (m, 2H), 7.28-7.37 (m, 3H), 7.24-7.27 (m, 2H), 6.93-6.97 (m, 2H), 4.87 (s, 2H), 3.23 (s, 6H).

LC-MS (Method A): R$_T$=2.54 min, m/z=336.0 [M+H]$^+$.

Intermediate 2: tert-Butoxycarbonyl-[(4-dimethyliminio-1-pyridyl)sulfonyl]azanide

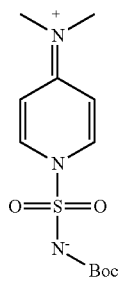

A solution of tert-butyl alcohol (4.41 mL, 46.1 mmol) in DCM (100 mL) was cooled to 0° C. followed by the dropwise addition of chlorosulfonyl isocyanate (4.0 mL, 46.1 mmol). After stirring at 0° C. for 10 minutes, 4-(dimethylamino)pyridine (11.3 g, 92.1 mmol) was added portionwise and the reaction mixture allowed to warm to room temperature and stirred overnight. The resulting mixture was diluted with DCM (100 mL), washed with water (3×100 mL), dried over MgSO$_4$, filtered and concentrated to dryness under reduced pressure to give the desired product as a white solid (7.32 g, 53%).

$^1$H NMR (500 MHz, DMSO-d$_6$) δ 8.42-8.48 (m, 2H), 7.03-7.09 (m, 2H), 3.22 (s, 6H), 1.26 (s, 9H).

LC-MS (Method A): R$_T$=2.10 min, m/z=302.1 [M+H]$^+$.

Intermediate 3: Sodium [(benzyloxy)carbonyl]({2-[(benzyloxy)carbonyl]-3-bromo-1H-pyrrol-1-yl}sulfonyl)azanide

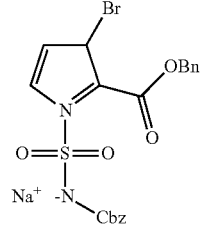

Step A: Benzyl 1-(benzenesulfonyl)-3-bromo-1H-pyrrole-2-carboxylate

A solution of diisopropylamine (11.7 mL, 83.5 mmol) in anhydrous THF (150 mL) was cooled to −78° C. followed by the dropwise addition of a solution of n-butyllithium (2.5 M in hexanes, 26.7 mL, 66.8 mmol). The reaction mixture was stirred at −78° C. for 10 minutes, allowed to warm to −10° C. then cooled immediately to −78° C. A solution of 1-(benzenesulfonyl)-3-bromo-1H-pyrrole (15.9 g, 55.6 mmol) in anhydrous THF (50 mL) was then added dropwise. After stirring at −78° C. for 1 hour, a solution of benzyl chloroformate (14.3 mL, 100 mmol) in anhydrous THF (50 mL) was added dropwise over a period of 90 minutes and the mixture stirred at −78° C. for a further 1 hour. The reaction mixture was then quenched by the dropwise addition of saturated ammonium chloride solution (50 mL) before allowing to warm to room temperature. After diluting the mixture with further saturated ammonium chloride solution (100 mL), the product was extracted into ethyl acetate (3×100 mL). The combined organic phases were washed with water (2×100 mL), brine (100 mL), dried over MgSO$_4$, filtered and concentrated to dryness under reduced pressure. The residue was purified by column chromatography (silica, petroleum ether:ethyl acetate, gradient elution from 100:0 to 70:30) to give the desired product as an orange oil (14.4 g, 62%).

Further material was isolated by repurification of mixed fractions that ran straight off the first column by column chromatography (silica, petroleum ether:ethyl acetate, gradient elution from 100:0 to 70:30) to give the desired product as a colourless oil (5.84 g, 25%).

$^1$H NMR (500 MHz, CHLOROFORM-d) δ 7.88-7.92 (m, 2H), 7.59-7.64 (m, 1H), 7.56 (d, J=3.47 Hz, 1H), 7.46-7.51 (m, 2H), 7.32-7.40 (m, 5H), 6.39-6.42 (m, 1H), 5.27 (s, 2H).

LC-MS (Method A): R$_T$=4.03 min, m/z=419.9/421.9 [M+H]$^+$.

Step B: Benzyl 3-bromo-1H-pyrrole-2-carboxylate

To a solution of benzyl 1-(benzenesulfonyl)-3-bromo-1H-pyrrole-2-carboxylate (20.2 g, 48.1 mmol) in anhydrous THF (150 mL) was added a solution of tetrabutylammonium fluoride (1 M in THF, 57.7 mL, 57.7 mmol) dropwise, followed by stirring at room temperature for 2 hours. The reaction mixture was quenched by the addition of water (200 mL) and extracted into ethyl acetate (3×150 mL). The combined organic phases were washed with water (2×200 mL), brine (200 mL), dried over MgSO$_4$, filtered and concentrated to dryness under reduced pressure. The residue was purified by column chromatography (silica, petroleum ether:ethyl acetate, gradient elution from 100:0 to 70:30) followed by column chromatography (silica, petroleum ether:DCM, gradient elution from 90:10 to 0:100) followed by column chromatography (silica, petroleum ether:THF, gradient elution from 100:0 to 70:30) to give the desired product as a colourless oil that solidified upon standing (10.27 g, 76%).

$^1$H NMR (500 MHz, CHLOROFORM-d) δ 9.31 (br s, 1H), 7.45-7.48 (m, 2H), 7.32-7.40 (m, 3H), 6.84 (t, J=3.15 Hz, 1H), 6.34 (t, J=2.84 Hz, 1H), 5.35 (s, 2H).

LC-MS (Method A): $R_T$=3.52 min, m/z=278.1/280.1 [M−H]$^-$.

Step C: Sodium [(benzyloxy)carbonyl]({2-[(benzyloxy)carbonyl]-3-bromo-1H-pyrrol-1-yl}sulfonyl)azanide A solution of benzyl 3-bromo-1H-pyrrole-2-carboxylate (10.27 g, 36.7 mmol) in anhydrous THF (100 mL) was cooled to 0° C. under a nitrogen atmosphere followed by the portionwise addition of sodium hydride (60% in mineral oil, 2.20 g, 55.0 mmol). After stirring at 0° C. for minutes, [(benzyloxy)carbonyl]({[4-(dimethyliminiumyl)-1,4-dihydropyridin-1-yl]sulfonyl})azanide (13.5 g, 40.3 mmol) was added and the reaction mixture heated to reflux for 4 hours. After cooling to 0° C., the reaction was quenched by the dropwise addition of water (100 mL), concentrated under reduced pressure to remove organic solvents and extracted into ethyl acetate (3×100 mL). The combined organic phases were washed with brine (100 mL), dried over MgSO$_4$, filtered and concentrated to dryness under reduced pressure. The residue was purified by column chromatography (silica, petroleum ether:ethyl acetate:methanol, gradient elution from 50:50:0 to 0:100:0 to 0:90:10) to give the desired product as a tan solid (10.5 g, 56%).

$^1$H NMR (500 MHz, DMSO-d$_6$) δ 7.51-7.56 (m, 2H), 7.26-7.35 (m, 9H), 6.18 (d, J=3.15 Hz, 1H), 5.22 (s, 2H), 4.85 (s, 2H).

LC-MS (Method A): $R_T$=3.31 min, m/z=491.0/493.0 [M−H]$^-$.

Intermediate 4: Benzyl-3-(4-piperidyl)-1H-pyrrole-2-carboxylate Hydrochloride

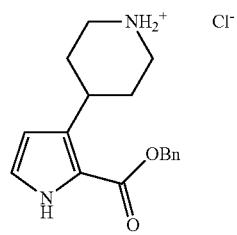 [SMILES: O=C(OCc1ccccc1)c1[nH]ccc1C1CC[NH2+]CC1 ; [Cl-]]

Step A: tert-Butyl 4-(2-benzyloxycarbonyl-1H-pyrrol-3-yl)piperidine-1-carboxylate To a solution of tert-butyl 4-ethynylpiperidine-1-carboxylate (422 μL, 4.78 mmol) and benzyl 2-isocyanoacetate (1.26 g, 7.17 mmol) in anhydrous NMP (10 mL) under argon was added silver carbonate (132 mg, 478 μmol) and the reaction heated at 80° C. for 5 hours. The reaction mixture was filtered through Celite®, diluted with water (100 mL) and extracted with diethyl ether (2×50 mL) then ethyl acetate (50 mL). The combined organics were washed with water (2×50 mL), brine (50 mL), dried over MgSO$_4$, filtered and concentrated to dryness under reduced pressure. The residue was purified by column chromatography (silica, petroleum ether:ethyl acetate, gradient elution from 100:0 to 75:25) to give the desired product as a colourless gum (740 mg, 40%).

$^1$H NMR (500 MHz, CDCl$_3$) δ 8.97 (s, 1H), 7.30-7.40 (m, 5H), 6.85 (t, J=2.8 Hz, 1H), 6.15 (t, J=2.8 Hz, 1H), 5.29 (s, 2H), 4.10-4.20 (m, 2H), 3.32 (s, 1H), 2.60-2.80 (m, 2H), 1.81 (br d, J=12.6 Hz, 2H), 1.50-1.60 (m, 2H), 1.50 (s, 9H).

LC-MS (Method A): $R_T$=3.95 min, m/z=385.2 [M+H]$^+$

Step B: Benzyl-3-(4-piperidyl)-1H-pyrrole-2-carboxylate Hydrochloride

4M HCl in 1,4-dioxane (4.72 mL, 18.9 mmol) was added to a solution of tert-butyl 4-(2-benzyloxycarbonyl-1H-pyrrol-3-yl)piperidine-1-carboxylate (850 mg, 2.21 mmol) in DCM (5 mL, with a few drops of methanol) at room temperature. After 18 hours all volatiles were removed under reduced pressure to give the desired product as a white solid (697 mg, 98%).

$^1$H NMR (500 MHz, DMSO-d6) δ=11.73 (br s, 1H), 8.87 (br s, 1H), 8.71 (br s, 1H), 7.49-7.30 (m, 5H), 6.94 (t, J=2.4 Hz, 1H), 6.10 (t, J=2.4 Hz, 1H), 5.28 (s, 2H), 3.35-3.24 (m, 3H), 2.88-2.75 (m, 2H), 1.94-1.83 (m, 2H), 1.81-1.67 (m, 2H).

LC-MS (Method A): RT=2.25 min, m/z=285.2 [M+H]$^+$.

Intermediate 5: Benzyl-1-(benzyloxycarbonylsulfamoyl)-3-(4-piperidyl)pyrrole-2-carboxylate Hydrochloride

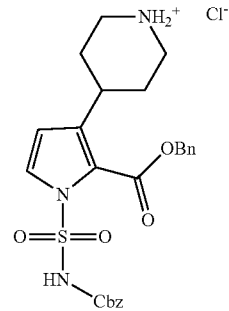 [SMILES: [Cl-] ; O=C(NS(=O)(=O)n1ccc(C2CC[NH2+]CC2)c1C(=O)OCc1ccccc1)OCc1ccccc1]

Step A: tert-Butyl-4-[2-benzyloxycarbonyl-1-(benzyloxycarbonylsulfamoyl)pyrrol-3-yl]piperidine-1-carboxylate, Sodium Salt Sodium hydride (60% in mineral oil, 2.34 g, 48.9 mmol) was added to THF (50 mL) and cooled to −10° C. under nitrogen. Once cooled, tert-butyl 4-(2-benzyloxycarbonyl-1H-pyrrol-3-yl)piperidine-1-carboxylate (6.26 g, 16.3 mmol) dissolved in THF (30 mL) was slowly added to the mixture. Once addition was complete the reaction was allowed to warm up to room temperature and stirred for 30 minutes before being cooled to −10° C. Benzyl N-chlorosulfonylcarbamate (4.47 g, 17.9 mmol) was added portionwise maintaining the temperature at −10° C. Once the addition was complete the mixture was stirred at −10° C. for 1 hour, allowed to warm to room temperature and stirred for a further 1 hour. The reaction was carefully quenched with water (40 mL) and brine (40 mL), extracted with ethyl acetate (2×150 mL), dried over MgSO$_4$, filtered and solvent evaporated until approximately 10 mL of ethyl acetate was remaining. The mixture was diluted with diethyl ether (100 mL) to afford a solid which was stirred for 10 minutes before being filtered to afford the desired product as a brown solid (4.6 g, 38%). This was used in the subsequent step without further purification.

LC-MS (Method B): RT=3.24 min, m/z=596.5 [M−H]$^-$.

Step B: Benzyl-1-(benzyloxycarbonylsulfamoyl)-3-(4-piperidyl)pyrrole-2-carboxylate hydrochloride tert-Butyl-4-[2-benzyloxycarbonyl-1-(benzyloxycarbonylsulfamoyl)pyrrol-3-yl]piperidine-1-carboxylate, sodium salt (4.6 g, 7.70 mmol) was added to 4M HCl in 1,4-dioxane (20 mL) and stirred for 3 hours. The mixture was diluted with 1,4-dioxane (20 mL) and filtered. The filtrate was then diluted with diethyl ether to afford a solid which was dried by vacuum filtration whilst blanketed with a stream of nitrogen to afford the desired product as a yellow solid (3.70 g, 81%).

$^1$H NMR (500 MHz, DMSO-d6) δ 8.65 (br s, 1H), 8.40 (br s, 1H), 7.50 (br d, J=6.9 Hz, 2H), 7.3-7.4 (m, 9H), 6.12 (br s, 1H), 5.27 (s, 2H), 5.00 (s, 2H), 3.3-3.2 (m, 2H), 3.1-3.0 (m, 1H), 2.7-2.6 (m, 2H), 1.8-1.6 (m, 4H).

LC-MS (Method B): RT=3.24 min, m/z=498.2 [M+H]$^+$.

Intermediate 6: Sodium {[3-bromo-2-(1-{[2-(trimethylsilyl)ethoxy]methyl}-1H-tetrazol-5-yl)-1H-pyrrol-1-yl]sulfonyl}[(tert-butoxy)carbonyl]azanide and sodium {[3-bromo-2-(2-{[2-(trimethylsilyl)ethoxy]methyl}-2H-tetrazol-5-yl)-1H-pyrrol-1-yl]sulfonyl}[(tert-butoxy)carbonyl]azanide

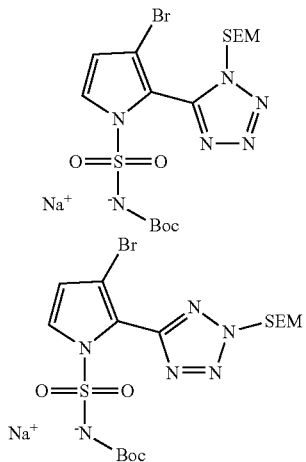

Step A: 5-(3-Bromo-1H-pyrrol-2-yl)-1H-tetrazole

Sodium azide (1.08 g, 16.6 mmol) was added to a mixture of 3-bromo-1H-pyrrole-2-carbonitrile (1.42 g, 8.3 mmol) and zinc chloride (570 mg, 4.2 mmol) in propan-2-ol (20 mL) and water (40 mL) and the resulting solution heated at 100° C. for 17 hours under nitrogen. The reaction mixture was cooled to room temperature, recharged with sodium azide (1.08 g, 16.6 mmol) and heated at 100° C. for a further 17 hours. The reaction mixture was recharged with sodium azide (1.08 g, 16.6 mmol) and heated at 100° C. for a further 20 hours. The reaction mixture was recharged with sodium azide (500 mg, 8.0 mmol) and heated at 100° C. for a further 20 hours. The reaction mixture was allowed to cool to room temperature and quenched carefully with a solution containing a mixture of sodium hydroxide (8.36 g) and sodium nitrite (11.04 g) in water (80 mL). The resulting solution was extracted with diethyl ether (2×50 mL). The aqueous layer was collected, diluted with ethyl acetate (60 mL), cooled to 0° C. and acidified with the dropwise addition of 6M HCl$_{(aq)}$ (pH 14 to pH 1). The resulting solution was stirred for 30 minutes and the resulting layers separated. The aqueous layer was further extracted with ethyl acetate (2×40 mL). The organic extracts were combined with the original organic layer, dried over MgSO$_4$ and filtered. DMF (30 mL) was added to the filtrate and ethyl acetate removed under reduced pressure to afford the desired product as a solution in DMF. The product was used directly in the next step without further purification.

LC-MS (Method E): R$_T$=1.19 min, m/z=212.1/214.1 [M−H]$^-$.

Step B: 5-(3-Bromo-1H-pyrrol-2-yl)-1-{[2-(trimethylsilyl)ethoxy]methyl}-1H-tetrazole and 5-(3-bromo-1H-pyrrol-2-yl)-2-{[2-(trimethylsilyl)ethoxy]methyl}-2H-tetrazole Potassium carbonate (5.04 g, 36.8 mmol) and 2-(choromethoxyethyl)trimethyl silane (2.19 mL, 12.5 mmol) were added to a solution of 5-(3-bromo-1H-pyrrol-2-yl)-1H-tetrazole (1.78 g, 8.3 mmol, assumed quantitative yield from Step A) in DMF (30 mL) and stirred for 2 hours at room temperature under nitrogen. The reaction mixture was quenched with water (60 mL) and the aqueous layer extracted with ethyl acetate (4×50 mL). The combined extracts were washed with a 1:1 solution of brine and water (2×50 mL), dried over MgSO$_4$ filtered and concentrated under reduced pressure to afford crude material. The crude product was purified by column chromatography (silica, gradient of 0-20% ethyl acetate/petroleum ether) to afford the desired product as a mixture of isomers (1.08 mg, 38%).

LC-MS (Method A): R$_T$=3.44 min, m/z=342.1/344.1 [M−H]$^-$ and R$_T$=3.58 min, m/z=342.1/344.1 [M−H]$^-$.

Step C: Sodium {[3-bromo-2-(1-{[2-(trimethylsilyl)ethoxy]methyl}-1H-tetrazol-5-yl)-1H-pyrrol-1-yl]sulfonyl}[(tert-butoxy)carbonyl]azanide and sodium {[3-bromo-2-(2-{[2-(trimethylsilyl)ethoxy]methyl}-2H-tetrazol-5-yl)-1H-pyrrol-1-yl]sulfonyl}[(tert-butoxy)carbonyl]azanide Sodium hydride (60% in mineral oil, 109 mg, 2.7 mmol) was added to a solution of 5-(3-bromo-1H-pyrrol-2-yl)-1-{[2-(trimethylsilyl)ethoxy]methyl}-1H-tetrazole and 5-(3-bromo-1H-pyrrol-2-yl)-2-{[2-(trimethylsilyl)ethoxy]methyl}-2H-tetrazole (625 mg, 1.82 mmol) in anhydrous THF (20 mL) and allowed to stir for 1 hour at room temperature under nitrogen. tert-Butoxycarbonyl-[(4-dimethyliminio-1-pyridyl)sulfonyl]azanide (657 mg, 2.18 mmol) was added to the reaction mixture and heated to 70° C. for 20 hours. The reaction mixture was allowed to cool to room temperature, quenched with water (10 mL) and volatile organics removed under reduced pressure. The remaining aqueous solution was extracted with ethyl acetate (3×30 mL) and the combined extracts dried over MgSO$_4$, filtered and concentrated under reduced pressure to afford crude material. The crude product was purified by column chromatography (silica, gradient of 5-100% ethyl acetate/petroleum ether then 0-20% methanol/ethyl acetate) to give the desired product mixture as an off-white solid (514 mg, 52%).

LC-MS (Method A): R$_T$=3.29 min, m/z=521.1/523.1 [M−H]$^−$ and R$_T$=3.90 min, m/z=521.1/523.1 [M−H]$^−$.

Intermediate 7: tert-Butyl 3-(tert-butylsulfamoyl)-pyrrole-2-carboxylate

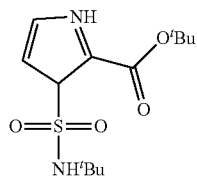

Step A: 1-(Benzenesulfonyl)pyrrole-2-sulfonyl chloride

A solution of 1-(benzenesulfonyl)pyrrole (10 g, 48.3 mmol) in acetonitrile (100 mL) was cooled to 0° C. followed by the dropwise addition of chlorosulfonic acid (6.43 mL, 96.5 mmol). The resulting solution was allowed to warm to room temperature and stirred overnight. Thionyl chloride (3.87 mL, 53.1 mmol) was added dropwise followed by heating to reflux for 2 hours. Additional thionyl chloride (704 μL, 9.65 mmol) was added followed by heating at reflux for a further 1 hour. After allowing to cool to room temperature the reaction mixture was quenched by the cautious addition to ice (500 g). The precipitated solid was isolated by vacuum filtration on a sintered funnel, washed with water and dried under vacuum to give the desired product as a dark brown solid (12.1 g, 82%).

$^1$H NMR (500 MHz, DMSO-d$_6$) δ 8.0-8.0 (m, 2H), 7.7-7.8 (m, 1H), 7.6-7.7 (m, 2H), 7.26 (dd, J=2.4, 3.3 Hz, 1H), 7.17 (dd, J=1.6, 2.5 Hz, 1H), 6.31 (dd, J=1.6, 3.2 Hz, 1H).

LC-MS (Method A): R$_T$=3.51 min, m/z=304.1/306.1 [M−H]$^−$.

Step B: N-tert-butyl-1H-pyrrole-2-sulfonamide

To a solution of 1-(benzenesulfonyl)pyrrole-2-sulfonyl chloride (12.1 g, 39.6 mmol) in THF (40 mL) was added tert-butylamine (10.4 mL, 98.9 mmol) followed by stirring at room temperature for 1 hour. The reaction mixture was then diluted with water (80 mL) followed by the addition of lithium hydroxide monohydrate (4.15 g, 98.9 mmol) and heating to 70° C. for 2 hours. The reaction mixture was then cooled to 0° C., acidified with 2M HCl$_{(aq)}$ and partitioned with ethyl acetate (100 mL). The biphasic mixture was filtered through Celite®, the layers separated and the aqueous phase extracted with ethyl acetate (2×100 mL). The combined organic phases were washed with brine (100 mL), dried over MgSO$_4$ and concentrated to dryness under reduced pressure to give the desired product as a brown solid (6.12 g, 76%).

$^1$H NMR (500 MHz, DMSO-d$_6$) δ 11.35 (br s, 1H), 7.2-7.2 (m, 1H), 6.85 (s, 1H), 6.8-6.8 (m, 1H), 6.29 (dt, J=1.6, 2.7 Hz, 1H), 1.09 (s, 9H).

LC-MS (Method A): R$_T$=2.05 min, m/z=201.3 [M−H]$^−$.

Step C: 1-Benzyl-N-tert-butyl-pyrrole-2-sulfonamide

A solution of N-tert-butyl-1H-pyrrole-2-sulfonamide (3.0 g, 14.8 mmol) in anhydrous THF (30 mL) was cooled to 0° C. followed by the addition of sodium hydride (60% in mineral oil, 712 mg, 17.80 mmol). After stirring at 0° C. for 5 minutes, benzyl bromide (2.64 mL, 22.3 mmol) was added before allowing to warm to room temperature over 2 hours. After cooling to 0° C., the mixture was quenched by the dropwise addition of saturated ammonium chloride solution (50 mL) and the product extracted into ethyl acetate (3×50 mL). The combined organic phases were washed with brine (50 mL), dried over MgSO$_4$, filtered and concentrated to dryness under reduced pressure. The residue was triturated with diethyl ether (40 mL) and the solid isolated and dried by vacuum filtration to give the desired product as a tan solid (2.92 g, 67%).

$^1$H NMR (500 MHz, CHLOROFORM-d) δ 7.3-7.4 (m, 3H), 7.18 (t, J=2.0 Hz, 1H), 7.1-7.1 (m, 2H), 6.6-6.7 (m, 1H), 6.45 (dd, J=1.7, 3.0 Hz, 1H), 5.05 (s, 2H), 4.29 (s, 1H), 1.26 (s, 9H).

LC-MS (Method A): R$_T$=3.26 min, m/z=291.3 [M−H]$^−$.

Step D: tert-Butyl 1-benzyl-3-(tert-butylsulfamoyl) pyrrole-2-carboxylate

A solution of 1-benzyl-N-tert-butyl-pyrrole-2-sulfonamide (2.92 g, 10.0 mmol) in anhydrous THF (60 mL) was cooled to −78° C. under a nitrogen atmosphere followed by the dropwise addition of n-butyllithium solution (2.5M in hexanes, 9.99 mL, 25.0 mmol). After stirring at −78° C. for 30 minutes, a solution of di-tert-butyl dicarbonate (2.75 mL, 12.0 mmol) in anhydrous THF (20 mL) was added dropwise. The reaction mixture was stirred at −78° C. for 4 hours then quenched by the dropwise addition of ammonium chloride solution (50 mL) and extracted into ethyl acetate (3×50 mL). The combined organic phases were dried over MgSO$_4$, filtered and concentrated to dryness under reduced pressure. The residue was purified by column chromatography (silica, petroleum ether:ethyl acetate, gradient elution from 100:0 to 60:40) to give the desired product as an off-white solid (2.93 g, 75%).

$^1$H NMR (500 MHz, CHLOROFORM-d) δ 7.3-7.3 (m, 3H), 6.9-7.0 (m, 2H), 6.74 (d, J=2.8 Hz, 1H), 6.72 (d, J=2.8 Hz, 1H), 5.79 (s, 1H), 5.47 (s, 2H), 1.43 (s, 9H), 1.24 (s, 9H).

LC-MS (Method A): R$_T$=3.87 min, m/z=391.3 [M−H]$^−$.

Step E: tert-Butyl 3-(tert-butylsulfamoyl)-1H-pyrrole-2-carboxylate

To a suspension of tert-butyl 1-benzyl-3-(tert-butylsulfamoyl)pyrrole-2-carboxylate (500 mg, 1.27 mmol), 20% palladium hydroxide on carbon (179 mg, 127 μmol) and 10% palladium on carbon (50% wet, 136 mg, 64 μmol) in ethanol (20 mL) was added ammonium formate (803 mg, 12.7 mmol) followed by heating to 50° C. under a nitrogen atmosphere for 1 hour, then to reflux for 3 hours. Further ammonium formate (803 mg, 12.7 mmol) was added followed by heating to reflux overnight. Further 20% palladium hydroxide on carbon (179 mg, 127 μmol), 10% palladium on carbon (50% wet, 136 mg, 63.69 μmol) and ammonium formate (803 mg, 12.7 mmol) were added followed by heating to reflux overnight. The reaction mixture was then allowed to cool to room temperature, filtered through Celite® and concentrated to dryness under reduced pressure. The residue was redissolved in DCM (10 mL), washed with water (10 mL), dried over MgSO$_4$, filtered and concentrated to dryness. The residue was purified by column chromatography (silica, petroleum ether:ethyl acetate, gradient elution from 100:0 to 40:60) to give the desired product as an off-white solid (200 mg, 52%).

$^1$H NMR (500 MHz, CHLOROFORM-d) δ 9.21 (br s, 1H), 6.83 (t, J=2.9 Hz, 1H), 6.75 (t, J=2.9 Hz, 1H), 5.91 (s, 1H), 1.61 (s, 9H), 1.22 (s, 9H).

LC-MS (Method A): R$_T$=3.29 min, m/z=301.3 [M−H]$^−$.

Intermediate 8: 1-Methyl-N-[4-(4,4,5,5-tetramethyl-1,3,2-dioxaborolan-2-yl)phenyl]-1H-imidazole-4-sulfonamide

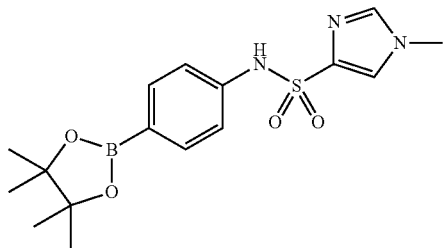

To a solution of 4-(4,4,5,5-tetramethyl-1,3,2-dioxaborolan-2-yl)aniline (500 mg, 2.28 mmol) and pyridine (369 μL, 4.56 mmol) in DCM (20 mL) at 0° C. was added 1-methyl-1H-imidazole-4-sulfonyl chloride (453 mg, 2.51 mmol) and the reaction was allowed to stir for 18 hours. The reaction mixture was diluted with DCM (50 mL), washed with water (50 mL), brine (50 mL), dried over MgSO$_4$, filtered and concentrated to dryness. The residue was triturated with diethyl ether and the solid isolated by filtration to give the desired product as a pale pink solid (677 mg, 82%).

$^1$H NMR (500 MHz, DMSO-d$_6$) δ 10.46 (s, 1H), 7.88 (s, 1H), 7.73 (s, 1H), 7.53-7.48 (m, 2H), 7.18-7.13 (m, 2H), 3.65 (s, 3H), 1.26 (s, 12H).

LC-MS (Method B): R$_T$=2.16 min, m/z=364.2 [M+H]$^+$.

Intermediate 9: tert-Butyl-N-(2-{[4-(4,4,5,5-tetramethyl-1,3,2-dioxaborolan-2-yl)phenyl]sulfamoyl}ethyl)carbamate

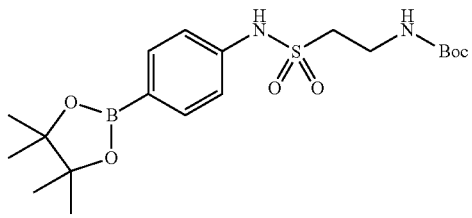 [SMILES: CC(C)(C)OC(=O)NCCS(=O)(=O)Nc1ccc(B2OC(C)(C)C(C)(C)O2)cc1]

Step A: N-(4-Bromophenyl)-2-(1,3-dioxo-2,3-dihydro-1H-isoindol-2-yl)ethane-1-sulfonamide To a solution of 4-bromoaniline (1.05 g, 6.12 mmol) in chloroform (10 mL) was added 2-(1,3-dioxo-2,3-dihydro-1H-isoindol-2-yl)ethane-1-sulfonyl chloride (500 mg, 1.83 mmol) portionwise and the reaction was allowed to stir at room temperature for 3 days. To the reaction mixture was added pyridine (148 μL, 1.83 mmol) and stirred for a further 24 hours. The reaction mixture was diluted with DCM (50 mL), washed with water (50 mL), 2M HCl$_{(aq)}$ (50 mL), brine (50 mL), dried over MgSO$_4$, filtered and concentrated to dryness. The residue was recrystallised from ethanol, filtered and washed with petroleum ether to give the desired product as cream crystals (534 mg, 71%).

$^1$H NMR (500 MHz, CDCl$_3$) δ 7.86 (dd, J=3.1, 5.3 Hz, 2H), 7.76 (dd, J=3.1, 5.3 Hz, 2H), 7.44 (d, J=8.7 Hz, 2H), 7.25-7.17 (m, 3H), 4.07 (t, J=5.9 Hz, 2H), 3.46 (t, J=5.9 Hz, 2H).

LC-MS (Method B): R$_T$=2.58 min, m/z=407.1/409.1 [M−H]$^−$.

Step B: tert-Butyl N-{2-[(4-bromophenyl)sulfamoyl]ethyl}carbamate

To a solution of N-(4-bromophenyl)-2-(1,3-dioxo-2,3-dihydro-1H-isoindol-2-yl)ethane-1-sulfonamide (534 mg, 1.30 mmol) in ethanol (10 mL) at 80° C. was added hydrazine hydrate (140 μL, 1.44 mmol) and the reaction was stirred at 80° C. for 4 hours. The solid was removed by filtration and washed with ethanol. The filtrates were concentrated to dryness and the residue suspended in DCM (30 mL) before addition of di-tert-butyl dicarbonate (344 μL, 1.50 mmol) and stirring at 20° C. for 2 days. The reaction mixture was concentrated to dryness and purified by column chromatography (silica, petroleum ether:ethyl acetate, gradient elution from 100:0 to 50:50) to give the desired product as a white solid (412 mg, 84%).

$^1$H NMR (500 MHz, CDCl$_3$) δ 7.48-7.40 (m, 3H), 7.19 (br d, J=8.4 Hz, 2H), 5.04 (br s, 1H), 3.60 (q, J=5.8 Hz, 2H), 3.26-3.19 (m, 2H), 1.45 (s, 9H).

LC-MS (Method B): R$_T$=2.83 min, m/z=377.2/379.2 [M−H]$^−$.

Step C: tert-Butyl-N-(2-{[4-(4,4,5,5-tetramethyl-1,3,2-dioxaborolan-2-yl)phenyl]sulfamoyl}ethyl)carbamate A solution of tert-butyl N-{2-[(4-bromophenyl)sulfamoyl]ethyl}carbamate (254 mg, 670 μmol), bis(pinacolato)diboron (340 mg, 1.34 mmol) and potassium acetate (197 mg, 2.01 mmol) in anhydrous 1,4-dioxane (20 mL) was stirred under argon for 10 minutes before addition of Pd(dppf)Cl$_2$ (24.5 mg, 33.5 μmol). The reaction mixture was heated at 85° C. for 18 hours, then diluted with ethyl acetate (50 mL) and water (50 mL) and filtered through Celite®. The filtrate was separated and the aqueous layer extracted with ethyl acetate (50 mL). The combined organics were washed with water (50 mL), brine (50 mL), dried over MgSO$_4$, filtered, concentrated to dryness and purified by column chromatography (silica, petroleum ether:ethyl acetate, gradient elution from 100:0 to 60:40) to give the crude product as a clear gum (364 mg crude yield).

$^1$H NMR (500 MHz, CDCl$_3$) δ 7.78 (d, J=8.4 Hz, 2H), 7.25-7.16 (m, 3H), 5.04 (brt, J=6.1 Hz, 1H), 3.58 (br d, J=4.9 Hz, 2H), 3.29-3.19 (m, 2H), 1.44 (s, 9H), 1.34 (s, 12H).

LC-MS (Method B): R$_T$=3.29 min, m/z=425.4 [M−H]$^−$.

Intermediate 10: tert-Butyl N-[(tert-butoxy)carbonyl]-N-[1-methyl-4-(4,4,5,5-tetramethyl-1,3,2-dioxaborolan-2-yl)-1H-1,3-benzodiazol-2-yl]carbamate

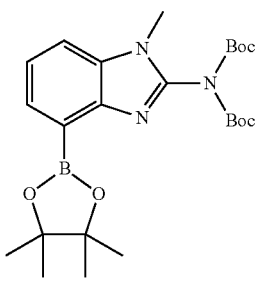 [SMILES: Cn1c(N(C(=O)OC(C)(C)C)C(=O)OC(C)(C)C)nc2c(B3OC(C)(C)C(C)(C)O3)cccc21]

Step A: tert-butyl N-(4-bromo-1-methyl-benzimidazol-2-yl)-N-tert-butoxycarbonyl carbamate To a stirred suspension of 4-bromo-1-methyl-1H-1,3-benzodiazol-2-amine (725 mg, 3.21 mmol) in DCM (10 mL) was added triethylamine (447 µL, 3.21 mmol) and di-tert-butyl dicarbonate (1.54 g, 7.06 mmol). After effervescence ceased, the reaction mixture was diluted with diethyl ether (10 mL) and washed with water (3×10 mL). The organic extract was dried over Na$_2$SO$_4$, filtered, concentrated to dryness and triturated with petroleum ether to give the desired product as an off-white solid (1.12 g, 81%).

$^1$H NMR (500 MHz, CDCl$_3$) δ 7.48 (d, J=7.8 Hz, 1H), 7.30 (d, J=7.6 Hz, 1H), 7.19 (t, J=7.9 Hz, 1H), 3.64 (s, 3H), 1.42 (s, 18H).

Step B: tert-Butyl N-[(tert-butoxy)carbonyl]-N-[1-methyl-4-(4,4,5,5-tetramethyl-1,3,2-dioxaborolan-2-yl)-1H-1,3-benzodiazol-2-yl]carbamate A solution of tert-butyl N-(4-bromo-1-methyl-benzimidazol-2-yl)-N-tert-butoxycarbonyl carbamate (388 mg, 910 µmol), bis(pinacolato)diboron (347 mg, 1.37 mmol), potassium acetate (268 mg, 2.73 mmol) and Pd(dppf)Cl$_2$ (40 mg, 55 µmol) in DME (4 mL) under a nitrogen atmosphere was heated at 90° C. by microwave irradiation for 8 hours. The reaction was recharged with further Pd(dppf)Cl$_2$ (40 mg, 55 µmol) and bis(pinacolato)diboron (347 mg, 1.37 mmol) and heated for a further 2 hours. The reaction mixture was concentrated under reduced pressure, suspended in diethyl ether and filtered through Celite®. The filtrate was evaporated to dryness then purified by column chromatography (silica, petroleum ether:ethyl acetate, gradient elution from 100:0 to 70:30) to give the desired product as a white solid (272 mg, 63%).

$^1$H NMR (500 MHz, CDCl$_3$) δ=7.80 (dd, J=7.3, 1.0 Hz, 1H), 7.42 (dd, J=8.1, 1.0 Hz, 1H), 7.31 (dd, J=8.1, 7.3 Hz, 1H), 3.62 (s, 3H), 1.42 (s, 18H), 1.39 (s, 12H).

Intermediate 11: tert-Butyl N-tert-butoxycarbonyl-N-[6-(4,4,5,5-tetramethyl-1,3,2-dioxaborolan-2-yl)-[1,2,4]triazolo[1,5-a]pyridin-2-yl]carbamate

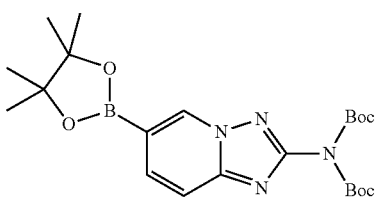 [SMILES: CC(C)(C)OC(=O)N(C(=O)OC(C)(C)C)c1nc2ccc(B3OC(C)(C)C(C)(C)O3)cn2n1]

Step A: tert-Butyl N-(6-bromo-[1,2,4]triazolo[1,5-a]pyridin-2-yl)-N-tert-butoxycarbonyl-carbamate To stirred suspension of 6-bromo-[1,2,4]triazolo[1,5-a]pyridin-2-amine (1.00 g, 4.69 mmol) in acetonitrile (20 mL) was added triethylamine (720 µL, 5.16 mmol) and 4-(dimethylamino)pyridine (29 mg, 235 µmol) followed by di-tert-butyl dicarbonate (2.25 g, 10.3 mmol). After 16 hours, the reaction mixture was concentrated, dissolved in diethyl ether (20 mL) and washed with water (20 mL) and saturated sodium bicarbonate solution (20 mL). The organic extract was dried over Na$_2$SO$_4$, filtered, concentrated to dryness and triturated with petroleum ether to give the desired product as a beige solid (1.29 g, 66%).

$^1$H NMR (500 MHz, CDCl$_3$) δ 8.70 (s, 1H), 7.62 (d, J=1.2 Hz, 2H), 1.47 (s, 18H).

Step B: tert-Butyl N-tert-butoxycarbonyl-N-[6-(4,4,5,5-tetramethyl-1,3,2-dioxaborolan-2-yl)-[1,2,4]triazolo[1,5-a]pyridin-2-yl]carbamate A stirred solution of Pd(dppf)Cl$_2$ (44 mg, 60.5 µmol), triphenylphosphine (16 mg, 60.5 µmol) and potassium acetate (178 mg, 1.81 mmol) in 1,4-dioxane (1.5 mL) under a nitrogen atmosphere was heated at 90° C. for approximately 5 minutes. A solution of tert-butyl N-(6-bromo-[1,2,4]triazolo[1,5-a]pyridin-2-yl)-N-tert-butoxycarbonyl-carbamate (500 mg, 1.21 mmol) and bis(pinacolato)diboron (369 mg, 1.45 mmol) in 1,4-dioxane (2.5 mL) was added and heating continued for 3 hours. The reaction mixture was diluted with ethyl acetate (5 mL) and filtered through Celite®. The filtrate was washed with saturated sodium bicarbonate solution (3 mL), water (3 mL) and brine (3 mL). The organic layer was dried over Na$_2$SO$_4$, filtered, concentrated to dryness and purified by column chromatography (silica, petroleum ether:ethyl acetate, gradient elution from 100:0 to 0:100) to give the desired product as a colourless oil (261 mg, 46%).

$^1$H NMR (500 MHz, CDCl$_3$) δ 8.88 (s, 1H), 7.81 (dd, J=9.0, 1.1 Hz, 1H), 7.67 (dd, J=8.9, 0.9 Hz, 1H), 1.45 (s, 18H), 1.37 (s, 12H).

Example 1 (Sodium Salt): 3-(6-Aminopyridin-3-yl)-1-sulfamoyl-1H-pyrrole-2-carboxylic acid, Sodium Salt

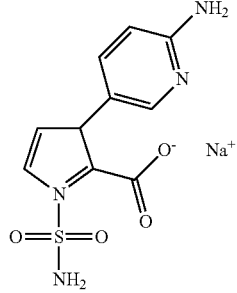

Step A: Sodium {[3-(6-aminopyridin-3-yl)-2-[(benzyloxy)carbonyl]-1H-pyrrol-1-yl]sulfonyl}[(benzyloxy)carbonyl]azanide A mixture of sodium [(benzyloxy)carbonyl]({2-[(benzyloxy)carbonyl]-3-bromo-1H-pyrrol-1-yl}sulfonyl)azanide (100 mg, 0.19 mmol), 6-aminopyridine-3-boronic acid (33 mg, 0.24 mmol) and sodium carbonate (64 mg, 0.60 mmol) in 1,4-dioxane (1.0 mL) and water (0.5 mL) was degassed by bubbling nitrogen for 5 minutes followed by the addition of Pd(dppf)Cl$_2$ (15 mg, 0.021 mmol). The resulting mixture was heated to 100° C. under microwave irradiation for 20 minutes. The reaction mixture was diluted with water (3 mL) and extracted into ethyl acetate (3×3 mL). The combined organic phases were washed with brine (3 mL), dried over MgSO$_4$, filtered and concentrated to dryness under reduced pressure. The residue was purified by column chromatography (silica, DCM:methanol, gradient elution from 100:0 to 80:20) then triturated with diethyl ether to give the desired product as a tan solid (59 mg, 58%).

$^1$H NMR (500 MHz, DMSO-d$_6$) δ 7.94 (d, J=1.89 Hz, 1H), 7.53 (dd, J=2.36, 8.67 Hz, 1H), 7.40-7.45 (m, J=3.00, 6.50 Hz, 2H), 7.25-7.35 (m, 9H), 6.63 (br s, 2H), 6.57 (d, J=8.83 Hz, 1H), 6.17 (d, J=3.15 Hz, 1H), 5.14 (s, 2H), 4.85 (s, 2H).

LC-MS (Method A): R$_T$=2.68 min, m/z=507.0 [M+H]$^+$.

Step B: 3-(6-Aminopyridin-3-yl)-1-sulfamoyl-1H-pyrrole-2-carboxylic acid, Sodium Salt To a solution of sodium {[3-(6-aminopyridin-3-yl)-2-[(benzyloxy)carbonyl]-1H-pyrrol-1-yl]sulfonyl}[(benzyloxy)carbonyl]azanide (59 mg, 0.11 mmol) in methanol (4 mL) was added 10% palladium on carbon (50% wet, 25 mg, 0.023 mmol) and the resulting suspension hydrogenated under 1 atmosphere hydrogen at room temperature for 6 hours. The reaction mixture was filtered through Celite® and concentrated to dryness under reduced pressure, triturated with diethyl ether, filtered and dried at 40° C. under vacuum to give the desired product as a pale brown solid (17 mg, 51%).

$^1$H NMR (500 MHz, DMSO-d$_6$) δ 9.06 (brs, 2H), 8.04 (dd, J=0.63, 1.58 Hz, 1H), 7.60 (dd, J=2.21, 8.51 Hz, 1H), 7.04 (d, J=3.15 Hz, 1H), 6.37 (dd, J=0.95, 8.51 Hz, 1H), 6.13 (d, J=3.15 Hz, 1H), 5.75 (s, 2H).

LC-MS (Method C): R$_T$=1.35 min, m/z=281.1 [M−H]$^-$.

Example 1 (Free Acid): 3-(6-Aminopyridin-3-yl)-1-sulfamoyl-1H-pyrrole-2-carboxylic acid

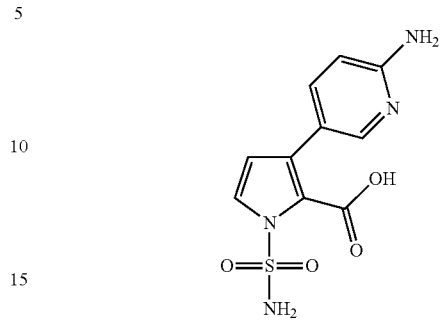

Step A: Benzyl 3-(6-amino-3-pyridyl)-1-(benzyloxycarbonylsulfamoyl)pyrrole-2-carboxylate A mixture of sodium [(benzyloxy)carbonyl]({2-[(benzyloxy)carbonyl]-3-bromo-1H-pyrrol-1-yl}sulfonyl)azanide (2.97 g, 5.76 mmol), 6-aminopyridine-3-boronic acid (872 mg, 6.32 mmol) and potassium phosphate tribasic (3.83 g, 18.0 mmol) in 1,4-dioxane (40 mL) and water (10 mL) was degassed by bubbling nitrogen for 15 minutes followed by the addition of XPhos Pd G2 (474 mg, 0.60 mmol). The resulting mixture was heated to 45° C. under a nitrogen atmosphere for 6 hours. Additional 6-aminopyridine-3-boronic acid (249 mg, 1.81 mmol) was added followed by heating at 45° C. overnight. Additional 6-aminopyridine-3-boronic acid (249 mg, 1.81 mmol) and XPhos Pd G2 (474 mg, 0.60 mmol) were added before heating at 45° C. for a further 2 hours. The reaction mixture was allowed to cool to room temperature, diluted with water (100 mL) and extracted into ethyl acetate (3×100 mL). The combined organic phases were dried over MgSO$_4$, filtered and concentrated to dryness under reduced pressure. The residue was triturated with DCM (30 mL), isolated by filtration and purified by column chromatography (silica, DCM:1M ammonia in methanol, gradient elution from 100:0 to 80:20). The precipitated solid from clean column fractions was isolated by filtration to give the desired product as a white solid (980 mg, 34%).

$^1$H NMR (500 MHz, DMSO-d$_6$) δ 13.34 (br s, 1H), 7.94 (d, J=1.6 Hz, 1H), 7.88 (br s, 2H), 7.86 (br dd, J=2.2, 9.1 Hz, 1H), 7.4-7.5 (m, 2H), 7.35 (d, J=3.2 Hz, 1H), 7.2-7.3 (m, 8H), 6.88 (d, J=8.8 Hz, 1H), 6.24 (d, J=2.8 Hz, 1H), 5.15 (s, 2H), 4.85 (s, 2H).

LC-MS (Method A): R$_T$=2.64 min, m/z=507.1 [M+H]$^+$.

Step B: 3-(6-Aminopyridin-3-yl)-1-sulfamoyl-1H-pyrrole-2-carboxylic acid

To a solution of benzyl 3-(6-amino-3-pyridyl)-1-(benzyloxycarbonylsulfamoyl)pyrrole-2-carboxylate (980 mg, 1.93 mmol) in a mixture of methanol (50 mL) and 1,4-dioxane (50 mL) was added 10% palladium on carbon (50% wet, 165 mg, 0.77 mmol) and the resulting suspension hydrogenated under an atmosphere of hydrogen at room temperature for 6 hours. The reaction mixture was filtered through Celite® followed by washing with 1M ammonia in methanol solution (50 mL) and concentration of these filtrates to dryness under reduced pressure. The residue was triturated with diethyl ether (30 mL), the solid isolated and dried by vacuum filtration to give the desired product as a white solid (445 mg, 81%).

$^1$H NMR (500 MHz, DMSO-$d_6$) δ 8.20 (br s, 2H), 7.99 (d, J=1.9 Hz, 1H), 7.51 (dd, J=2.4, 8.7 Hz, 1H), 7.38 (d, J=3.5 Hz, 1H), 6.50 (d, J=8.8 Hz, 1H), 6.31 (d, J=3.2 Hz, 1H), 6.29 (br s, 2H).

LC-MS (Method E): $R_T$=0.91 min, m/z=281.2 [M−H]$^-$.

Procedure for Conversion of free acid to sodium salt

To a suspension of 3-(6-amino-3-pyridyl)-1-sulfamoyl-pyrrole-2-carboxylic acid (500 mg, 1.77 mmol) in a mixture of ethanol (5 mL) and water (2.5 mL) was added 2M aqueous sodium hydroxide solution (886 μL, 1.77 mmol) and the resulting solution stirred at room temperature for 30 minutes. The reaction mixture was concentrated to dryness under reduced pressure, azeotroped with ethanol (2×50 mL) and dried under reduced pressure to give the desired sodium salt as an off-white solid (539 mg, 100%).

$^1$H NMR (500 MHz, DMSO-$d_6$) δ 8.88 (br s, 2H), 8.03 (dd, J=0.8, 2.4 Hz, 1H), 7.59 (dd, J=2.5, 8.5 Hz, 1H), 6.99 (d, J=3.2 Hz, 1H), 6.35 (dd, J=0.9, 8.5 Hz, 1H), 6.08 (d, J=3.2 Hz, 1H), 5.72 (s, 2H).

LC-MS (Method D): $R_T$=1.90 min, m/z=283.0 [M+H]$^+$.

Procedure for Conversion of sodium salt to free acid

A solution of 3-(6-amino-3-pyridyl)-1-sulfamoyl-pyrrole-2-carboxylic acid, sodium salt (10 mg, 0.033 mmol) in DMSO (0.04 mL) was diluted with water (0.3 mL) followed by the dropwise addition of 2M HCl$_{(aq)}$ (0.1 mL, 0.2 mmol). After stirring at room temperature for 5 minutes the precipitated solid was isolated by vacuum filtration, washed with water (0.2 mL) and dried under vacuum to give the desired product as a white solid (4 mg, 43%).

$^1$H NMR (500 MHz, DMSO-$d_6$) δ 8.19 (br s, 2H), 7.98 (dd, J=0.7, 2.5 Hz, 1H), 7.50 (dd, J=2.4, 8.7 Hz, 1H), 7.38 (d, J=3.2 Hz, 1H), 6.49 (d, J=8.5 Hz, 1H), 6.31 (d, J=3.2 Hz, 1H), 6.25 (br s, 2H).

LC-MS (Method D): $R_T$=1.52 min, m/z=283.0 [M+H]$^+$.

Further Examples

The following examples were prepared in a similar manner to 3-(6-aminopyridin-3-yl)-1-sulfamoyl-1H-pyrrole-2-carboxylic acid (free acid or sodium salt) starting from sodium [(benzyloxy)carbonyl]({2-[(benzyloxy)carbonyl]-3-bromo-1H-pyrrol-1-yl}sulfonyl)azanide.

| Example | Structure | Name | Analytical Data |
| --- | --- | --- | --- |
| Example 2 (sodium salt) | 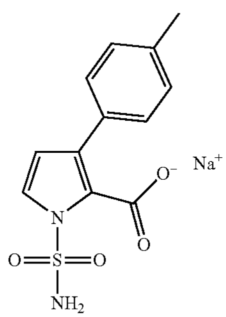 [SMILES: Cc1ccc(-c2ccn(S(N)(=O)=O)c2C(=O)[O-])cc1 ; [Na+]] | 3-(p-tolyl)-1-sulfamoyl-1H-pyrrole-2-carboxylic acid, sodium salt | $^1$H NMR (500 MHz, DMSO-$d_6$) δ 8.89 (br s, 2H), 7.42 (d, J = 7.88 Hz, 2H), 7.08 (d, J = 7.88 Hz, 2H), 7.07 (d, J = 3.15 Hz, 1H), 6.18 (d, J = 3.15 Hz, 1H), 2.29 (s, 3H). LC-MS (Method C): $R_T$ = 7.17 min, m/z = 279.1 [M − H]$^-$. |
| Example 3 (sodium salt) | 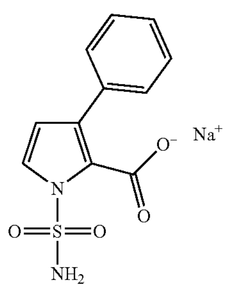 [SMILES: NS(=O)(=O)n1ccc(-c2ccccc2)c1C(=O)[O-] ; [Na+]] | 3-Phenyl-1-sulfamoyl-1H-pyrrole-2-carboxylic acid, sodium salt | $^1$H NMR (500 MHz, DMSO-$d_6$) δ 8.51 (br s, 2H), 7.46 (d, J = 7.25 Hz, 2H), 7.34 (t, J = 7.57 Hz, 2H), 7.23-7.30 (m, 2H), 6.31 (br d, J = 2.84 Hz, 1H). LC-MS (Method C): $R_T$ = 6.57 min, m/z = 265.1 [M − H]$^-$. |
| Example 4 (sodium salt) | 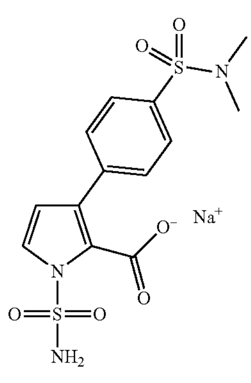 [SMILES: CN(C)S(=O)(=O)c1ccc(-c2ccn(S(N)(=O)=O)c2C(=O)[O-])cc1 ; [Na+]] | 3-[4-(Dimethylsulfamoyl)phenyl]-1-sulfamoyl-1H-pyrrole-2-carboxylic acid, sodium salt | $^1$H NMR (500 MHz, DMSO-$d_6$) δ 8.60 (br s, 2H), 7.72-7.76 (m, 2H), 7.68-7.72 (m, 2H), 7.31 (br d, J = 2.52 Hz, 1H), 6.42 (d, J = 3.15 Hz, 1H), 2.64 (s, 6H). LC-MS (Method C): $R_T$ = 6.47 min, m/z = 372.0 [M − H]$^-$. |

-continued

| Example | Structure | Name | Analytical Data |
|---|---|---|---|
| Example 5 (sodium salt) | 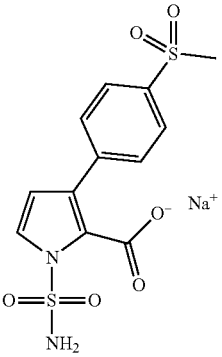 [SMILES: CS(=O)(=O)c1ccc(-c2ccn(S(N)(=O)=O)c2C(=O)[O-])cc1 ; [Na+]] | 3-(4-Methanesulfonylphenyl)-1-sulfamoyl-1H-pyrrole-2-carboxylic acid, sodium salt | $^1$H NMR (500 MHz, DMSO-$d_6$) δ 9.04 (br s, 2H), 7.81-7.77 (m, 4H), 7.07 (d, J = 3.2 Hz, 1H), 6.29 (d, J = 3.2 Hz, 1H), 3.20 (s, 3H). LC-MS (Method D): $R_T$ = 3.23 min, m/z = 343.0 [M − H]$^-$. |
| Example 6 (sodium salt) | 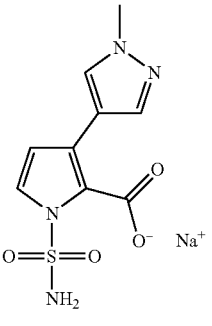 [SMILES: Cn1cc(-c2ccn(S(N)(=O)=O)c2C(=O)[O-])cn1 ; [Na+]] | 3-(1-Methyl-1H-pyrazol-4-yl)-1-sulfamoyl-1H-pyrrole-2-carboxylic acid, sodium salt | $^1$H NMR (500 MHz, DMSO-$d_6$) δ 9.15 (br s, 2H), 8.21 (s, 1H), 7.76 (s, 1H), 7.01 (d, J = 3.2 Hz, 1H), 6.25 (d, J = 3.2 Hz, 1H), 3.80 (s, 3H) LC-MS (Method D): $R_T$ = 0.41 min, m/z = 271.1 [M + H]$^+$. |
| Example 7 (sodium salt) | 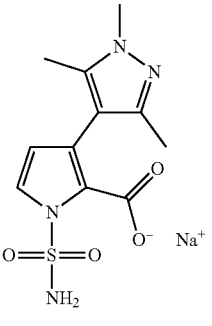 [SMILES: Cc1nn(C)c(C)c1-c1ccn(S(N)(=O)=O)c1C(=O)[O-] ; [Na+]] | 1-Sulfamoyl-3-(1,3,5-trimethyl-1H-pyrazol-4-yl)-1H-pyrrole-2-carboxylic acid, sodium salt | $^1$H NMR (500 MHz, DMSO-$d_6$) δ 9.47 (br s, 2H), 7.06 (d, J = 2.8 Hz, 1H), 5.89 (d, J = 2.8 Hz, 1H), 3.61 (s, 3H), 2.04 (s, 3H), 1.97 (s, 3H). LC-MS (Method D): $R_T$ = 2.81 min, m/z = 299.1 [M + H]$^+$. |
| Example 8 (sodium salt) | 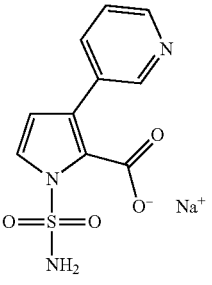 [SMILES: NS(=O)(=O)n1ccc(-c2cccnc2)c1C(=O)[O-] ; [Na+]] | 3-(Pyridin-3-yl)-1-sulfamoyl-1H-pyrrole-2-carboxylic acid, sodium salt | $^1$H NMR (500 MHz, DMSO-$d_6$) δ 9.21 (br s, 2H), 8.69 (dd, J = 1.7, 0.7 Hz, 1H), 8.36 (dd, J = 4.8, 1.7 Hz, 1H), 7.94 (dt, J = 8.0, 1.7 Hz, 1H), 7.30 (ddd, J = 8.0, 4.8, 0.7 Hz, 1H), 7.08 (d, J = 3.2 Hz, 1H), 6.26 (d, J = 3.2 Hz, 1H). LC-MS (Method D): $R_T$ = 1.74 min, m/z = 268.0 [M + H]$^+$. |
| Example 9 (sodium salt) | 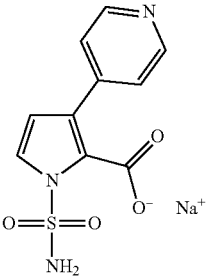 [SMILES: NS(=O)(=O)n1ccc(-c2ccncc2)c1C(=O)[O-] ; [Na+]] | 3-(Pyridin-4-yl)-1-sulfamoyl-1H-pyrrole-2-carboxylic acid, sodium salt | $^1$H NMR (500 MHz, DMSO-$d_6$) δ 9.05 (br s, 2H), 8.44-8.42 (m, 2H), 7.59-7.58 (m, 2H), 7.06 (d, J = 3.3 Hz, 1H), 6.35 (d, J = 3.3 Hz, 1H). LC-MS (Method D): $R_T$ = 0.41 min, m/z = 268.1 [M + H]$^+$. |

| Example | Structure | Name | Analytical Data |
|---|---|---|---|
| Example 10**† (sodium salt) | 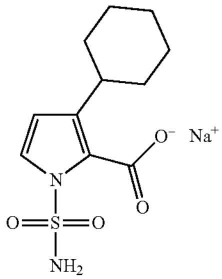 [SMILES: NS(=O)(=O)n1ccc(C2CCCCC2)c1C(=O)[O-] ; [Na+]] | 3-Cyclohexyl-1-sulfamoyl-pyrrole-2-carboxylic acid, sodium salt | $^1$H NMR (500 MHz, CD$_3$OD) δ 7.00 (d, J = 3.2 Hz, 1H), 5.96 (d, J = 3.2 Hz, 1H), 1.75-1.55 (m, 5H), 1.31-1.12 (m, 6H). LC-MS (Method D): R$_T$ = 4.36 min, m/z = 271.1 [M − H]$^-$. |
| Example 11† (sodium salt) | 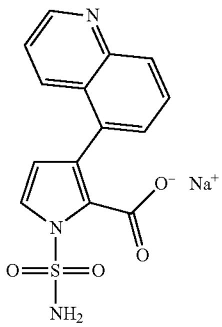 [SMILES: NS(=O)(=O)n1ccc(-c2cccc3ncccc23)c1C(=O)[O-] ; [Na+]] | 3-(5-Quinolyl)-1-sulfamoyl-pyrrole-2-carboxylic acid, sodium salt | $^1$H NMR (500 MHz, DMSO-d$_6$) δ 9.51 (br s, 2H), 8.90-8.80 (m, 1H), 8.14 (br d, J = 8.2 Hz, 1H), 7.91 (d, J = 8.5 Hz, 1H), 7.69 (t, J = 7.9 Hz, 1H), 7.50-7.40 (m, 2H), 7.23 (d, J = 2.8 Hz, 1H), 6.11 (d, J = 2.8 Hz, 1H). LC-MS (Method D): R$_T$ = 2.58 min, m/z = 318.1 [M + H]$^+$. |
| Example 12 (sodium salt) | 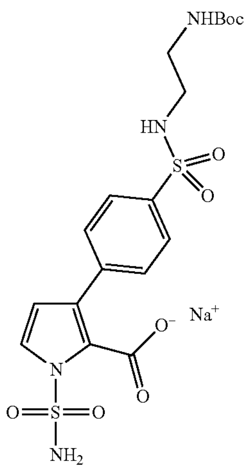 [SMILES: CC(C)(C)OC(=O)NCCNS(=O)(=O)c1ccc(-c2ccn(S(N)(=O)=O)c2C(=O)[O-])cc1 ; [Na+]] | 3-{4-[(2-{[(tert-Butoxy)carbonyl]amino}ethyl)sulfamoyl]phenyl}-1-sulfamoyl-1H-pyrrole-2-carboxylic acid, sodium salt | $^1$H NMR (500 MHz, DMSO-d$_6$) δ 9.12 (br s, 2H), 7.75-7.73 (m, 2H), 7.66-7.64 (m, 2H), 7.62-7.59 (m, 1H), 7.04 (d, J = 3.0 Hz, 1H), 8.82-6.79 (m, 1H), 6.28 (d, J = 3.0 Hz, 1H), 3.00-2.95 (m, 2H), 2.76-2.71 (m, 2H), 1.35 (s, 9H). LC-MS (Method C): R$_T$ = 7.07 min, m/z = 487.2 [M − H]$^-$. |
| Example 13*‡ (free acid) | 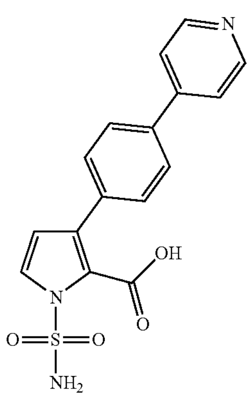 [SMILES: NS(=O)(=O)n1ccc(-c2ccc(-c3ccncc3)cc2)c1C(=O)O] | 3-[4-(Pyridin-4-yl)phenyl]-1-sulfamoyl-1H-pyrrole-2-carboxylic acid | $^1$H NMR (500 MHz, DMSO-d$_6$) δ 8.63 (dd, J = 1.6, 4.7 Hz, 2H), 8.51 (br s, 2H), 7.7-7.8 (m, 6H), 7.06 (d, J = 3.2 Hz, 1H), 6.29 (d, J = 3.2 Hz, 1H). LC-MS (Method D): R$_T$ = 2.55 min, m/z = 344.0 [M + H]$^+$. |

*To aid solubility, 7M ammonia in methanol was used as a co-solvent in the hydrogenation step.
**Prepared as described using (cyclohex-1-en-1-yl)boronic acid.
†The Suzuki coupling step was performed under conventional heating.
‡An HCl$_{(aq)}$ wash was performed during workup of the Suzuki coupling step.

Example 14 (free acid): 3-(2-Fluorophenyl)-1-sulfamoyl-pyrrole-2-carboxylic acid

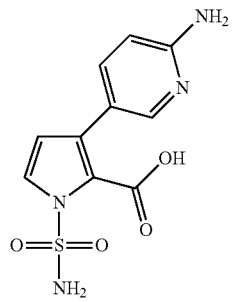 [SMILES: Nc1ccc(-c2ccn(S(N)(=O)=O)c2C(=O)O)cn1]

Step A: Benzyl 1-(benzyloxycarbonylsulfamoyl)-3-(2-fluorophenyl)pyrrole-2-carboxylate A mixture of sodium [(benzyloxy)carbonyl]({2-[(benzyloxy)carbonyl]-3-bromo-1H-pyrrol-1-yl}sulfonyl)azanide (200 mg, 0.39 mmol), (2-fluorophenyl)boronic acid (60 mg, 0.43 mmol) and anhydrous potassium phosphate tribasic (247 mg, 1.16 mmol) in 1,4-dioxane (4.0 mL) and water (1.0 mL) was degassed by bubbling nitrogen for 5 minutes. XPhos Pd G2 (61 mg, 0.08 mmol) was added to the reaction mixture and heated at 45° C. under microwave irradiation for 30 minutes. The reaction mixture was diluted with water (20 mL) and extracted into ethyl acetate (3×20 mL). The combined extracts were washed with 2M HCl$_{aq}$ (2×10 mL), dried over MgSO$_4$, filtered and concentrated to dryness. The residue was purified by column chromatography (silica, 0-100% ethyl acetate/petroleum ether) to afford desired product as a yellow solid/gum (142 mg, 72%).

$^1$H NMR (500 MHz, DMSO-d$_6$) δ 7.42 (d, J=3.15 Hz, 1H), 7.36-7.29 (m, 7H), 7.27-7.21 (m, 5H), 7.19-7.14 (m, 2H), 6.27 (d, J=2.8 Hz, 1H), 5.10 (s, 2H), 4.97 (s, 2H).
$^{19}$F NMR (471 MHz, DMSO-d$_6$) δ −115.27 (s, 1F).
LC-MS (Method A): R$_T$=3.07 min, m/z=507.1 [M−H]$^-$.

Step B: 3-(2-Fluorophenyl)-1-sulfamoyl-pyrrole-2-carboxylic acid

To a solution of benzyl 1-(benzyloxycarbonylsulfamoyl)-3-(2-fluorophenyl)pyrrole-2-carboxylate (142 mg, 0.28 mmol) in methanol (5 mL) was added 10% palladium on carbon (50% wet, 59 mg, 0.028 mmol) and the resulting suspension hydrogenated under 1 atmosphere hydrogen at room temperature for 6 hours. The reaction mixture was filtered through Celite® followed by washing with methanol (2×40 mL) and concentration of the combined filtrates to dryness under reduced pressure. The residue was triturated with diethyl ether/petroleum ether followed by diethyl ether/pentane, filtered and dried under vacuum to give the desired product as a white solid (8.8 mg, 10%).

$^1$H NMR (500 MHz, DMSO-d$_6$) δ 9.36 (br s, 2H), 7.38 (td, J=7.2, 1.5 Hz, 1H), 7.27-7.23 (m, 1H), 7.13-7.09 (m, 3H), 6.11 (br d, J=1.6 Hz, 1H).
$^{19}$F NMR (471 MHz, DMSO-d$_6$) δ −114.19 (s, 1F).
LC-MS (Method C): R$_T$=6.35 min, m/z=283.1 [M−H]$^-$.

Further Examples

The following examples were prepared in a similar manner to 3-(2-fluorophenyl)-1-sulfamoyl-pyrrole-2-carboxylic acid starting from sodium [(benzyloxy)carbonyl]({2-[(benzyloxy)carbonyl]-3-bromo-1H-pyrrol-1-yl}sulfonyl)azanide.

| Example | Structure | Name | Analytical Data |
| --- | --- | --- | --- |
| Example 15* (free acid) | 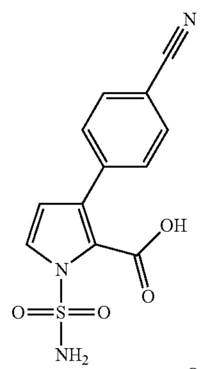 [SMILES: N#Cc1ccc(-c2ccn(S(N)(=O)=O)c2C(=O)O)cc1] | 3-(4-Cyanophenyl)-1-sulfamoyl-1H-pyrrole-2-carboxylic acid | $^1$H NMR (500 MHz, DMSO-d$_6$) δ 8.85 (br s, 2H), 7.78 (d, J = 7.8 Hz, 2H), 7.71 (d, J = 7.8 Hz, 2H), 7.07 (d, J = 3.0 Hz, 1H), 6.32 (d, J = 3.0 Hz, 1H). LC-MS (Method E): R$_T$ = 0.89 min, m/z = 290.0 [M − H]$^-$. |
| Example 16*†† (free acid) | 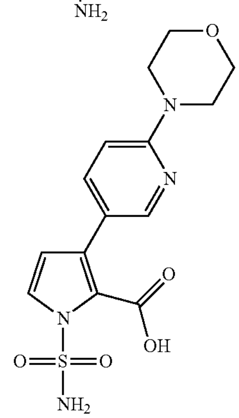 | 3-[6-(Morpholin-4-yl)pyridin-3-yl]-1-sulfamoyl-1H-pyrrole-2-carboxylic acid | $^1$H NMR (500 MHz, DMSO-d$_6$) δ 8.25 (d, J = 1.7 Hz, 1H), 7.80-7.79 (m, 1H), 7.05 (br s, 3H), 6.77 (d, J = 8.9 Hz, 1H), 6.20-6.17 (m, 1H), 3.71 (dd, J = 5.63, 4.63 Hz, 4H), 3.42 (dd, J = 6.00, 4.63 Hz, 4H). LC-MS (Method C): R$_T$ = 1.25 min, m/z = 351.2 [M − H]$^-$. Preparative HPLC (Method A): 0.80-1.00 min. |

| Example | Structure | Name | Analytical Data |
|---|---|---|---|
| Example 17*††‡‡ (sodium salt) | 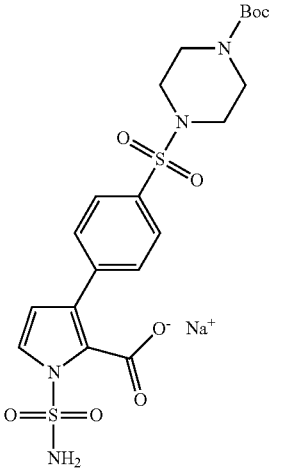 [SMILES: CC(C)(C)OC(=O)N1CCN(S(=O)(=O)c2ccc(-c3ccn(S(N)(=O)=O)c3C(=O)[O-])cc2)CC1 ; [Na+]] | 3-[4-(4-tert-Butoxycarbonylpiperazin-1-yl)sulfonylphenyl]-1-sulfamoyl-pyrrole-2-carboxylic acid, sodium salt | $^1$H NMR (500 MHz, DMSO-$d_6$) δ 9.06 (br s, 2H), 7.83-7.81 (m, 2H), 7.62-7.60 (m, 2H), 7.08 (d, J = 3.0 Hz, 1H), 6.32 (d, J = 3.0 Hz, 1H), 3.41-3.39 (m, 4H), 2.87-2.85 (m, 4H), 1.34 (s, 9H). LC-MS (Method C): $R_T$ = 7.81 min, m/z = 513.2 [M − H]$^-$. |
| Example 18†† (sodium salt) | 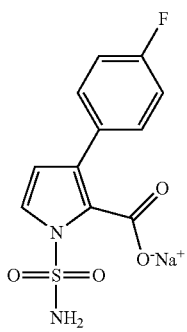 | 3-(4-Fluorophenyl)-1-sulfamoyl-pyrrole-2-carboxylic acid, sodium salt | $^1$H NMR (500 MHz, DMSO-$d_6$) δ 9.09 (br s, 2H), 7.58 (dd, J = 8.5, 6.0 Hz, 2H), 7.09 (t, J = 8.5 Hz, 2H), 7.02 (d, J = 2.7 Hz, 1H), 6.18 (d, J = 2.7 Hz, 1H). LC-MS (Method C): $R_T$ = 5.84 min, m/z = 283.1 [M − H]$^-$. |
| Example 19 (free acid) | 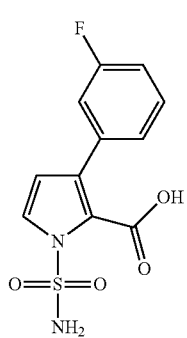 [SMILES: NS(=O)(=O)n1ccc(-c2cccc(F)c2)c1C(=O)O] | 3-(3-Fluorophenyl)-1-sulfamoyl-pyrrole-2-carboxylic acid | $^1$H NMR (500 MHz, DMSO-$d_6$) δ 8.98 (br s, 2H), 7.48 (br d, J = 10.7 Hz, 1H), 7.37-7.29 (m, 2H), 7.08-7.06 (s, 1H), 7.02-6.98 (m, 1H), 6.28 (d, J = 3.2 Hz, 1H). LC-MS (Method C): $R_T$ = 6.63 min, m/z = 283.1 [M − H]$^-$. |
| Example 20 (free acid) | 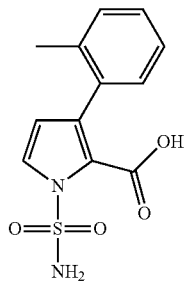 [SMILES: Cc1ccccc1-c1ccn(S(N)(=O)=O)c1C(=O)O] | 3-(o-Tolyl)-1-sulfamoyl-pyrrole-2-carboxylic acid | $^1$H NMR (500 MHz, DMSO-$d_6$) δ 8.83 (br s, 2H), 7.26 (br s, 1H), 7.18-7.07 (m, 4H), 6.06 (br s, 1H), 2.14 (s, 3H). LC-MS (Method C): $R_T$ = 5.68 min, m/z = 279.2 [M − H]$^-$. |

-continued

| Example | Structure | Name | Analytical Data |
|---|---|---|---|
| Example 21 (free acid) | 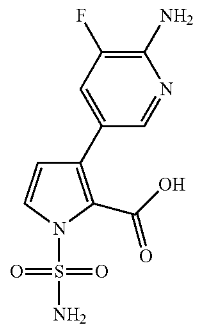 [SMILES: Nc1ncc(-c2ccn(S(N)(=O)=O)c2C(=O)O)cc1F] | 3-(6-Amino-5-fluoro-3-pyridyl)-1-sulfamoyl-pyrrole-2-carboxylic acid | $^1$H NMR (500 MHz, DMSO-$d_6$) δ 9.12 (br s, 2H), 7.91, J = 1.6 Hz, 1H), 7.78 (dd, J = 13.2, 1.6 Hz, 1H), 7.03 (d, J = 3.2 Hz, 1H), 6.22 (d, J = 3.2 Hz, 1H), 6.04 (br s, 2H). $^{19}$F NMR (471 MHz, DMSO-$d_6$) δ −141.07 (s, 1F). LC-MS (Method C): $R_T$ = 0.51 min, m/z = 299.0 [M − H]$^-$. |
| Example 22‡ (free acid) | 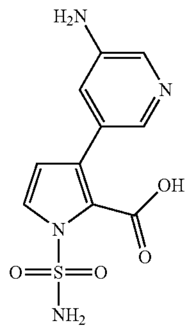 [SMILES: Nc1cncc(-c2ccn(S(N)(=O)=O)c2C(=O)O)c1] | 3-(5-Amino-3-pyridyl)-1-sulfamoyl-pyrrole-2-carboxylic acid | $^1$H NMR (500 MHz, DMSO-$d_6$) δ 9.21 (br s, 2H), 7.86 (s, 1H), 7.75 (d, J = 2.5 Hz, 1H), 7.09 (br t, J = 2.5 Hz, 1H), 7.04 (d, J = 3.2 Hz, 1H), 6.14 (d, J = 2.5 Hz, 1H), 5.13 (s, 2H). LC-MS (Method C): $R_T$ = 0.40 min, m/z = 281.0 [M − H]$^-$. |
| Example 23 (free acid) | 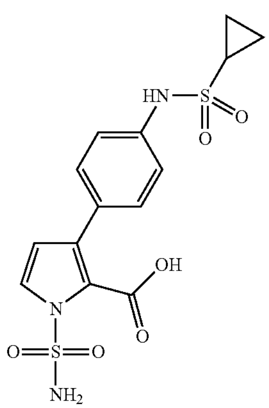 [SMILES: NS(=O)(=O)n1ccc(-c2ccc(NS(=O)(=O)C3CC3)cc2)c1C(=O)O] | 3-[4-(Cyclopropylsulfonylamino)phenyl]-1-sulfamoyl-pyrrole-2-carboxylic acid | $^1$H NMR (500 MHz, DMSO-$d_6$) δ 9.61 (br s, 1H), 9.07 (br s, 2H), 7.40 (d, J = 8.6 Hz, 2H), 7.13 (d, J = 8.6 Hz, 2H), 7.00 (d, J = 3.2 Hz, 1H), 6.17 (d, J = 3.2 Hz, 1H), 2.62-2.57 (m, 1H), 0.94 (d, J = 6.3 Hz, 4H). LC-MS (Method C): $R_T$ = 2.51 min, m/z = 384.1 [M − H]$^-$. |
| Example 24 (free acid) | 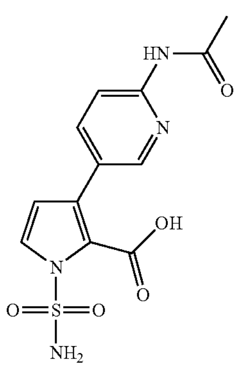 [SMILES: CC(=O)Nc1ccc(-c2ccn(S(N)(=O)=O)c2C(=O)O)cn1] | 3-(6-Acetamido-3-pyridyl)-1-sulfamoyl-pyrrole-2-carboxylic acid | $^1$H NMR (500 MHz, DMSO-$d_6$) δ 10.40 (s, 1H), 9.18 (br s, 2H), 8.45 (d, J = 1.9 Hz, 1H), 7.97 (br d, J = 8.4 Hz, 1H), 7.89 (dd, J = 8.4, 1.9 Hz, 1H), 7.07 (d, J = 3.2 Hz, 1H), 6.24 (d, J = 3.2 Hz, 1H), 2.09 (s, 3H). LC-MS (Method A): $R_T$ = 1.21 min, m/z = 323.3 [M − H]$^-$. |

| Example | Structure | Name | Analytical Data |
|---|---|---|---|
| Example 25†† (sodium salt) | 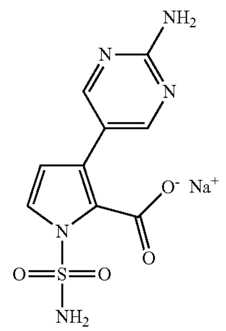 [SMILES: Nc1ncc(-c2ccn(S(N)(=O)=O)c2C(=O)[O-])cn1 ; [Na+]] | 3-(2-Aminopyrimidin-5-yl)-1-sulfamoyl-pyrrole-2-carboxylic acid, sodium salt | $^1$H NMR (500 MHz, DMSO-$d_6$) δ 9.26 (br s, 2H), 8.37 (s, 2H), 7.07 (d, J = 3.0 Hz, 1H), 6.45 (s, 2H), 6.16 (d, J = 3.0 Hz, 1H). LC-MS (Method A): $R_T$ = 1.42 min, m/z = 282.2 [M − H]$^-$. |
| Example 26* (free acid) | 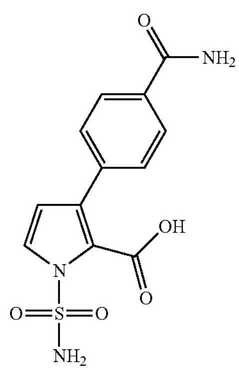 [SMILES: NC(=O)c1ccc(-c2ccn(S(N)(=O)=O)c2C(=O)O)cc1] | 3-(4-Carbamoylphenyl)-1-sulfamoyl-pyrrole-2-carboxylic acid | $^1$H NMR (500 MHz, DMSO-$d_6$) δ 9.05 (br s, 2H), 7.91 (br s, 1H), 7.79 (d, J = 7.6 Hz, 2H), 7.61 (d, J = 7.6 Hz, 2H), 7.25 (br s, 1H), 7.04 (d, J = 3.0 Hz, 1H), 6.28 (d, J = 3.0 Hz, 1H). LC-MS (Method B): $R_T$ = 0.31 min, m/z = 308.1 [M − H]$^-$. |
| Example 27* (sodium salt) | 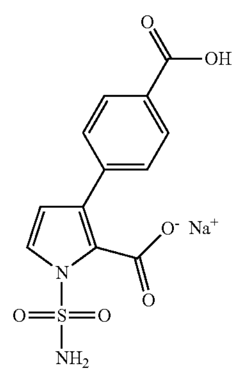 [SMILES: NS(=O)(=O)n1ccc(-c2ccc(C(=O)O)cc2)c1C(=O)[O-] ; [Na+]] | 3-(4-Carboxyphenyl)-1-sulfamoyl-pyrrole-2-carboxylic acid, sodium salt | $^1$H NMR (500 MHz, DMSO-$d_6$) δ 12.95 (br s, 1H), 8.46 (br s, 2H), 7.91 (m, 2H), 7.58 (d, J = 8.0 Hz, 2H), 7.33 (m, 1H), 6.40 (d, J = 3.0 Hz, 1H). LC-MS (Method A): $R_T$ = 2.41 min, m/z = 309.2 [M − H]$^-$. |
| Example 28* (sodium salt) | 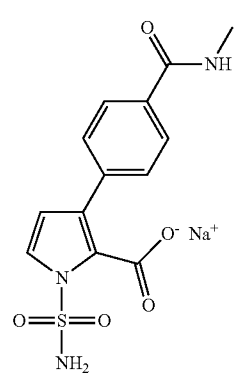 [SMILES: CNC(=O)c1ccc(-c2ccn(S(N)(=O)=O)c2C(=O)[O-])cc1 ; [Na+]] | 3-[4-(Methylcarbamoyl)phenyl]-1-sulfamoyl-pyrrole-2-carboxylic acid, sodium salt | $^1$H NMR (500 MHz, CD$_3$OD) δ 7.64 (d, J = 8.0 Hz, 2H), 7.48 (d, J = 8.0 Hz, 2H), 7.13 (d, J = 3.0 Hz, 1H), 6.19 (d, J = 3.0 Hz, 1H), 2.71 (s, 3H). LC-MS (Method A): $R_T$ = 2.18 min, m/z = 322.2 [M − H]$^-$. |

| Example | Structure | Name | Analytical Data |
|---|---|---|---|
| Example 29*† (free acid) | 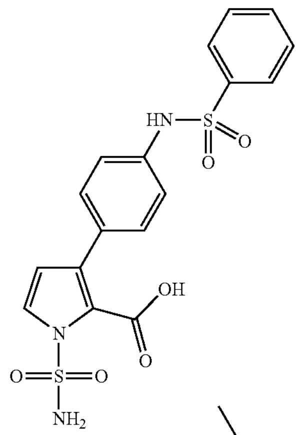 | 3-[4-(Benzenesulfonamido)phenyl]-1-sulfamoyl-pyrrole-2-carboxylic acid | $^1$H NMR (500 MHz, DMSO-$d_6$) δ 10.22 (br s, 1H), 8.96 (br s, 2H), 7.79 (br d, J = 7.3 Hz, 2H), 7.65-7.50 (m, 3H), 7.48-7.38 (m, 2H) 7.07-6.87 (m, 3H), 6.14 (d, J = 2.9 Hz, 1H). LC-MS (Method A): $R_T$ = 3.00 min, m/z = 420.2 [M − H]$^-$. |
| Example 30*† (free acid) | 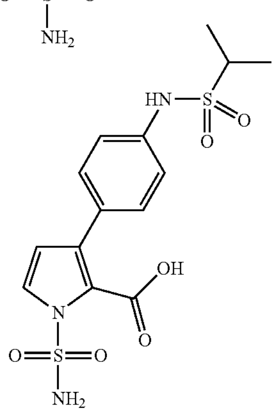 | 3-[4-(Isopropylsulfonylamino)phenyl]-1-sulfamoyl-pyrrole-2-carboxylic acid | $^1$H NMR (500 MHz, DMSO-$d_6$) δ 9.66 (br s, 1H), 9.04 (br s, 2H), 7.56-7.45 (m, 2H), 7.18-7.10 (m, 2H), 7.02 (d, J = 3.0 Hz, 1H), 6.17 (d, J = 3.0 Hz, 1H), 3.28-3.18 (m, 1H), 1.26 (d, J = 6.9 Hz, 6H). LC-MS (Method A): $R_T$ = 2.71 min, m/z = 386.2 [M − H]$^-$. |
| Example 31*† (free acid) | 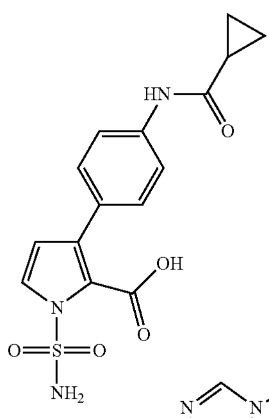 | 3-[4-(Cyclopropanecarbonylamino) phenyl]-1-sulfamoyl-pyrrole-2-carboxylic acid | $^1$H NMR (500 MHz, DMSO-$d_6$) δ 10.15 (s, 1H), 9.05 (br s, 2H), 7.48 (s, 4H), 7.00 (d, J = 2.9 Hz, 1H), 6.21-6.14 (m, 1H), 1.84-1.73 (m, 1H), 0.86-0.74 (m, 4H). LC-MS (Method A): $R_T$ = 2.64 min, m/z = 348.2 [M − H]$^-$. |
| Example 32*† (free acid) | 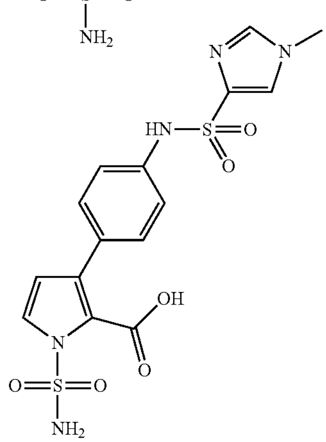 | 3-[4-[(1-Methylimidazol-4-yl)sulfonylamino]phenyl]-1-sulfamoyl-pyrrole-2-carboxylic acid | $^1$H NMR (500 MHz, DMSO-$d_6$) δ 10.10 (br s, 1H), 9.03 (br s, 2H), 7.81 (s, 1H), 7.74 (s, 1H), 7.40 (d, J = 8.4 Hz, 2H), 7.04 (d, J = 8.5 Hz, 2H), 6.98 (d, J = 2.9 Hz, 1H), 6.13 (d, J = 2.9 Hz, 1H), 3.72 (s, 3H). LC-MS (Method A): $R_T$ = 2.39 min, m/z = 424.3 [M − H]$^-$. |

| Example | Structure | Name | Analytical Data |
|---|---|---|---|
| Example 33†, ††† (free acid) | 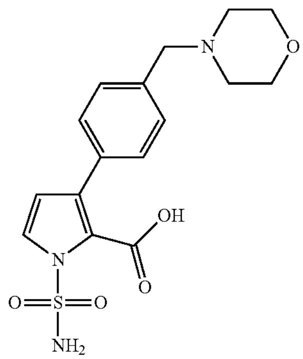 [SMILES: NS(=O)(=O)n1ccc(-c2ccc(CN3CCOCC3)cc2)c1C(=O)O] | 3-[4-(Morpholinomethyl)phenyl]-1-sulfamoyl-pyrrole-2-carboxylic acid | $^1$H NMR (500 MHz, DMSO-$d_6$) δ 13.19 (br s, 1H), 8.43 (br s, 2H), 7.42 (d, J = 7.8 Hz, 2H), 7.31-7.27 (m, 3H), 6.32 (br s, 1H), 3.60 (br t, J = 4.2 Hz, 4H), 3.53 (br s, 2H), 2.43 (br s, 4H). LC-MS (Method A): $R_T$ = 1.73 min, m/z = 364.3 [M − H]$^-$. |

*The Suzuki coupling step was performed under conventional heating.
†An aqueous ammonium chloride wash replaced the HCl wash during workup of the Suzuki coupling step.
††A water wash replaced the HCl wash during workup of the Suzuki coupling step.
‡To aid solubility, 7 M ammonia in methanol was used as a co-solvent in the hydrogenation step.
‡‡To aid solubility, 1,4-dioxane was used as a co-solvent in the hydrogenation step.
‡‡‡The hydrogenation step was limited to 15 minutes reaction time to avoid undesired debenzylation.

Example 34 (hydrochloride salt): 3-[4-(Piperidin-4-yl)phenyl]-1-sulfamoyl-1H-pyrrole-2-carboxylic acid hydrochloride

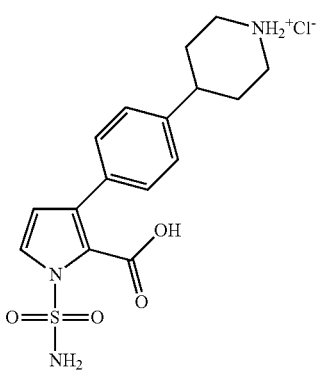

Step A: Sodium [(benzyloxy)carbonyl]({2-[(benzyloxy)carbonyl]-3-(4-{1-[(tert-butoxy)carbonyl]piperidin-4-yl}phenyl)-1H-pyrrol-1-yl}sulfonyl)azanide A mixture of sodium [(benzyloxy)carbonyl]({2-[(benzyloxy)carbonyl]-3-bromo-1H-pyrrol-1-yl}sulfonyl)azanide (100 mg, 0.19 mmol), tert-butyl 4-[4-(4,4,5,5-tetramethyl-1,3,2-dioxaborolan-2-yl)phenyl]piperidine-1-carboxylate (93 mg, 0.24 mmol) and sodium carbonate (64 mg, 0.60 mmol) in 1,4-dioxane (1.0 mL) and water (0.5 mL) was degassed by bubbling nitrogen for 5 minutes followed by the addition of Pd(dppf)Cl$_2$ (15 mg, 0.021 mmol). The resulting mixture was heated to 100° C. under microwave irradiation for 20 minutes. The reaction mixture was diluted with water (3 mL) and extracted into ethyl acetate (3×3 mL). The combined organic phases were washed with brine (3 mL), dried over MgSO$_4$, filtered and concentrated to dryness under reduced pressure. The residue was purified by column chromatography (silica, DCM:methanol, gradient elution from 100:0 to 90:10) and trituration with diethyl ether to give the desired product as a grey solid (25 mg, 19%).

$^1$H NMR (500 MHz, METHANOL-$d_4$) δ 7.46 (d, J=3.2 Hz, 1H), 7.18-7.30 (m, 10H), 7.08-7.11 (m, 2H), 7.04-7.08 (m, 2H), 6.19 (d, J=3.2 Hz, 1H), 5.14 (s, 2H), 5.00 (s, 2H), 4.22 (br d, J=12.9 Hz, 2H), 2.89 (br s, 2H), 2.70 (tt, J=3.4, 12.1 Hz, 1H), 1.81 (br d, J=12.6 Hz, 2H), 1.57 (dq, J=4.4, 12.7 Hz, 2H), 1.51 (s, 9H).

LC-MS (Method A): $R_T$=4.16 min, m/z=672.2 [M−H]$^-$.

Step B: Benzyl 1-({[(benzyloxy)carbonyl]amino}sulfonyl)-3-[4-(piperidin-4-yl)phenyl]-1H-pyrrole-2-carboxylate hydrochloride To a solution of sodium [(benzyloxy)carbonyl]({2-[(benzyloxy)carbonyl]-3-(4-{1-[(tert-butoxy)carbonyl]piperidin-4-yl}phenyl)-1H-pyrrol-1-yl}sulfonyl)azanide (25 mg, 0.036 mmol) in DCM (1.0 mL) was added 5M HCl in propan-2-ol (1.0 mL), followed by stirring at room temperature for 2 hours. The reaction mixture was then concentrated to dryness under reduced pressure and triturated with diethyl ether to give the desired product as a brown solid (21 mg, 94%).

$^1$H NMR (500 MHz, METHANOL-$d_4$) δ 7.52 (d, J=3.2 Hz, 1H), 7.30-7.35 (m, 5H), 7.22-7.30 (m, 5H), 7.18 (br d, J=7.9 Hz, 2H), 7.08 (br d, J=6.9 Hz, 2H), 6.32 (d, J=3.5 Hz, 1H), 5.18 (s, 2H), 5.18 (s, 2H), 3.54 (br d, J=11.0 Hz, 2H), 3.18 (br t, J=12.0 Hz, 2H), 2.92 (br t, J=11.7 Hz, 1H), 2.08 (br d, J=13.9 Hz, 2H), 1.93 (br q, J=11.9 Hz, 2H).

LC-MS (Method A): $R_T$=3.06 min, m/z=574.0 [M+H]$^+$.

Step C: 3-[4-(Piperidin-4-yl)phenyl]-1-sulfamoyl-1H-pyrrole-2-carboxylic acid hydrochloride To a solution of benzyl 1-({[(benzyloxy)carbonyl]amino}sulfonyl)-3-[4-(piperidin-4-yl)phenyl]-1H-pyrrole-2-carboxylate hydrochloride (21 mg, 0.034 mmol) in methanol (2 mL) was added 10% palladium on carbon (50% wet, 7 mg, 7 μmol) and the resulting suspension hydrogenated under 1 atmosphere hydrogen at room temperature for 6 hours. The reaction mixture was filtered through Celite® and concentrated to dryness under reduced pressure, triturated with diethyl ether and dried at 40° C. under vacuum to give the desired product as a pale brown solid (11 mg, 85%).

¹H NMR (500 MHz, DMSO-d₆) δ 13.13 (br s, 1H), 8.96 (br s, 1H), 8.87 (br s, 1H), 8.20 (br s, 2H), 7.41 (d, J=3.2 Hz, 1H), 7.38 (d, J=8.2 Hz, 2H), 7.24 (d, J=8.2 Hz, 2H), 6.36 (d, J=3.2 Hz, 1H), 2.99 (br q, J=11.0 Hz, 2H), 2.86 (tt, J=3.0, 12.20 Hz, 1H), 2.40-2.60 (m, 2H), 1.81-1.99 (m, 4H). The multiplet at 2.40-2.60 is partially obscured by the residual DMSO peak.

LC-MS (Method D): $R_T$=2.18 min, m/z=350.2 [M+H]⁺.

Further Examples

The following examples were prepared in a similar manner to 3-[4-(piperidin-4-yl)phenyl]-1-sulfamoyl-1H-pyrrole-2-carboxylic acid hydrochloride starting from sodium [(benzyloxy)carbonyl]({2-[(benzyloxy)carbonyl]-3-bromo-1H-pyrrol-1-yl}sulfonyl)azanide.

| Example | Structure | Name | Analytical Data |
|---|---|---|---|
| Example 35 (free acid) | 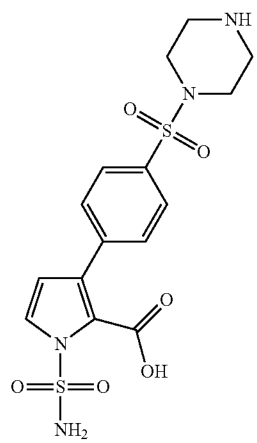 [SMILES: NS(=O)(=O)n1ccc(-c2ccc(S(=O)(=O)N3CCNCC3)cc2)c1C(=O)O] | 3-[4-(Piperazine-1-sulfonyl)phenyl]-1-sulfamoyl-1H-pyrrole-2-carboxylic acid | ¹H NMR (500 MHz, DMSO-d₆) δ 8.25 (s, 2H), 7.83-7.81 (m, 2H), 7.60-7.58 (m, 2H), 7.06 (d, J = 3.2 Hz, 1H), 6.31 (d, J = 3.2 Hz, 1H), 2.81-2.78 (m, 4H), 2.73-2.72 (m, 4H), LC-MS (Method C): $R_T$ = 5.34 min, m/z = 415.0 [M + H]⁺. Preparative HPLC (Method A): 1.00-1.11 min. |
| Example 36* (free acid) | 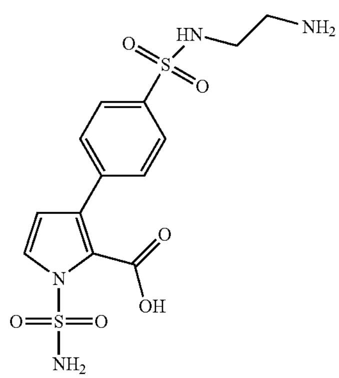 [SMILES: NCCNS(=O)(=O)c1ccc(-c2ccn(S(N)(=O)=O)c2C(=O)O)cc1] | 3-{4-[(2-Aminoethyl)sulfamoyl]phenyl}-1-sulfamoyl-1H-pyrrole-2-carboxylic acid | ¹H NMR (500 MHz, DMSO-d₆) δ 8.28 (s, 2H), 7.77 (d, J = 8.5 Hz, 2H), 7.69 (d, J = 8.5 Hz, 2H), 7.07 (d, J = 3.3 Hz, 1H), 6.30 (d, J = 3.3 Hz, 1H), 2.92-2.89 (m, 2H), 2.79-2.76 (m, 2H). LC-MS (Method D): $R_T$ = 2.30 min, m/z = 389.1 [M + H]⁺. Preparative HPLC (Method A): 0.80-1.00 min. |
| Example 37** (hydrochloride salt) | 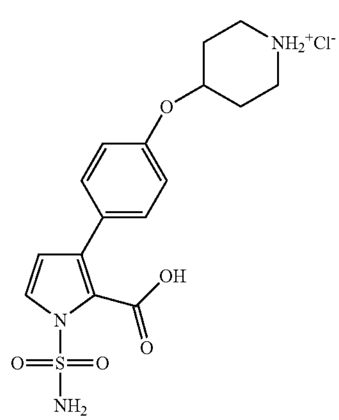 | 3-[4-(Piperidin-4-yloxy)phenyl]-1-sulfamoyl-1H-pyrrole-2-carboxylic acid hydrochloride | ¹H NMR (500 MHz, DMSO-d₆) δ 9.37 (br s, 2H), 8.28 (br s, 2H), 7.30-7.40 (m, 3H), 6.99 (br d, J = 7.9 Hz, 2H), 6.30 (br s, 1H), 4.68 (br s, 1H), 3.10-3.30 (m, 2H) 3.00-3.10 (m, 2H), 2.12 (br s, 2H), 1.88 (br s, 2H). LC-MS (Method C): $R_T$ = 2.14 min, m/z = 366.1 [M + H]⁺. |

| Example | Name | Analytical Data |
|---|---|---|
| Example 38** (hydrochloride salt) | 1-Sulfamoyl-3-(1,2,3,6-tetrahydropyridin-4-yl)-1H-pyrrole-2-carboxylic acid hydrochloride | $^1$H NMR (500 MHz, DMSO-$d_6$) δ 9.35 (br s, 2H), 8.22 (br s, 2H), 7.33 (d, J = 2.8 Hz, 1H), 6.24 (d, J = 3.2 Hz, 1H), 5.81 (br s, 1H), 3.65 (br s, 2H), 3.20 (m, 2H) 3.50-2.60 (m, 2H). LC-MS (Method D): $R_T$ = 0.41 min, m/z = 272.0 [M + H]$^+$. |
| Example 39‡ (free acid) | 3-[1-(4-Piperidyl)pyrazol-4-yl]-1-sulfamoyl-pyrrole-2-carboxylic acid | $^1$H NMR (500 MHz, DMSO-$d_6$) δ 8.36 (br d, J = 2.9 Hz, 1H), 7.81 (s, 1H), 7.05 (br s, 1H), 6.3 (d, J = 2.9 Hz, 1H), 4.49-4.42 (m, 1H), 3.39-3.36 (m, 2H), 3.05 (td, J = 3.2, 2.5 Hz, 2H), 2.20-2.08 (m, 4H). The multiplet at 3.39-3.36 is partially obscured by residual water. LC-MS (Method A): $R_T$ = 1.62 min. |
| Example 40† (hydrochloride salt) | 3-[3-(4-Piperidyl)phenyl]-1-sulfamoyl-pyrrole-2-carboxylic acid hydrochloride | $^1$H NMR (500 MHz, DMSO-$d_6$) δ 13.08 (br s, 1H), 8.93 (br s, 1H), 8.72 (br s, 1H), 8.20 (s, 2H), 7.42 (d, J = 3.2 Hz, 1H), 7.37-7.34 (m, 1H), 7.28-7.26 (m, 2H), 7.18 (br d, J = 7.6 Hz, 1H), 6.37 (d, J = 3.2 Hz, 1H), 3.39-3.37 (m, 2H), 3.00 (br q, J = 11.9 Hz, 2H), 2.90-2.84 (m, 1H), 1.94-1.93 (m, 2H), 1.91-1.82 (m, 2H). The multiplet at 3.39-3.37 is partially obscured by residual water. LC-MS (Method A): RT = 2.15 min, m/z = 348.3 [M + H]$^+$. |
| Example 41 (hydrochloride salt) | 3-(3-Piperazin-1-ylphenyl)-1-sulfamoyl-pyrrole-2-carboxylic acid hydrochloride | $^1$H NMR (500 MHz, DMSO-$d_6$) δ 13.15 (br s, 1H), 9.00 (br s, 2H), 8.19 (s, 2H), 7.41 (d, J = 3.2 Hz, 1H), 7.27 (t, J = 7.0 Hz, 1H), 7.02 (br s, 1H), 6.95 (dd, J = 8.0, 2.0 Hz, 1H), 6.91 (d, J = 7.5 Hz, 1H), 6.39 (d, J = 3.2 Hz, 1H), 3.34 (br s, 4H), 3.96 (br s, 4H). The peak at 3.34 is partially obscured by residual water. LC-MS (Method A): $R_T$ = 2.10 min, m/z = 349.3 [M − H]$^−$. |

-continued

| Example | Structure | Name | Analytical Data |
|---|---|---|---|
| Example 42*†† (hydrochloride salt) | 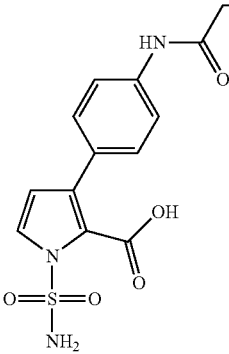 | 3-[4-[(2-Aminoacetyl)amino]phenyl]-1-sulfamoyl-pyrrole-2-carboxylic acid hydrochloride | $^1$H NMR (500 MHz, DMSO-$d_6$) δ 10.84 (s, 1H), 8.28 (br s, 5H), 7.62 (br d, J = 8.2 Hz, 2H), 7.48-7.32 (m, 3H), 6.35 (d, J = 2.9 Hz, 1H), 3.81 (s, 2H). LC-MS (Method A): $R_T$ = 1.61 min, m/z = 337.3 [M − H]$^−$. |
| Example 43*†‡‡ (hydrochloride salt) | 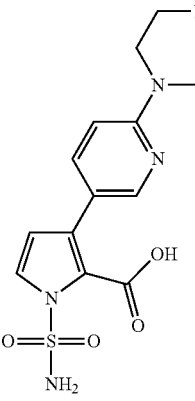 | 3-(6-Piperazin-1-yl-3-pyridyl)-1-sulfamoyl-pyrrole-2-carboxylic acid hydrochloride | $^1$H NMR (500 MHz, DMSO-$d_6$) δ 9.37 (br s, 2H), 8.21-8.15 (m, 2H), 7.81 (d, J = 4.8 Hz, 1H), 7.49 (d, J = 2.9 Hz, 1H), 7.10 (d, J = 4.8 Hz, 1H), 6.40 (d, J= 2.9 Hz, 1H), 4.66 (br s, 1H), 3.89-3.81 (m, 4H), 3.26-3.18 (m, 4H). LC-MS (Method B): $R_T$ = 0.38 min, m/z = 352.1 [M + H]$^+$. |
| Example 44 (hydrochloride salt) | 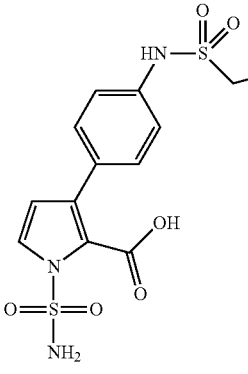 | 3-[4-(2-Aminoethylsulfonylamino)phenyl]-1-sulfamoyl-pyrrole-2-carboxylic acid hydrochloride | $^1$H NMR (500 MHz, DMSO-$d_6$) δ 13.21 (br s, 1H), 10.23 (br s, 1H), 8.26 (br s, 2H), 7.95 (br s, 3H), 7.43 (br d, J = 8.4 Hz, 2H), 7.40 (br d, J = 3.0 Hz, 1H), 7.24 (d, J = 8.4 Hz, 2H), 6.35 (d, J = 3.0 Hz, 1H), 3.46 (br t, J = 7.6 Hz, 2H), 3.19-3.16 (m, 2H). LC-MS (Method A): $R_T$ = 2.01 min, m/z = 387.3 [M − H]$^−$. |
| Example 45* (hydrochloride salt) | 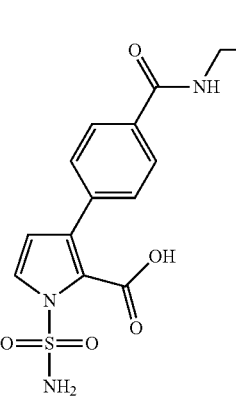 | 3-[4-(2-Aminoethylcarbamoyl)phenyl]-1-sulfamoyl-pyrrole-2-carboxylic acid hydrochloride | $^1$H NMR (500 MHz, DMSO-$d_6$) δ 9.14 (t, J = 5.5 Hz, 1H), 6.26 (br s, 5H), 7.87 (d, J = 8.5 Hz, 2H), 7.65 (d, J = 8.5 Hz, 2H), 7.10 (d, J = 3.0 Hz, 1H), 6.30 (d, J = 3.0 Hz, 1H), 3.53 (q, J = 5.5 Hz, 2H), 2.99 (t, J = 5.5 Hz, 2H). LC-MS (Method A): $R_T$ = 1.64 min, m/z = 351.3 [M − H]$^−$. |

| Example | Structure | Name | Analytical Data |
|---|---|---|---|
| Example 46†‡‡ (hydrochloride salt) | 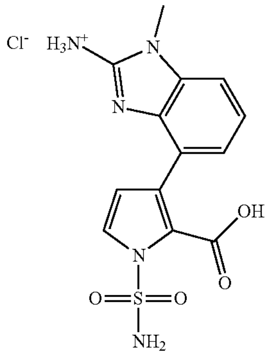 | 3-(2-Amino-1-methyl-benzimidazol-4-yl)-1-sulfamoyl-pyrrole-2-carboxylic acid hydrochloride | $^1$H NMR (500 MHz, DMSO-$d_6$) δ 12.80 (br s, 1H), 8.27 (br s, 4H), 7.57 (br s, 1H), 7.48 (d, J = 7.9 Hz, 1H), 7.40-7.25 (m, 1H), 7.15 (d, J = 7.6 Hz, 1H), 6.36 (d, J = 3.2 Hz, 1H), 3.68 (s, 3H). LC-MS (Method C): $R_T$ = 5.20 min, m/z = 334.3 [M − H]$^-$. |
| Example 47†‡‡ (hydrochloride salt) | 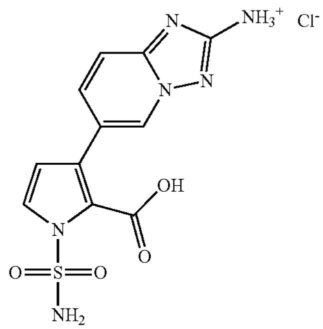 [SMILES: NS(=O)(=O)n1ccc(-c2ccc3nc([NH3+])nn3c2)c1C(=O)O ; [Cl-]] | 3-(2-Amino-[1,2,4]triazolo[1,5-a]pyridin-6-yl)-1-sulfamoyl-pyrrole-2-carboxylic acid hydrochloride | $^1$H NMR (500 MHz, DMSO-$d_6$) δ 8.81 (br s, 1H), 8.27 (s, 2H), 7.71 (br d, J = 8.4 Hz, 1H), 7.60-7.50 (m, 2H), 6.50 (d, J = 3.1 Hz, 1H). LC-MS (Method A): $R_T$ = 1.83 min, m/z = 321.2 [M − H]$^-$. |

*The Suzuki coupling step was performed under conventional heating.
**The Suzuki coupling step was performed as for 3-(6-aminopyridin-3-yl)-1-sulfamoyl-1H-pyrrole-2-carboxylic acid (sodium salt) under conventional heating
†An HCl$_{(aq)}$ wash was performed during workup of the Suzuki coupling step.
††An aqueous ammonium chloride wash was performed during workup of the Suzuki coupling step.
‡To aid solubility, 7 M ammonia in methanol was used as a co-solvent in the hydrogenation step.
‡‡‡Neat 4 M HCl in 1,4-dioxane was used for the Boc deprotection step.

Example 48 (free acid): 3-[4-(1-Acetylpiperidin-4-yl)phenyl]-1-sulfamoyl-1H-pyrrole-2-carboxylic acid

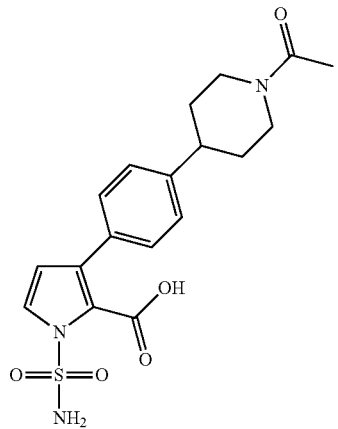 [SMILES: CC(=O)N1CCC(c2ccc(-c3ccn(S(N)(=O)=O)c3C(=O)O)cc2)CC1]

Step A: Benzyl 3-[4-(1-acetylpiperidin-4-yl)phenyl]-1-({[(benzyloxy)carbonyl]amino}sulfonyl)-1H-pyrrole-2-carboxylate Acetyl chloride (5.6 µL, 77.9 µmol) was added to a solution of benzyl 1-(benzyloxycarbonylsulfamoyl)-3-[4-(4-piperidyl)phenyl]pyrrole-2-carboxylate hydrochloride (50 mg, 82.0 µmol) and triethylamine (40.0 µL, 287 µmol) in DCM (2 mL) and the resulting clear yellow solution stirred at room temperature for 17 hours. The reaction mixture was quenched with saturated NaHCO$_3$ solution (5 mL) and water (5 mL) and extracted with DCM (3×10 mL). The combined extracts were dried over MgSO$_4$, filtered and concentrated under reduced pressure to afford the desired product as a clear gum which solidified on standing (42 mg, 83%).

$^1$H NMR (500 MHz, METHANOL-$d_4$) δ 7.37 (d, J=3.2 Hz, 1H), 7.29-7.19 (m, 11H), 7.17-7.15 (m, 2H), 7.12-7.11 (m, 2H), 6.17 (d, J=3.2 Hz, 1H), 5.16 (s, 2H), 4.95 (s, 2H), 4.70-4.65 (m, 1H), 4.07-4.02 (m, 1H), 2.79 (tt, J=12.2, 3.6 Hz, 1H), 2.72 (td, J=13.0, 2.4 Hz, 1H), 2.15 (s, 3H), 1.92-1.84 (m, 2H), 1.67 (qd, J=12.7, 4.3 Hz, 1H), 1.57 (qd, J=12.7, 4.3 Hz, 1H). One proton is obscured by the residual solvent peaks.

LC-MS (Method A): $R_T$=3.43 min, m/z=616.2 [M+H]$^+$.

Step B: 3-[4-(1-Acetyl-4-piperidyl)phenyl]-1-sulfamoyl-pyrrole-2-carboxylic acid To a solution of benzyl 3-[4-(1-acetyl-4-piperidyl)phenyl]-1-(benzyloxycarbonylsulfamoyl)pyrrole-2-carboxylate (42.0 mg, 68.2 µmol) in methanol (2 mL) was added 10% palladium on carbon (50% wet, 2 mg, 18.8 µmol) and the resulting suspension hydrogenated under 1 atmosphere hydrogen at room temperature for 5 hours. The reaction mixture was filtered through a pad of Celite®, washed with methanol (2×10 mL) and the filtrate collected, concentrated under reduced pressure, triturated with diethyl ether (3×5 mL) and dried under reduced pressure to afford the desired product as a white solid (19 mg, 57%).

$^1$H NMR (500 MHz, DMSO-$d_6$) δ 9.06 (br s, 2H), 7.42 (d, J=8.0 Hz, 2H), 7.15 (d, J=8.0 Hz, 2H), 7.06 (br s, 1H), 6.19 (br d, J=3.0 Hz, 1H), 4.55-4.50 (m, 1H), 3.95-3.90 (m, 1H), 3.12 (td, J=13.2, 2.7 Hz, 1H), 2.73 (tt, J=12.0, 3.6 Hz, 1H), 2.55-2.50 (m, 1H), 2.03 (s, 3H), 1.82-1.74 (m, 2H), 1.59 (qd, J=12.6, 4.2 Hz, 1H), 1.43 (qd, J=12.6, 4.2 Hz, 1H). The 1H multiplet at 2.55-2.50 is partially obscured by the DMSO peak.

LC-MS (Method D): $R_T$=6.59 min, m/z=390.3 [M−H]$^-$.

Example 49 (free acid): 3-[4-[1-(Dimethylsulfamoyl)piperidin-4-yl]phenyl]-1-sulfamoyl-1H-pyrrole-2-carboxylic acid

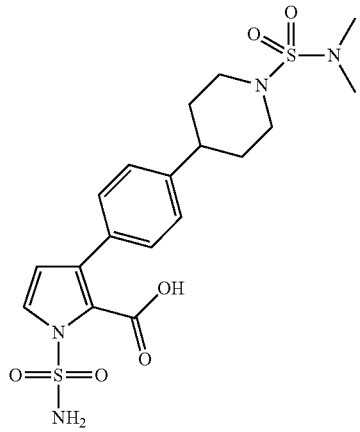 [SMILES: CN(C)S(=O)(=O)N1CCC(c2ccc(-c3ccn(S(N)(=O)=O)c3C(=O)O)cc2)CC1]

Step A: Benzyl 1-(benzyloxycarbonylsulfamoyl)-3-[4-[1-(dimethylsulfamoyl)-4-piperidyl]phenyl]pyrrole-2-carboxylate N,N-Dimethylsulfamoyl chloride (30.0 μL, 0.28 mmol) was added to a solution of benzyl 1-(benzyloxycarbonylsulfamoyl)-3-[4-(4-piperidyl)phenyl]pyrrole-2-carboxylate hydrochloride (170 mg, 0.28 mmol) and triethylamine (78 μL, 0.56 mmol) in DMF (5 mL) and stirred for 19 hours under nitrogen at room temperature. The reaction mixture was quenched with water (55 mL) and 2M HCl$_{(aq)}$ (10 mL), sonicated and stirred for 10 minutes. The resulting solid was filtered and dried under vacuum to give the desired crude product (114 mg, 60%). The material was used directly in the following step without further purification.

LCMS (Method A): $R_T$=2.12 min, m/z=681.1 [M+H]$^+$.

Step B: 3-[4-[1-(Dimethylsulfamoyl)piperidin-4-yl]phenyl]-1-sulfamoyl-1H-pyrrole-2-carboxylic acid To a solution of benzyl 1-(benzyloxycarbonylsulfamoyl)-3-[4-[1-(dimethylsulfamoyl)-4-piperidyl]phenyl]pyrrole-2-carboxylate (114 mg, 0.17 mmol) in methanol (5 mL) was added 10% palladium on carbon (50% wet, 36 mg, 0.017 mmol) and the resulting suspension hydrogenated under 1 atmosphere hydrogen at room temperature for 5.5 hours. The reaction mixture was filtered through a pad of Celite®, washed with methanol (2×10 mL) and the filtrates collected, concentrated under reduced pressure, triturated with diethyl ether (3×5 mL) and dried under reduced pressure to afford a white solid. Crude material was purified using preparative HPLC (Method A, 1.78-1.90 minutes) to afford the desired product (17 mg, 20%).

$^1$H NMR (500 MHz, DMSO-$d_6$) δ 13.15 (br s, 1H), 8.22 (br s, 2H), 7.38-7.31 (m, 3H), 7.26-7.24 (m, 2H), 6.33 (br s, 1H), 3.70-3.60 (m, 2H), 2.95 (td, J=12.3, 2.2 Hz, 2H), 2.76 (s, 6H), 1.85-1.83 (m, 2H), 1.69-1.61 (m, 3H).

LCMS (Method C): $R_T$=7.26 min, m/z=455.2 [M−H]$^-$.

Example 50 (Free Acid): 3-[4-[1-(2-Benzyloxyethyl)-4-piperidyl]phenyl]-1-sulfamoyl-pyrrole-2-carboxylic acid

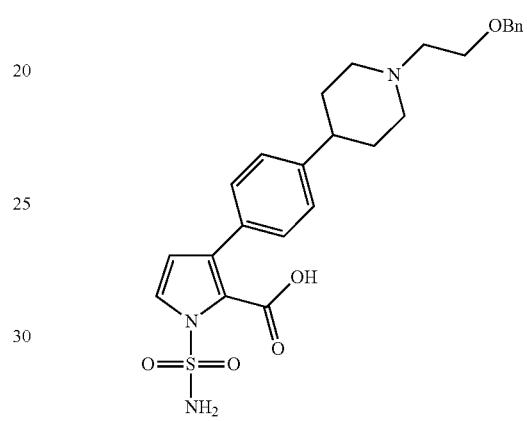

Step A: Benzyl 1-(benzyloxycarbonylsulfamoyl)-3-[4-[1-(2-benzyloxyethyl)-4-piperidyl]phenyl]pyrrole-2-carboxylate Benzyl 2-bromoethyl ether (130 μL, 0.8 mmol) was added to a solution of benzyl 1-(benzyloxycarbonylsulfamoyl)-3-[4-(4-piperidyl)phenyl]pyrrole-2-carboxylate hydrochloride (430 mg, 0.7 mmol) and potassium carbonate (292 mg, 2.1 mmol) in DMF (2 mL) and stirred at room temperature under nitrogen for 17 hours. The reaction mixture was quenched with water (10 mL) and extracted with ethyl acetate (3×10 mL). The combined extracts were washed with 1:1 water:brine (3×15 mL), dried over MgSO$_4$, filtered and concentrated under reduced pressure. The residue was purified by column chromatography (silica, DCM:methanol, gradient elution from 100:0 to 80:20) and trituration with diethyl ether to give the desired product as a white solid (298 mg, 60%).

$^1$H NMR (500 MHz, DMSO-$d_6$) δ 9.24 (br s, 1H), 7.41-7.37 (m, 6H), 7.34-7.25 (m, 12H), 7.17 (d, J=8.1 Hz, 2H), 6.20 (d, J=2.9 Hz, 1H), 5.14 (s, 2H), 4.86 (s, 2H), 4.59 (s, 2H), 3.79-3.76 (m, 2H), 3.61-3.58 (m, 2H), 3.39-3.36 (m, 2H), 3.15-3.07 (m, 2H), 2.80 (br t, J=11.8 Hz, 1H), 2.04-2.01 (m, 2H), 1.95-1.86 (m, 2H).

LC-MS (Method A): $R_T$=3.81 min, m/z=708.4 [M+H]$^+$.

Step B: 3-[4-[1-(2-Benzyloxyethyl)-4-piperidyl]phenyl]-1-sulfamoyl-pyrrole-2-carboxylic acid Benzyl-1-(benzyloxycarbonylsulfamoyl)-3-[4-[1-(2-benzyloxyethyl)-4-piperidyl]phenyl]pyrrole-2-carboxylate (156 mg, 0.22 mmol) was hydrogenated in a similar manner to 3-(6-aminopyridin-3-yl)-1-sulfamoyl-1H-pyrrole-2-carboxylic acid, sodium salt (Step B) with 7M ammonia in methanol as a co-solvent to give the desired product as a white solid (100 mg, 94%).

$^1$H NMR (500 MHz, DMSO-$d_6$) δ 12.50 (br s, 1H), 8.65 (br s, 2H), 7.45 (br d, J=8.1 Hz, 2H), 7.39-7.34 (m, 4H), 7.32-7.28 (m, 1H), 7.20-7.09 (m, 3H), 6.23 (d, J=3.2 Hz, 1H), 4.52 (s, 2H), 3.80-3.75 (m, 2H), 3.44-3.37 (m, 2H), 3.11-2.98 (m, 2H), 2.82-2.66 (m, 3H), 1.54 (br s, 4H). The multiplet at 2.82-2.66 is obscured by solvent peak.

LC-MS (Method A): $R_T$=3.08 min, m/z=484.2 [M+H]$^+$.

Example 51 (Hydrochloride Salt): 3-[4-(3-Aminopropylcarbamoyl)phenyl]-1-sulfamoyl-pyrrole-2-carboxylic acid hydrochloride

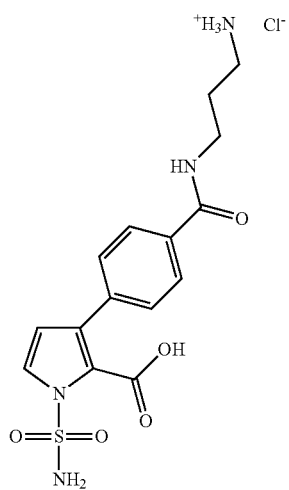 [SMILES: NS(=O)(=O)n1ccc(-c2ccc(C(=O)NCCC[NH3+])cc2)c1C(=O)O ; [Cl-]]

Step A: 4-[2-Benzyloxycarbonyl-1-(benzyloxycarbonylsulfamoyl)pyrrol-3-yl]benzoic acid, sodium salt XPhos Pd G2 (76 mg, 98 μmol) followed by a solution of potassium phosphate tribasic (621 mg, 2.93 mmol) in water (3 mL) was added to a solution of sodium [(benzyloxy)carbonyl]({2-[(benzyloxy)carbonyl]-3-bromo-1H-pyrrol-1-yl}sulfonyl)azanide (504 mg, 976 μmol) and 4-(4,4,5,5-tetramethyl-1,3,2-dioxaborolan-2-yl)benzoic acid (706 mg, 1.42 mmol) in 1,4-dioxane (10 mL) and the reaction mixture heated to 90° C. and stirred at this temperature for 4 hours. The reaction mixture was diluted with water (50 mL) and extracted with ethyl acetate (75 mL). The organic phase was dried over MgSO$_4$, filtered and the solvent removed under reduced pressure. DCM was added to the residue, the precipitate isolated by filtration and dried under vacuum to give the desired product as a white solid (140 mg, 26%).

$^1$H NMR (500 MHz, DMSO-$d_6$) δ 7.83 (d, J=8.0 Hz, 2H), 7.40-7.37 (m, 4H), 7.34-7.26 (m, 10H), 6.30 (d, J=3.0 Hz, 1H), 5.16 (s, 2H), 4.86 (s, 2H).

LC-MS (Method B): $R_T$=3.28 min, m/z=533.3 [M−H]$^-$.

Step B: Benzyl-1-(benzyloxycarbonylsulfamoyl)-3-[4-[3-(tert-butoxycarbonylamino)propylcarbamoyl]phenyl]pyrrole-2-carboxylate, Sodium Salt HBTU (106 mg, 281 μmol) was added to a solution of 4-[2-benzyloxycarbonyl-1-(benzyloxycarbonylsulfamoyl) pyrrol-3-yl]benzoic acid, sodium salt (125 mg, 224 μmol), tert-butyl N-(3-aminopropyl)carbamate (41 mg, 234 μmol) and N,N-diisopropylethylamine (91 mg, 702 μmol) in DMF (3 mL) and the reaction allowed to stir at room temperature overnight. The reaction was quenched by addition of water (50 mL), and ethyl acetate (75 mL) was added. The phases were separated and the aqueous phase extracted with ethyl acetate (100 mL). The combined organic phases were washed with brine (100 mL), dried over MgSO$_4$, filtered and the solvent removed under reduced pressure. Purification by column chromatography (silica, petroleum ether:ethyl acetate, gradient elution from 100:0 to 0:100) gave the desired product as a colourless oil (75 mg, 47%).

LC-MS (Method A): $R_T$=3.52 min, m/z=689.6 [M−H]$^-$.

Step C: Benzyl-3-[4-(3-aminopropylcarbamoyl)phenyl]-1-(benzyloxycarbonylsulfamoyl)pyrrole-2-carboxylate 4M HCl in 1,4-dioxane (10 mL) was added to a solution of benzyl 1-(benzyloxycarbonylsulfamoyl)-3-[4-[3-(tert-butoxycarbonylamino)propylcarbamoyl]phenyl]pyrrole-2-carboxylate, sodium salt (75 mg, 105 μmol) in DCM (5 mL) and the reaction mixture allowed to stir for 3 hours. The solvent was removed under reduced pressure, the reaction mixture loaded on to a 2 g SCX cartridge and eluted with methanol followed by 3M ammonia in methanol. The product fractions were combined and the solvent removed under reduced pressure to give the desired product as a white solid (52 mg, 84%).

$^1$H NMR (500 MHz, DMSO-$d_6$) δ 8.58 (t, J=6.0 Hz, 1H), 7.77 (d, J=8.5 Hz, 2H), 7.63 (br s, 3H), 7.43-7.39 (m, 4H), 7.34-7.26 (m, 9H), 6.30 (d, J=3.0, 1H), 5.16 (s, 2H), 4.86 (s, 2H), 3.37-3.30 (m, 2H), 2.85 (t, J=7.5 Hz, 2H), 1.81 (m, 2H). The multiplet at 3.37-3.30 is obscured by residual water peak.

LC-MS (Method B): $R_T$=2.60 min, m/z=589.5 [M−H]$^-$.

Step D: 3-[4-(3-Aminopropylcarbamoyl)phenyl]-1-sulfamoyl-pyrrole-2-carboxylic acid hydrochloride DCM (5 mL) was added to benzyl 3-[4-(3-aminopropylcarbamoyl)phenyl]-1-(benzyloxycarbonylsulfamoyl)pyrrole-2-carboxylate (52 mg, 88 μmol) followed by a solution of 4M HCl in 1,4-dioxane (0.8 mL) and the solvent removed under reduced pressure. To the residue was added methanol (10 mL) and 10% palladium on carbon (50% wet, 10 mg) and the reaction mixture placed under a hydrogen atmosphere for 2 hours. The reaction mixture was filtered through a pad of Celite® and eluted with methanol (150 mL). The solvent was removed under reduced pressure and trituration with a mixture of diethyl ether and petroleum ether gave the desired product as an off-white solid (22 mg, 62%).

$^1$H NMR (500 MHz, DMSO-$d_6$) δ 8.78-8.72 (m, 1H), 8.56 (br s, 2H), 7.99 (br s, 3H), 7.84 (d, J=8.0 Hz, 2H), 7.58 (d, J=8.0 Hz, 2H), 7.24 (s, 1H), 6.35 (d, J=2.5 Hz, 1H), 3.37-3.32 (m, 2H), 2.84 (t, J=7.0 Hz, 2H), 1.83 (quin, J=7.0 Hz, 2H). The multiplet at 3.37-3.32 is obscured by residual water peak.

LC-MS (Method A): $R_T$=1.80 min, m/z=365.3 [M−H]$^-$.

Example 52 (Sodium Salt): 3-(6-Oxo-1,6-dihydro-pyridin-3-yl)-1-sulfamoyl-1H-pyrrole-2-carboxylic acid, Sodium Salt

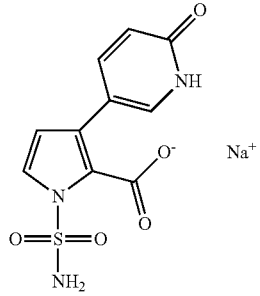 [SMILES: NS(=O)(=O)n1ccc(-c2ccc(=O)[nH]c2)c1C(=O)[O-] ; [Na+]]

Step A: Sodium [(benzyloxy)carbonyl]({2-[(benzyloxy)carbonyl]-3-[6-(benzyloxy)pyridin-3-yl]-1H-pyrrol-1-yl}sulfonyl)azanide A mixture of sodium [(benzyloxy)carbonyl]({2-[(benzyloxy)carbonyl]-3-bromo-1H-pyrrol-1-yl}sulfonyl)azanide (170 mg, 0.33 mmol), 6-(benzyloxy)pyridine-3-boronic acid (92 mg, 0.41 mmol) and sodium carbonate (109 mg, 1.02 mmol) in 1,4-dioxane (1.0 mL) and water (0.5 mL) was degassed by bubbling nitrogen for 5 minutes followed by the addition of Pd(dppf)Cl$_2$ (26 mg, 0.034 mmol). The resulting mixture was heated to 130° C. under microwave irradiation for 20 minutes. The reaction mixture was diluted with water (3 mL) and extracted into ethyl acetate (3×3 mL). The combined organic phases were washed with brine (3 mL), dried over MgSO$_4$, filtered and concentrated to dryness under reduced pressure. The residue was purified by column chromatography (silica, 0-100% ethyl acetate/DCM then 0-20% MeOH/ethyl acetate) then triturated with diethyl ether to afford the desired product as a tan solid (113 mg, 55%).

$^1$H NMR (500 MHz, DMSO-d$_6$) δ 8.16 (dd, J=2.5, 0.4 Hz, 1H), 7.65 (dd, J=8.6, 2.5 Hz, 1H), 7.47-7.44 (m, 2H), 7.41-7.36 (m, 4H), 7.34-7.24 (m, 10H), 6.80 (dd, J=8.6, 0.4 Hz, 1H), 6.23 (d, 3.2 Hz, 1H), 5.35 (s, 2H), 5.13 (s, 2H), 4.85 (s, 2H).

LC-MS (Method A): R$_T$=4.21 min, m/z=598.0 [M+H]$^+$.

Step B: 3-(6-Oxo-1,6-dihydropyridin-3-yl)-1-sulfamoyl-1H-pyrrole-2-carboxylic acid, Sodium Salt To a solution of sodium [(benzyloxy)carbonyl]({2-[(benzyloxy)carbonyl]-3-[6-(benzyloxy)pyridin-3-yl]-1H-pyrrol-1-yl}sulfonyl)azanide (113 mg, 0.18 mmol) in methanol (5 mL) was added 10% palladium on carbon (50% wet, 40 mg, 0.2 mmol) and the resulting suspension hydrogenated under 1 atmosphere hydrogen at room temperature for 6 hours. The reaction mixture was filtered through a pad of Celite® and concentrated under reduced pressure, triturated with diethyl ether and the remaining solid dried at 40° C. under vacuum to afford desired product as a brown solid (47 mg, 85%).

$^1$H NMR (500 MHz, DMSO-d$_6$) δ 11.56 (br s, 1H), 8.68 (br s, 2H), 7.66 (br s, 1H), 7.58 (dd, J=9.5, 2.8 Hz, 1H), 7.18 (br s, 1H), 6.27 (d, J=9.5 Hz, 1H), 6.23 (d, J=2.8 Hz, 1H).

LC-MS (Method D): R$_T$=0.41 min, m/z=284.1 [M+H]$^+$.

Example 53 (Hydrochloride Salt): 3-(2-Amino-1,3-benzothiazol-4-yl)-1-sulfamoyl-pyrrole-2-carboxylic acid hydrochloride

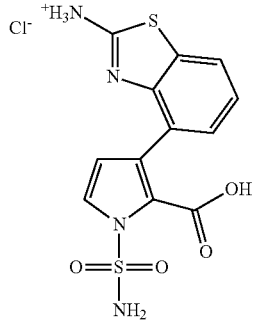 [SMILES: [Cl-] ; NS(=O)(=O)n1ccc(-c2cccc3sc([NH3+])nc23)c1C(=O)O]

Step A: tert-Butyl N-(4-bromo-1,3-benzothiazol-2-yl)-N-tert-butoxycarbonyl Carbamate 4-(Dimethylamino)pyridine (246 mg, 2.0 mmol) was added to a stirred suspension of 4-bromo-1,3-benzothiazol-2-amine (4.63 g, 20.2 mmol), triethylamine (2.8 mL, 20.2 mmol) and di-tert-butyl dicarbonate (9.70 g, 44.5 mmol) in DCM (100 mL) and stirred at room temperature for 17 hours. The reaction mixture was diluted with water (100 mL) and the resulting layers separated. The aqueous layer was washed with DCM (2×30 mL) and the extracts combined with the original organic layer, washed with 2M HCl$_{(aq)}$ (50 mL), dried over MgSO$_4$, filtered and concentrated under reduced pressure. The residue was purified by column chromatography (silica, petroleum ether:ethyl acetate, gradient elution from 100:0 to 70:30) to afford the desired product as an off white solid (3.97 g, 46%). This was used in next step without further purification.

LC-MS (Method A): R$_T$: 4.48 min, m/z=427.1/429.1 [M–H]$^-$.

Step B: [2-[Bis(tert-butoxycarbonyl)amino]-1,3-benzothiazol-4-yl]boronic acid A stirred solution of tert-butyl N-(4-bromo-1,3-benzothiazol-2-yl)-N-tert-butoxycarbonyl carbamate (1.5 g, 3.49 mmol), bis(pinacolato)diboron (1.77 g, 6.99 mmol), Pd(dppf)Cl$_2$ (128 mg, 175 µmol) and potassium acetate (1.03 g, 10.48 mmol) in 1,4-dioxane (9 mL) under a nitrogen atmosphere was heated at 85° C. for 3 hours. The reaction mixture was diluted with diethyl ether (20 mL) and filtered through Celite®. The filtrate was concentrated then re-dissolved in diethyl ether (20 mL) and washed with saturated sodium bicarbonate solution (3×10 mL). The organic extract was dried over Na$_2$SO$_4$, filtered, concentrated to dryness, redissolved in petroleum ether (20 mL) and filtered. The filtrate was concentrated and purified by column chromatography (silica, petroleum ether:ethyl acetate, gradient elution from 90:10 to 80:20) then triturated with petroleum ether and filtered to give the desired product as a solid (595 mg, 43%).

$^1$H NMR (500 MHz, CDCl$_3$) δ 7.94 (dd, J=7.2, 1.1 Hz, 1H), 7.88 (dd, J=7.9, 1.1 Hz, 1H), 7.36 (t, J=7.6 Hz, 1H), 6.55 (s, 2H), 1.62 (s, 18H).

Step C: Benzyl 1-(benzyloxycarbonylsulfamoyl)-3-[2-[bis(tert-butoxycarbonyl)amino]-1,3-benzothiazol-4-yl]pyrrole-2-carboxylate A solution of sodium [(benzyloxy)carbonyl]({2-[(benzyloxy)carbonyl]-3-bromo-1H-pyrrol-1-yl}sulfonyl)azanide (500 mg, 970 μmol), [2-[bis(tert-butoxycarbonyl)amino]-1,3-benzothiazol-4-yl]boronic acid (421 mg, 1.07 mmol), XPhos Pd G2 (76 mg, 97 μmol) and potassium phosphate tribasic (618 mg, 2.91 mmol) in a mixture of DME (4 mL) and water (1 mL) under a nitrogen atmosphere was heated at 45° C. by microwave irradiation for 3 hours. The organic layer was separated, concentrated to dryness under reduced pressure and the residue triturated with diethyl ether and filtered. The resulting solid was partitioned between DCM and 1M HCl$_{(aq)}$, the layers separated and the organic layer concentrated to give the desired product as a solid (600 mg, 81%).

$^1$H NMR (500 MHz, CDCl$_3$) δ 7.71-7.55 (m, 2H), 7.31 (br s, 1H), 7.25-7.16 (m, 6H), 7.07-6.96 (m, 3H), 6.57 (br d, J=6.7 Hz, 2H), 6.20 (d, J=2.7 Hz, 1H), 4.95 (s, 2H), 4.67 (s, 2H), 1.43 (s, 18H).

Step D: 3-[2-[Bis(tert-butoxycarbonyl)amino]-1,3-benzothiazol-4-yl]-1-sulfamoyl-pyrrole-2-carboxylic acid Benzyl-1-(benzyloxycarbonylsulfamoyl)-3-[2-[bis(tert-butoxycarbonyl)amino]-1,3-benzothiazol-4-yl]pyrrole-2-carboxylate (600 mg, 786 μmol) was hydrogenated in a similar manner to 3-(6-aminopyridin-3-yl)-1-sulfamoyl-1H-pyrrole-2-carboxylic acid, sodium salt (Step B) to give the desired product as an oil (357 mg, 84%).

$^1$H NMR (500 MHz, DMSO-d$_6$) δ 7.89 (d, J=7.8 Hz, 1H), 7.52 (br d, J=7.5 Hz, 1H), 7.30 (t, J=7.8 Hz, 1H), 7.15 (br s, 1H), 6.42 (d, J=3.1 Hz, 1H), 1.52 (s, 18H).

LC-MS (Method A): R$_T$=3.89 min, m/z=537.3 [M-H]$^-$.

Step E: 3-(2-Amino-1,3-benzothiazol-4-yl)-1-sulfamoyl-pyrrole-2-carboxylic acid hydrochloride To a stirred solution of 3-[2-[bis(tert-butoxycarbonyl)amino]-1,3-benzothiazol-4-yl]-1-sulfamoyl-pyrrole-2-carboxylic acid (132 mg, 245 μmol) in DCM (3 mL) was added TFA (0.6 mL, 8.10 mmol). After 2 hours, the reaction mixture was quenched with methanol, diluted with ethyl acetate, concentrated and redissolved in diethyl ether. To this was added 4M HCl in 1,4-dioxane and the resulting precipitate isolated by filtration and rinsed with diethyl ether to give the desired product as a white solid (68 mg, 66%).

$^1$H NMR (500 MHz, DMSO-d$_6$) δ 8.33-8.24 (m, 1H), 8.20 (s, 2H), 7.77 (br d, J=6.6 Hz, 1H), 7.53 (d, J=2.7 Hz, 1H), 7.37 (br s, 1H), 7.27 (s, 1H), 7.23-7.16 (m, 3H), 6.36 (d, J=3.1 Hz, 1H).

LC-MS (Method A): R$_T$=2.29 min, m/z=337.2 [M-H]$^-$.

Example 54 (Free Acid): 3-Benzyl-1-sulfamoyl-1H-pyrrole-2-carboxylic acid

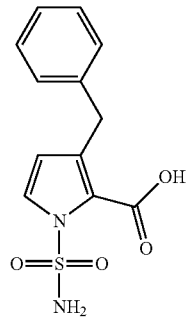 [SMILES: NS(=O)(=O)n1ccc(Cc2ccccc2)c1C(=O)O]

Step A: Methyl 3-benzyl-1H-pyrrole-2-carboxylate

Methyl 2-isocyanoacetate (1.8 mL, 20.2 mmol) and (prop-2-yn-1-yl)benzene (2.1 mL, 16.8 mmol) were added to NMP (30 mL), to this was added silver carbonate (463 mg, 1.68 mmol) and the mixture was heated at 80° C. for 2 hours. The mixture was filtered, quenched with water (100 mL), extracted with diethyl ether (2×100 mL), dried over MgSO$_4$, filtered and the solvent evaporated to afford a black liquid. The residue was purified by column chromatography (silica, 40-100% diethyl ether in petroleum ether) to afford the desired product as an orange liquid (1.7 g, 47%).

$^1$H NMR (500 MHz, CHLOROFORM-d) δ 8.96 (br s, 1H), 7.29-7.22 (m, 4H), 7.20-7.15 (m, 1H), 6.82 (t, J=2.8 Hz, 1H), 6.04 (t, J=2.7 Hz, 1H), 4.18 (s, 2H), 3.86 (s, 3H).

Step B: 3-Benzyl-1H-pyrrole-2-carboxylic acid

Methyl 3-benzyl-1H-pyrrole-2-carboxylate (1.0 g, 4.65 mmol) was dissolved in ethanol (25 mL) and water (7.5 mL) to this was added lithium hydroxide monohydrate (292.43 mg, 6.97 mmol) and the mixture was stirred at 60° C. for 5 hours and then at 25° C. for 38 hours. The reaction was evaporated to 50% the initial volume, diluted with water (50 mL) and the aqueous layer washed with diethyl ether (75 mL). The aqueous layer was then acidified with 2M HCl$_{(aq)}$ to give a solid which was filtered and air dried overnight to afford the desired product as a white solid (700 mg, 75%).

$^1$H NMR (500 MHz, DMSO-d$_6$) δ 12.26 (br s, 1H), 11.46 (br s, 1H), 7.28-7.19 (m, 4H), 7.18-7.11 (m, 1H), 6.81 (t, J=2.8 Hz, 1H), 5.92 (t, J=2.7 Hz, 1H), 4.08 (s, 2H).

Step C: Benzyl 3-benzyl-1H-pyrrole-2-carboxylate

3-Benzyl-1H-pyrrole-2-carboxylic acid (680 mg, 3.38 mmol), benzyl bromide (606 mg, 3.55 mmol) and sodium hydrogen carbonate (369 mg, 4.39 mmol) were added to DMF (30 mL) and heated at 50° C. for 5 hours. The mixture was quenched with water (100 mL), extracted with diethyl ether (2×75 mL), dried over MgSO$_4$, filtered and the solvent was evaporated to afford a yellow gum. The gum was purified by column chromatography (silica, diethyl ether and then 1:1 diethyl ether in ethyl acetate) to afford the desired product as a yellow solid (700 mg, 57%). This was used in the subsequent step without further purification.

LC-MS (Method B): R$_T$=3.91 min, m/z=290.3 [M-H]$^-$.

Step D: Benzyl 1-({[(benzyloxy)carbonyl]amino}sulfonyl)-3-benzyl-1H-pyrrole-2-carboxylate Benzyl 3-benzyl-1H-pyrrole-2-carboxylate (430 mg, 1.48 mmol) was dissolved in THF (20 mL) and to this was added sodium hydride (60% in mineral oil, 106 mg, 2.21 mmol) before stirring for 10 minutes under nitrogen. To this was added [(benzyloxy)carbonyl]({[4-(dimethyliminiumyl)-1,4-dihydropyridin-1-yl]sulfonyl})azanide (496 mg, 1.48 mmol) in one portion and the mixture was stirred at reflux for 18 hours. The mixture was quenched with 2M HCl$_{(aq)}$ (50 mL) and water (50 mL), extracted with diethyl ether (2×75 mL), dried over MgSO$_4$, filtered and the solvent evaporated to afford a black gum. The mixture was purified by column chromatography (silica, 20% to 40% diethyl ether in petroleum ether, 100% diethyl ether and finally 1:1 diethyl ether:ethyl acetate) to afford the desired product as a dark gum (350 mg, 46%).

LC-MS (Method B): R$_T$=2.44 min, m/z=503.2 [M−H]$^-$.

Step E: 3-Benzyl-1-sulfamoyl-1H-pyrrole-2-carboxylic acid

Benzyl 3-benzyl-1-(benzyloxycarbonylsulfamoyl)pyrrole-2-carboxylate (350 mg, 693 µmol) and 10% palladium on carbon (50% wet, 7.4 mg, 69 µmol) were added to ethanol (20 mL) and stirred under an atmosphere of hydrogen gas (700 mg, 346 mmol) for 2 hours. The mixture was filtered through Celite® and evaporated to afford a yellow gum. This was dissolved in a minimum amount of diethyl ether (1 mL), to this was added 20% diethyl ether in petroleum ether to afford a solid which was sonicated, filtered and air dried to afford the desired product as a white solid (90 mg, 44%).

$^1$H NMR (500 MHz, DMSO-d$_6$) δ 8.89 (br s, 2H), 7.28-7.19 (m, 4H), 7.18-7.10 (m, 2H), 5.90 (d, J=3.1 Hz, 1H), 4.10 (s, 2H).

LC-MS (Method E): R$_T$=0.71 min, m/z=279.2 [M−H]$^-$.

Further Examples

The following examples were prepared in a similar manner to 3-benzyl-1-sulfamoyl-1H-pyrrole-2-carboxylic acid starting from methyl 2-isocyanoacetate and the corresponding alkyne.

Example 56 (free acid): 3-(Anilinomethyl)-1-sulfamoyl-pyrrole-2-carboxylic acid

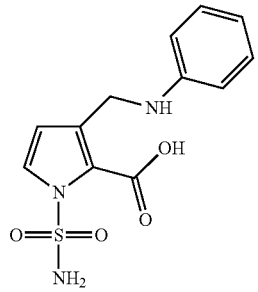

Step A: Benzyl 3-[(N-tert-butoxycarbonylanilino)methyl]-1H-pyrrole-2-carboxylate Under an inert atmosphere, tert-butyl N-phenyl-N-prop-2-ynyl-carbamate (1.0 g, 4.32 mmol) and silver carbonate (596 mg, 2.16 mmol) were suspended in anhydrous 1,4-dioxane (20 mL), and heated to 100° C. A solution of benzyl 2-isocyanoacetate (757 mg, 4.32 mmol) in anhydrous 1,4-dioxane (5 mL) was added dropwise over 1 hour and after complete addition the mixture was surrounded with aluminium foil then heated at 100° C. for 19 hours. Following cooling, the reaction mixture was filtered through Celite® and washed with diethyl ether (100 mL). The phases were separated and the aqueous phase extracted with diethyl ether (100 mL). The combined organic phases were washed with brine (150 mL), dried over MgSO$_4$ and filtered. The solvent was removed under reduced pressure and the residue purified by column chromatography (silica, petroleum ether:diethyl ether, gradient elution from 100:0 to 0:100) to give the desired product as an off-white solid (1.22 g, 69%).

$^1$H NMR (500 MHz, CDCl$_3$) δ 8.95 (br s, 1H), 7.37-7.31 (m, 5H), 7.24-7.21 (m, 2H), 7.17 (m, 2H), 7.11 (m, 1H), 6.86 (t, J=2.5 Hz, 1H), 6.33 (t, J=2.5 Hz, 1H), 5.21 (s, 2H), 5.07 (s, 2H), 1.43 (s, 9H).

LC-MS (Method B): R$_T$=4.14 min, m/z=405.4 [M−H]$^-$.

| Example | Structure | Name | Analytical Data |
|---|---|---|---|
| Example 55 (free acid) | 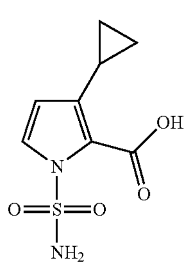 [SMILES: NS(=O)(=O)n1ccc(C2CC2)c1C(=O)O] | 3-Cyclopropyl-1-sulfamoyl-1H-pyrrole-2-carboxylic acid | $^1$H NMR (500 MHz, DMSO-d$_6$) δ 8.24 (br s, 2H), 7.25 (br s, 1H), 5.80 (br s, 1H), 2.60-2.54 (m, 1H), 0.84-0.94 (m, 2H), 0.45-0.60 (m, 2H). LC-MS (Method D): R$_T$ = 3.29 min, m/z = 229.1 [M − H]$^-$. |

Step B: Benzyloxycarbonyl-[2-benzyloxycarbonyl-3-[(N-tert-butoxycarbonylanilino)methyl]pyrrol-1-yl]sulfonyl-azanide, sodium salt A suspension of sodium hydride (60% in mineral oil, 360 mg, 9.00 mmol) in anhydrous THF (15 mL) was cooled to −10° C. under a nitrogen atmosphere followed by the dropwise addition of a solution of benzyl 3-[(N-tert-butoxycarbonylanilino)methyl]-1H-pyrrole-2-carboxylate (1.22 g, 3.00 mmol) in anhydrous THF (10 mL) over a period of 30 minutes ensuring the temperature was maintained below −5° C. The reaction mixture was allowed to warm to room temperature and stirred for 1 hour before re-cooling to −10° C. To the reaction mixture was added benzyl N-chlorosulfonylcarbamate (821 mg, 3.30 mmol) ensuring that the temperature was maintained below −5° C. The reaction mixture was allowed to warm to room temperature and stirred for 1 hour. The reaction mixture was re-cooled to −10° C., quenched by the dropwise addition of 50:50 water:brine (100 mL) and extracted into ethyl acetate (100 mL). The organic phase was dried over MgSO$_4$, filtered and the solvent removed under reduced pressure. Purification by column chromatography (silica, petroleum ether:ethyl acetate, gradient elution from 100:0 to 0:100) gave the desired product as a white solid (750 mg, 39%).
$^1$H NMR (500 MHz, DMSO-d$_6$) δ 7.48-7.42 (m, 2H), 7.32-7.23 (m, 11H), 7.14-7.10 (m, 3H), 6.59 (d, J=2.5 Hz, 1H), 5.14 (s, 2H), 4.87 (s, 2H), 4.78 (s, 2H), 1.35 (s, 9H).
LC-MS (Method B): R$_T$=2.73 min, m/z=618.5 [M−H]$^-$.

Step C: Benzyl 3-(anilinomethyl)-1-(benzyloxycarbonylsulfamoyl)pyrrole-2-carboxylate 4M HCl in 1,4-dioxane (15 mL) was added to a solution of benzyloxycarbonyl-[2-benzyloxycarbonyl-3-[(N-tert-butoxycarbonylanilino)methyl]pyrrol-1-yl]sulfonyl-azanide, sodium salt (750 mg, 1.21 mmol) in DCM (5 mL), the reaction mixture allowed to stir for 3 hours then heated to 50° C. for 1 hour. The solvent was removed under reduced pressure, DCM (70 mL) and water (70 mL) added, the phases separated and the aqueous phase extracted with DCM (50 mL). The combined organic phases were dried over MgSO$_4$, filtered and the solvent removed under reduced pressure. Purification by column chromatography (silica, petroleum ether:ethyl acetate, gradient elution from 90:10 to 0:100) gave the desired product as an orange oil (350 mg, 56%). $^1$H NMR (500 MHz, DMSO-d$_6$) δ 7.53-7.48 (m, 2H), 7.42 (s, 1H), 7.45-7.30 (m, 10H), 7.06 (t, J=7.5 Hz, 2H), 6.63-6.58 (m, 3H), 6.22 (d, J=3.0 Hz, 1H), 5.33 (s, 2H), 5.05 (s, 2H), 4.28 (s, 2H). LC-MS (Method B): R$_T$=2.59 min, m/z=518.4 [M−H]$^-$.

Step D: 3-(Anilinomethyl)-1-sulfamoyl-pyrrole-2-carboxylic acid

Benzyl 3-(anilinomethyl)-1-(benzyloxycarbonylsulfamoyl)pyrrole-2-carboxylate (350 mg, 674 µmol) was hydrogenated in a similar manner to 3-(6-aminopyridin-3-yl)-1-sulfamoyl-1H-pyrrole-2-carboxylic acid, sodium salt (Step B) to give the desired product as a beige solid (102 mg, 44%). $^1$H NMR (500 MHz, DMSO-d$_6$) δ 8.34 (br s, 2H), 7.29 (d, J=3.0 Hz, 1H), 7.12-7.00 (m, 2H), 6.57 (d, J=8.0 Hz, 2H), 6.55-6.45 (m, 1H), 6.17 (d, J=3.0 Hz, 1H), 4.36 (s, 2H). LC-MS (Method A): R$_T$=1.99 min, m/z=294.3 [M−H]$^-$.

Example 57 (Hydrochloride Salt): 3-(Piperidin-4-yl)-1-sulfamoyl-1H-pyrrole-2-carboxylic acid hydrochloride

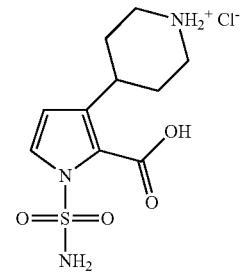

Benzyl 1-(benzyloxycarbonylsulfamoyl)-3-(4-piperidyl)pyrrole-2-carboxylate hydrochloride (100 mg, 0.19 mmol) was dissolved in methanol (10 mL) and stirred under an atmosphere of nitrogen. The reaction mixture was purged with vacuum and the atmosphere replaced with nitrogen three times. 10% Palladium on carbon (50% wet, 79.71 mg, 0.04 mmol) was added to the reaction mixture, the atmosphere purged with vacuum and replaced with hydrogen (1 atmosphere, balloon) and the reaction mixture allowed to stir for 6 hours at room temperature. The reaction mixture was filtered through a pre-conditioned Celite® pad (methanol) and washed with methanol (2×30 mL). The filtrate was concentrated under reduced pressure to afford a white solid. The solid was triturated with diethyl ether (3×10 mL) and dried under reduced pressure to give the desired product as a white solid (41 mg, 68%).
$^1$H NMR (500 MHz, METHANOL-d$_4$) δ 7.47 (d, J=3.2 Hz, 1H), 6.25 (d, J=3.2 Hz, 1H), 3.56 (tt, J=12.1, 3.5 Hz, 1H), 3.50-3.45 (m, 2H), 3.11 (td, J=13.1, 2.5 Hz, 2H), 2.09 (brd, J=13.2 Hz, 2H), 1.85 (qd, J=13.2, 3.8 Hz, 2H).
LCMS (Method C): R$_T$=0.65 min, m/z=274.1 [M+H]$^+$.

Example 58 (free acid): 3-(1-Acetylpiperidin-4-yl)-1-sulfamoyl-1H-pyrrole-2-carboxylic acid

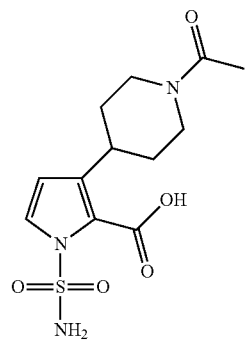 [SMILES: CC(=O)N1CCC(c2ccn(S(N)(=O)=O)c2C(=O)O)CC1]

Step A: Benzyl 3-(1-acetylpiperidin-4-yl)-1-({[(benzyloxy)carbonyl]amino}sulfonyl)-1H-pyrrole-2-carboxylate To a solution of benzyl 1-(benzyloxycarbonylsulfamoyl)-3-(4-piperidyl)pyrrole-2-carboxylate hydrochloride (60 mg, 112 µmol) in DCM (10 mL) at 0° C. was added triethylamine (39 µL, 281 µmol,) followed by acetyl chloride (9.6 µL, 135 µmol) and the reaction was allowed to stir at 0° C. for 5 hours. The reaction mixture was diluted with DCM (20 mL), washed with saturated aqueous ammonium chloride (20 mL), 1M $HCl_{(aq)}$ (20 mL), water (20 mL), brine (20 mL), dried over $MgSO_4$, filtered and concentrated to dryness. The residue was purified by column chromatography (silica, petroleum ether:ethyl acetate, gradient elution from 100:0 to 0:100) to give the desired product as a white solid (28 mg, 46%).

$^1$H NMR (500 MHz, $CDCl_3$) δ 7.51 (brs, 1H), 7.38-7.20 (m, 3H), 7.19-7.04 (m, 8H), 5.78 (br s, 1H), 4.99 (br s, 2H), 4.86 (s, 2H), 4.41 (br d, J=12.9 Hz, 1H), 3.58-3.45 (m, 1H), 2.91 (br t, J=11.8 Hz, 1H), 2.41 (br t, J=12.8 Hz, 1H), 1.98 (s, 3H), 1.92 (br s, 1H), 1.52-1.33 (m, 2H), 1.32-1.13 (m, 2H).

LC-MS (Method A): $R_T$=2.90 min, m/z=540.0 $[M+H]^+$.

Step B: 3-(1-Acetylpiperidin-4-yl)-1-sulfamoyl-1H-pyrrole-2-carboxylic acid

Benzyl-3-(1-acetylpiperidin-4-yl)-1-({[(benzyloxy)carbonyl]amino}sulfonyl)-1H-pyrrole-2-carboxylate (28 mg, 52 µmol) was hydrogenated in a similar manner to 3-(6-aminopyridin-3-yl)-1-sulfamoyl-1H-pyrrole-2-carboxylic acid, sodium salt (Step B) to give the desired product as a pale yellow solid (13 mg, 70%).

$^1$H NMR (500 MHz, $CD_3OD$) δ 7.20-7.14 (m, 1H), 6.08 (d, J=2.5 Hz, 1H), 4.59 (br d, J=11.7 Hz, 1H), 3.95 (br d, J=11.3 Hz, 1H), 3.60 (br s, 1H), 3.27-3.07 (m, 1H), 2.65 (br t, J=12.8 Hz, 1H), 2.11 (s, 3H), 1.89 (br d, J=12.3 Hz, 1H), 1.83 (br d, J=12.6 Hz, 1H), 1.62-1.43 (m, 2H).

LC-MS (Method D): $R_T$=0.43 min, m/z=314.1 $[M-H]^-$.

Example 59 (free acid): 3-(1-Methylsulfonyl-4-piperidyl)-1-sulfamoyl-pyrrole-2-carboxylic acid

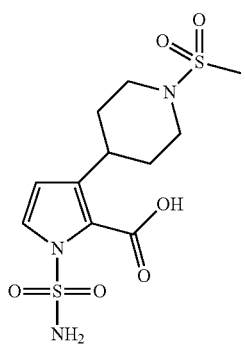 [SMILES: CS(=O)(=O)N1CCC(c2ccn(S(N)(=O)=O)c2C(=O)O)CC1]

Step A: Benzyl 3-(1-methylsulfonyl-4-piperidyl)-1H-pyrrole-2-carboxylate

A suspension of benzyl 3-(4-piperidyl)-1H-pyrrole-2-carboxylate hydrochloride (286 mg, 0.89 mmol) in DCM (5 mL) was cooled to 0° C. Triethylamine (310 µL, 2.23 mmol) was added followed by methanesulfonyl chloride (83 µL, 1.07 mmol). After 5 hours the mixture was diluted with DCM (50 mL), washed with 2M $HCl_{(aq)}$ (20 mL), dried over $Na_2SO_4$, filtered and evaporated under reduced pressure. Purification by column chromatography (silica, petroleum ether:diethyl ether, gradient elution from 100:0 to 0:100) gave the desired product as a white solid (246 mg, 76%).

$^1$H NMR (500 MHz, $CDCl_3$) δ=8.95 (br s, 1H), 7.44-7.32 (m, 5H), 6.86 (t, J=2.4 Hz, 1H), 6.17 (t, J=2.4 Hz, 1H), 5.29 (s, 2H), 3.89-3.77 (m, 2H), 3.32-3.20 (m, 1H), 2.77 (s, 3H), 2.68-2.56 (m, 2H), 1.99-1.88 (m, 2H), 1.76-1.66 (m, 2H).

LC-MS (Method A): $R_T$=0.46 min, m/z=361.2 $[M-H]^-$.

Step B: Benzyl 1-(benzyloxycarbonylsulfamoyl)-3-(1-methylsulfonyl-4-piperidyl)pyrrole-2-carboxylate A solution of benzyl 3-(1-methylsulfonyl-4-piperidyl)-1H-pyrrole-2-carboxylate (246 mg, 0.68 mmol) in anhydrous THF (4 mL) was cooled to 0° C. Sodium hydride (60% in mineral oil, 81 mg, 2.04 mmol) was added in one portion. After 5 minutes the reaction was warmed to room temperature and stirred for 60 minutes. After cooling to 0° C., benzyl N-chlorosulfonylcarbamate (186 mg, 0.75 mmol) was added in one portion and the reaction warmed to room temperature. After 2 hours saturated aqueous ammonium chloride (5 mL) was added quickly dropwise followed by ethyl acetate (60 mL). The organic was washed with water (10 mL), brine (5 mL), dried over $Na_2SO_4$, filtered and evaporated under reduced pressure. Purification by column chromatography (silica, DCM:ethyl acetate, gradient elution from 100:0 to 0:100) followed by column chromatography (silica, petroleum ether:ethyl acetate, gradient elution from 25:75 to 0:100) gave the desired product as a white solid (177 mg, 45%).

$^1$H NMR (500 MHz, DMSO-$d_6$) δ=7.58-7.50 (m, 2H), 7.39-7.25 (m, 10H), 6.10-5.99 (m, 1H), 5.21 (s, 2H), 4.87 (s, 2H), 3.57-3.50 (m, 2H), 3.42-3.28 (m, 1H), 2.90-2.77 (m, 5H), 1.74-1.67 (m, 2H), 1.60-1.48 (m, 2H). Multiplet at 3.42-3.28 partially obscured by water peak.

LC-MS (Method A): $R_T$=3.38 min, m/z=574.3 $[M-H]^-$.

Step C: 3-(1-Methylsulfonyl-4-piperidyl)-1-sulfamoyl-pyrrole-2-carboxylic acid

Benzyl-1-(benzyloxycarbonylsulfamoyl)-3-(1-methylsulfonyl-4-piperidyl)pyrrole-2-carboxylate (177 mg, 0.31 mmol) was hydrogenated in a similar manner to 3-(6-aminopyridin-3-yl)-1-sulfamoyl-1H-pyrrole-2-carboxylic acid, sodium salt (Step B) to give the desired product as a white solid (96 mg, 84%).

$^1$H NMR (500 MHz, DMSO-$d_6$) δ=13.30 (br s, 1H), 8.03 (br s, 2H), 7.39 (d, J=3.2 Hz, 1H), 6.32 (d, J=3.2 Hz, 1H), 3.67-3.60 (m, 2H), 3.25-3.16 (m, 1H), 2.89 (s, 3H), 2.81-2.73 (m, 2H), 1.85-1.79 (m, 2H), 1.69-1.58 (m, 2H).

LC-MS (Method A): $R_T$=0.66 min, m/z=350.2 $[M-H]^-$.

Further Examples

The following examples were prepared in a similar manner to 3-(1-methylsulfonyl-4-piperidyl)-1-sulfamoyl-pyrrole-2-carboxylic acid starting from benzyl 3-(4-piperidyl)-1H-pyrrole-2-carboxylate hydrochloride.

| Example | Structure | Name | Analytical Data |
|---|---|---|---|
| Example 60 (free acid) | 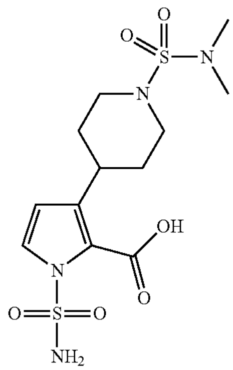 [SMILES: CN(C)S(=O)(=O)N1CCC(c2ccn(S(N)(=O)=O)c2C(=O)O)CC1] | 3-[1-(Dimethylsulfamoyl)-4-piperidyl]-1-sulfamoyl-pyrrole-2-carboxylic acid | $^1$H NMR (500 MHz, DMSO-$d_6$) δ = 9.34 (br s, 2H), 7.00 (d, J = 2.9 Hz, 1H), 5.99 (d, J = 2.9 Hz, 1H), 3.67-3.56 (m, 2H), 3.54-3.43 (m, 1H), 2.89-2.80 (m, 2H), 2.77 (s, 6H), 1.82-1.71 (m, 2H), 1.60-1.44 (m, 2H). LC-MS (Method A): $R_T$ = 0.46 min, m/z = 379.2 [M − H]$^-$. |
| Example 61 (free acid) | 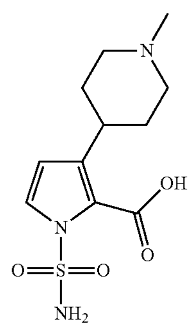 [SMILES: CN1CCC(c2ccn(S(N)(=O)=O)c2C(=O)O)CC1] | 3-(1-Methyl-4-piperidyl)-1-sulfamoyl-pyrrole-2-carboxylic acid | $^1$H NMR (500 MHz, CD$_3$OD) δ = 7.04-7.01 (m, 1H), 5.99-5.96 (m, 1H), 3.29-3.18 (m, 1H), 2.94-2.87 (m, 2H), 2.27 (s, 3H), 2.21-2.12 (m, 2H), 1.80-1.73 (m, 2H), 1.64-1.54 (m, 2H). Multiplet at 3.29-3.18 partially obscured by residual solvent. LC-MS (Method A): $R_T$ = 0.69 min, m/z = 286.3 [M − H]$^-$. |

Example 62 (free acid): 3-[1-(2-Aminoacetyl)-4-piperidyl]-1-sulfamoyl-pyrrole-2-carboxylic acid

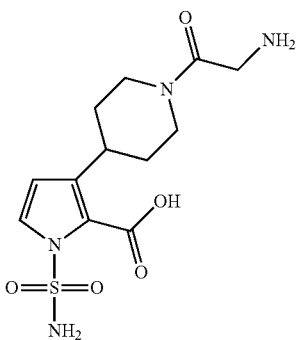 [SMILES: NCC(=O)N1CCC(c2ccn(S(N)(=O)=O)c2C(=O)O)CC1]

Step A: Benzyl-3-[1-[2-(tert-butoxycarbonylamino) acetyl]-4-piperidyl]-1H-pyrrole-2-carboxylate Benzyl 3-(4-piperidyl)-1H-pyrrole-2-carboxylate hydrochloride (200 mg, 0.62 mmol) and 2-(tert-butoxycarbonylamino)acetic acid (109 mg, 0.62 mmol) suspended in DMF (1.60 mL) were cooled to 0° C. N,N-Diisopropylethylamine (390 µL, 2.24 mmol) was added followed by HBTU (283 mg, 0.75 mmol). After stirring for 30 minutes at 0° C. the solution was allowed to warm to room temperature and stirred for 18 hours. Diethyl ether (40 mL) was added and the organics washed with water (2×10 mL), brine (10 mL), dried over Na$_2$SO$_4$, filtered and evaporated under reduced pressure. Purification by column chromatography (silica, DCM:ethyl acetate, gradient elution from 100:0 to 25:75) gave the desired product as a white foam (247 mg, 90%).

$^1$H NMR (500 MHz, CDCl$_3$) δ=8.97 (br s, 1H), 7.43-7.32 (m, 5H), 6.86-6.83 (m, 1H), 6.14-6.10 (m, 1H), 5.60-5.53 (m, 1H), 5.33-5.25 (m, 2H), 4.69-4.61 (m, 1H), 4.03-3.88 (m, 2H), 3.72-3.65 (m, 1H), 3.45-3.37 (m, 1H), 3.03-2.93 (m, 1H), 2.63-2.54 (m, 1H), 1.95-1.86 (m, 2H), 1.48-1.42 (m, 11H).

LC-MS (Method A): $R_T$=3.49 min, m/z=440.4 [M−H]$^-$.

Step B: Benzyl 1-(benzyloxycarbonylsulfamoyl)-3-[1-[2-(tert-butoxycarbonylamino)acetyl]-4-piperidyl] pyrrole-2-carboxylate Under inert atmosphere, a stirred suspension of sodium hydride (60% in mineral oil, 104 mg, 2.60 mmol) in anhydrous THF (1.22 mL) was cooled to −10° C. A solution of benzyl 3-[1-[2-(tert-butoxycarbonylamino)acetyl]-4-piperidyl]-1H-pyrrole-2-carboxylate (244 mg, 553 µmol) in THF (1.2 mL) was added dropwise over 10 minutes. The mixture was warmed to room temperature and stirred for 1 hour then cooled to −10° C. Benzyl N-chlorosulfonylcarbamate (241 mg, 0.97 mmol) was added in portions as a solid over 5 minutes. The mixture was warmed to room temperature, stirred for 2 hours, cooled to −10° C. and saturated aqueous ammonium chloride (3 mL) added. Ethyl acetate (50 mL) was added and the organic washed with water (2×10 mL), brine (10 mL), dried over Na$_2$SO$_4$, filtered and evaporated under reduced pressure. Purification by column chromatography (silica, DCM:methanol, gradient elution from 100:0 to 20:80) gave the desired product as a white solid (204 mg, 56%).

$^1$H NMR (500 MHz, DMSO-$d_6$) δ=7.58-7.52 (m, 2H), 7.37-7.21 (m, 10H), 6.70-6.65 (m, 1H), 5.98-5.94 (m, 1H), 5.21 (s, 2H), 4.86 (s, 2H), 4.42-4.31 (m, 1H), 3.84-3.71 (m, 3H), 2.99-2.90 (m, 1H), 2.88-2.78 (m, 1H), 2.42-2.32 (m, 1H), 1.68-1.59 (m, 2H), 1.42-1.35 (m, 11H).

LC-MS (Method A): $R_T$=3.76 min, m/z=653.5 [M−H]$^-$.

Step C: Benzyl 3-[1-(2-aminoacetyl)-4-piperidyl]-1-(benzyloxycarbonylsulfamoyl)pyrrole-2-carboxylate 4M HCl in 1,4-dioxane (660 μL, 2.63 mmol) was added to a solution benzyl 1-(benzyloxycarbonylsulfamoyl)-3-[1-[2-(tert-butoxycarbonylamino)acetyl]-4-piperidyl]pyrrole-2-carboxylate (202 mg, 0.31 mmol) in DCM (2 mL) and stirred at room temperature for 18 hours. All volatiles were removed under reduced pressure. Purification by column chromatography (silica, DCM:1M ammonia in methanol, gradient elution from 100:0 to 50:50) gave the desired product as a white solid (128 mg, 75%).

$^1$H NMR (500 MHz, DMSO-$d_6$) δ=7.58-7.52 (m, 2H), 7.70-7.40 (m, 9H), 7.32 (br s, 3H), 5.93-5.90 (m, 1H), 5.20 (s, 2H), 4.84 (s, 2H), 4.44-4.37 (m, 1H), 3.85-3.67 (m, 3H), 3.02-2.87 (m, 2H), 2.54-2.44 (m, 1H), 1.72-1.65 (m, 2H), 1.53-1.42 (m, 1H), 1.37-1.26 (m, 1H). The multiplet at 2.54-2.44 is partially obscured by residual solvent signal.

LC-MS (Method A): $R_T$=2.83 min, m/z=553.4 [M−H]$^-$.

Step D: 3-[1-(2-Aminoacetyl)-4-piperidyl]-1-sulfamoyl-pyrrole-2-carboxylic acid

Benzyl-3-[1-(2-aminoacetyl)-4-piperidyl]-1-(benzyloxycarbonylsulfamoyl)pyrrole-2-carboxylate (128 mg, 230 μmol) was hydrogenated in a similar manner to 3-(6-aminopyridin-3-yl)-1-sulfamoyl-1H-pyrrole-2-carboxylic acid, sodium salt (Step B) with 7M ammonia in methanol as a co-solvent to give the desired product as a white solid (71 mg, 89%).

$^1$H NMR (500 MHz, DMSO-$d_6$) δ=7.95 (br s, 5H), 7.02-6.96 (m, 1H), 5.97-5.91 (m, 1H), 4.52-4.40 (m, 1H), 3.81-3.69 (m, 3H), 3.66-3.57 (m, 1H), 3.08-2.98 (m, 1H), 2.67-2.59 (m, 1H), 1.80-1.72 (m, 2H), 1.59-1.26 (m, 2H).

LC-MS (Method A): $R_T$=0.80 min, m/z=329.3 [M−H]$^-$.

Further Examples

The following examples were prepared in a similar manner to 3-[1-(2-aminoacetyl)-4-piperidyl]-1-sulfamoyl-pyrrole-2-carboxylic acid starting from benzyl 3-(4-piperidyl)-1H-pyrrole-2-carboxylate hydrochloride.

Example 64 (hydrochloride salt): 3-[1-(2-Amino-2-methyl-propanoyl)-4-piperidyl]-1-sulfamoyl-pyrrole-2-carboxylic acid hydrochloride

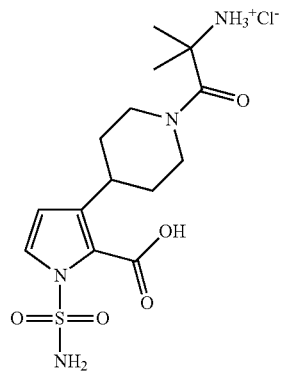

Step A: Benzyl 1-(benzyloxycarbonylsulfamoyl)-3-[1-[2-(tert-butoxycarbonylamino)-2-methyl-propanoyl]-4-piperidyl]pyrrole-2-carboxylate Benzyl-1-(benzyloxycarbonylsulfamoyl)-3-(4-piperidyl)pyrrole-2-carboxylate hydrochloride (199 mg, 400 μmol), 2-(tert-butoxycarbonylamino)-2-methyl-propanoic acid (85 mg, 420 μmol) and N,N-diisopropylethylamine (348 μL, 2.00 mmol) were added to DMF (20 mL) followed by HBTU (151 mg, 400 μmol) and the reaction stirred overnight. The mixture was quenched with water (10 mL) then acidified with 2M HCl$_{(aq)}$ (5 mL) to afford a solid which was stirred for 10 minutes before being filtered. Purification of the filtered solids by column chromatography (silica, eluting with 100% ethyl acetate), followed by dissolving in methanol (2 mL) and trituration with diethyl ether, filtration and drying under vacuum afforded the desired product as a white solid (205 mg, 75%).

LC-MS (Method B): $R_T$=2.31 min, m/z=683.4 [M+H]$^+$.

| Example | Structure | Name | Analytical Data |
|---|---|---|---|
| Example 63 (free acid) | 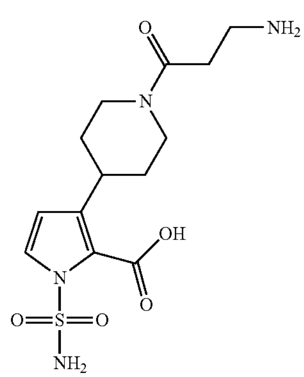 [SMILES: NCCC(=O)N1CCC(c2ccn(S(N)(=O)=O)c2C(=O)O)CC1] | 3-[1-(3-Aminopropanoyl)-4-piperidyl]-1-sulfamoyl-pyrrole-2-carboxylic acid | $^1$H NMR (500 MHz, DMSO-$d_6$) δ = 7.68 (br s, 5H), 7.04-6.98 (m, 1H), 6.01-5.97 (m, 1H), 4.55-4.46 (m, 1H), 3.90-3.79 (m, 1H), 3.65-3.54 (m, 1H), 3.10-2.95 (m, 3H), 2.78-2.68 (m, 2H), 2.62-2.53 (m, 1H), 1.87-1.68 (m, 2H), 1.50-1.30 (m, 2H). LC-MS (Method A): $R_T$ = 1.22 min, m/z = 343.3 [M − H]$^-$. |

Step B: Benzyl 3-[1-(2-amino-2-methyl-propanoyl)-4-piperidyl]-1 (benzyloxycarbonyl sulfamoyl)pyrrole-2-carboxylate hydrochloride Benzyl-1-(benzyloxycarbonylsulfamoyl)-3-[1-[2-(tert-butoxycarbonylamino)-2-methyl-propanoyl]-4-piperidyl]pyrrole-2-carboxylate (200 mg, 292 μmol) was dissolved in 4M HCl in 1,4-dioxane (5 mL) and stirred for 2 hours. The mixture was diluted with diethyl ether to afford a solid which was filtered under nitrogen to afford the desired product as a white solid (89 mg, 52%).

$^1$H NMR (500 MHz, DMSO-$d_6$) δ=8.21 (br s, 3H), 7.52-7.50 (m, 2H), 7.41-7.27 (m, 9H), 6.24-6.11 (d, J=3.9 Hz, 1H), 5.30 (s, 2H), 5.05 (s, 2H), 4.12-4.00 (m, 2H), 3.71-3.62 (m, 2H), 3.15-3.08 (m, 1H), 1.72-1.66 (m, 2H), 1.56 (s, 6H), 1.43-1.31 (m, 2H).

LC-MS (Method B): $R_T$=2.20 min, m/z=583.3 [M+H]$^+$.

Step C: 3-[1-(2-Amino-2-methyl-propanoyl)-4-piperidyl]-1-sulfamoyl-pyrrole-2-carboxylic acid hydrochloride Benzyl-3-[1-(2-amino-2-methyl-propanoyl)-4-piperidyl]-1-(benzyloxycarbonylsulfamoyl)pyrrole-2-carboxylate hydrochloride (89 mg, 143 μmol) was hydrogenated in a similar manner to 3-(6-aminopyridin-3-yl)-1-sulfamoyl-1H-pyrrole-2-carboxylic acid, sodium salt (Step B) to give the desired product as a white solid (32 mg, 53%).

$^1$H NMR (500 MHz, DMSO-$d_6$) δ=8.20 (br s, 3H), 8.09 (br s 2H), 7.37 (d, J=2.8 Hz, 1H), 6.26 (d, J=2.8 Hz, 1H), 4.45-4.21 (br m, 2H), 3.13-2.80 (br s, 3H), 1.88-1.79 (m, 2H), 1.60 (s, 6H), 1.51-1.39 (m, 2H).

LC-MS (Method B): $R_T$=0.32 min, m/z=357.3 [M−H]$^−$.

Further Examples

The following examples were prepared in a similar manner to 3-[1-(2-amino-2-methyl-propanoyl)-4-piperidyl]-1-sulfamoyl-pyrrole-2-carboxylic acid hydrochloride starting from benzyl 1-(benzyloxycarbonylsulfamoyl)-3-(4-piperidyl)pyrrole-2-carboxylate hydrochloride.

| Example | Structure | Name | Analytical Data |
|---|---|---|---|
| Example 65 (hydrochloride salt) | 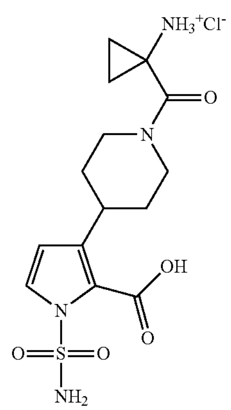 | 3-[1-(1-Aminocyclopropanecarbonyl)-4-piperidyl]-1-sulfamoyl-pyrrole-2-carboxylic acid hydrochloride | $^1$H NMR (500 MHz, DMSO-$d_6$) δ = 8.10 (br s, 2H), 7.29 (d, J = 2.8 Hz, 1H), 6.20 (d, J = 2.8 Hz, 1H), 4.41-4.35 (m, 2H), 3.50-3.40 (m, 2H), 3.00-2.79 (m, 3H), 1.80-1.70 (m, 2H), 1.59-1.42 (m, 2H), 0.98 (br s, 2H), 0.88 (br s, 2H). LC-MS (Method B): $R_T$ = 0.35 min, m/z = 357.2 [M + H]$^+$. Preparative HPLC (Method A, 0.80-1.00 min). |
| Example 66 (hydrochloride salt) | 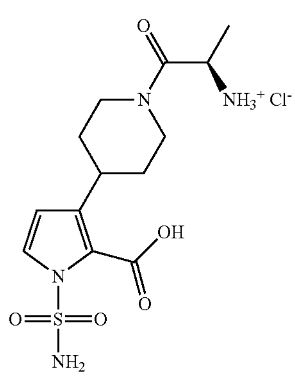 | 3-[1-[(2R)-2-Aminopropanoyl]-4-piperidyl]-1-sulfamoyl-pyrrole-2-carboxylic acid hydrochloride | $^1$H NMR (500 MHz, DMSO-$d_6$) δ = 8.11 (br s, 3H), 8.02 (s, 1H), 7.39 (d, J = 2.8 Hz, 1H), 6.30 and 6.20 (s, J = 2.8 Hz, 1H), 4.52-4.31 (m, 2H), 3.99-3.90 (m, 2H), 3.20-3.08 (m, 1H), 2.74-2.64 (m, 1H), 1.87-1.75 (m, 2H), 1.62-1.38 (m, 2H), 1.38-1.28 (s, 3H). Rotamers coalesce in elevated temperature NMR. LC-MS (Method B): $R_T$ = 0.38 min, m/z = 345.2 [M + H]$^+$. |

| Example | Structure | Name | Analytical Data |
| --- | --- | --- | --- |
| Example 67* (free acid) | 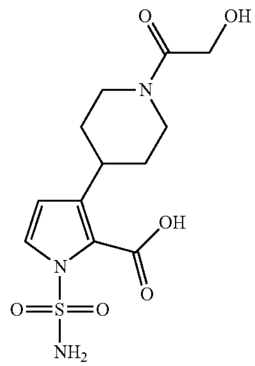 [SMILES: NS(=O)(=O)n1ccc(C2CCN(C(=O)CO)CC2)c1C(=O)O] | 3-[1-(2-Hydroxyacetyl)-4-piperidyl]-1-sulfamoyl-pyrrole-2-carboxylic acid | $^1$H NMR (500 MHz, DMSO-$d_6$) δ = 13.25 (br s, 1H), 8.01 (br s, 2H), 7.37 (d, J = 2.7 Hz, 1H), 6.25 (d, J = 2.7 Hz, 1H), 4.46 (br s, 2H), 4.12-4.08 (m, 2H), 3.75 (br d, J = 12.5 Hz, 1H), 3.01 (br t, J = 12.2 Hz, 1H), 2.70-2.58 (m, 2H), 1.73 (br s, 2H), 1.60-1.36 (m, 2H). LCMS (Method A): $R_T$ = 1.86 min, m/z = 330.2 [M − H]$^-$. |
| Example 68* (free acid) | 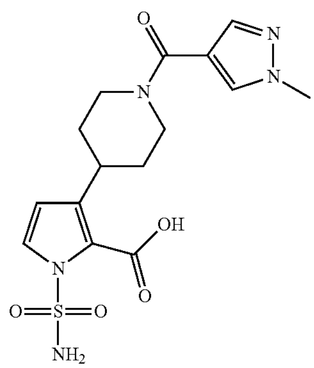 [SMILES: Cn1cc(C(=O)N2CCC(c3ccn(S(N)(=O)=O)c3C(=O)O)CC2)cn1] | 3-[1-(1-Methylpyrazole-4-carbonyl)-4-piperidyl]-1-sulfamoyl-pyrrole-2-carboxylic acid | $^1$H NMR (500 MHz, DMSO-$d_6$) δ = 8.80 (br s, 2H), 8.04 (s, 1H), 7.65 (s, 1H), 7.16 (br s, 1H), 6.14 (br s, 1H), 4.10 (br d, J = 5.5 Hz, 1H), 3.86 (s, 3H), 3.61-3.47 (m, 2H), 3.17 (d, J = 4.6 Hz, 2H), 1.77 (br d, J = 12.4 Hz, 2H), 1.56-1.41 (m, 2H). LC-MS (Method A): $R_T$ = 2.20 min, m/z = 380.3 [M − H]$^-$. |
| Example 69* (free acid) | 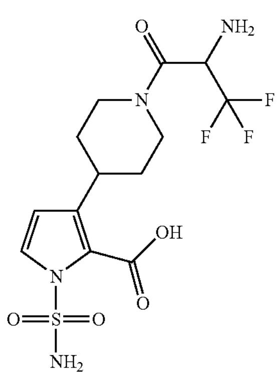 [SMILES: NC(C(=O)N1CCC(c2ccn(S(N)(=O)=O)c2C(=O)O)CC1)C(F)(F)F] | 3-[1-(2-Amino-3,3,3-trifluoro-propanoyl)-4-piperidyl]-1-sulfamoyl-pyrrole-2-carboxylic acid | $^1$H NMR (500 MHz, DMSO-$d_6$) δ = 8.01 (br s, 2H), 7.39 (dd, J = 5.6, 3.1 Hz, 1H), 6.25-6.21 (m, 1H), 4.57-4.49 (m, 1H), 4.21-4.13 (m, 1H), 3.20-3.08 (m, 2H), 1.88-1.73 (m, 2H), 1.51-1.34 (m, 2H), 1.32-1.22 (m, 2H). LC-MS (Method A): $R_T$ = 1.98 min, m/z = 397.3 [M − H]$^-$. |

*Performed using non-Boc protected starting materials following steps A and C only.

Example 70 (free acid): 3-(1-Acetylazetidin-3-yl)-1-sulfamoyl-1H-pyrrole-2-carboxylic acid

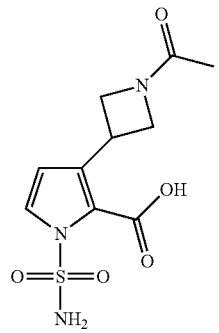 [SMILES: CC(=O)N1CC(c2ccn(S(N)(=O)=O)c2C(=O)O)C1]

Step A: tert-Butyl 3-[2-(benzenesulfonyl)ethenyl]azetidine-1-carboxylate

To a solution of methanesulfonylbenzene (843 mg, 5.40 mmol) in anhydrous THF (15 mL) at −20° C. under argon was added lithium bis(trimethylsilyl)amide (1M solution in THF, 11.3 mL, 11.3 mmol) dropwise and the reaction was allowed to stir for 10 minutes at −20° C. To the reaction mixture was added chlorotimethylsilane (754 μL, 5.94 mmol) and allowed to stir for a further 10 minutes. To the reaction mixture was added a solution of tert-butyl 3-formylazetidine-1-carboxylate (1.00 g, 5.40 mmol) in anhydrous THF (3 mL) dropwise and allowed to stir at −20° C. for a further 3 hours. The reaction mixture was quenched with saturated aqueous ammonium chloride (50 mL) and extracted with ethyl acetate (2×100 mL). The combined organics were washed with water (50 mL), brine (50 mL), dried over MgSO$_4$, filtered and purified by column chromatography (silica, petroleum ether:diethyl ether, gradient elution from 100:0 to 25:75) to give the desired product as a colourless gum (939 mg, 54%).

$^1$H NMR (500 MHz, CDCl$_3$) δ 7.89 (d, J=7.4 Hz, 2H), 7.73-7.54 (m, 3H), 7.12 (dd, J=15.0, 8.0 Hz, 1H), 6.40 (dd, J=15.1, 1.1 Hz, 1H), 4.13 (t, J=8.5 Hz, 2H), 3.80 (dd, J=8.7, 5.6 Hz, 2H), 3.39-3.31 (m, 1H), 1.45 (s, 9H). LC-MS (Method B): R$_T$=3.38 min, m/z=322.3 [M−H]$^-$.

Step B: Benzyl 3-{1-[(tert-butoxy)carbonyl]azetidin-3-yl}-1H-pyrrole-2-carboxylate To a suspension of potassium tert-butoxide (521 mg, 4.65 mmol) in anhydrous THF (10 mL) under argon at 0° C. was added benzyl 2-isocyanoacetate (610 mg, 3.48 mmol) and the reaction was allowed to stir for 10 minutes at 0° C. To the reaction mixture was added a solution of tert-butyl 3-[2-(benzenesulfonyl)ethenyl]azetidine-1-carboxylate (939 mg, 2.90 mmol) in anhydrous THF (10 mL) and allowed to stir and warm to room temperature for 3 hours. The reaction mixture was quenched with saturated aqueous ammonium chloride (50 mL) and extracted with ethyl acetate (2×50 mL). The combined organics were washed with water (50 mL), saturated sodium bicarbonate solution (50 mL), brine (50 mL), dried over MgSO$_4$, filtered and purified by column chromatography (silica, petroleum ether:ethyl acetate, gradient elution from 100:0 to 75:25) to give the desired product as a colourless gum (420 mg, 41%).

$^1$H NMR (500 MHz, CDCl$_3$) δ 9.03 (br s, 1H), 7.41-7.33 (m, 5H), 6.90 (t, J=2.8 Hz, 1H), 6.34 (t, J=2.7 Hz, 1H), 5.26 (s, 2H), 4.27-4.20 (m, 3H), 3.90 (br s, 2H), 1.44 (s, 9H). LC-MS (Method A): R$_T$=3.77 min, m/z=355.3 [M−H]$^-$.

Step C: Benzyl 3-(1-acetylazetidin-3-yl)-1H-pyrrole-2-carboxylate

To a solution of benzyl 3-{1-[(tert-butoxy)carbonyl]azetidin-3-yl}-1H-pyrrole-2-carboxylate (210 mg, 589 μmol) in DCM (5 mL) was added 4M HCl in 1,4-dioxane (1.0 mL, 4.0 mmol) and the reaction was stirred at 20° C. for 5 hours. The reaction mixture was concentrated to dryness, redissolved in methanol and concentrated again, then slurried in diethyl ether and concentrated. The residue was dissolved in DCM (10 mL), cooled to 0° C. followed by the addition of triethylamine (247 μL, 1.77 mmol) and acetyl chloride (54 μL, 886 μmol) and warmed to room temperature stirring for 20 hours. The reaction mixture was diluted with DCM (20 mL), washed with water (20 mL) and brine (20 mL). The organic phase was dried over MgSO$_4$, filtered, concentrated to dryness and purified by column chromatography (silica, petroleum ether:ethyl acetate, gradient elution from 100:0 to 0:100) to give the desired product as a white solid (76 mg, 43%).

$^1$H NMR (500 MHz, CDCl$_3$) δ 9.14 (brs, 1H), 7.41-7.28 (m, 5H), 6.92 (t, J=2.9 Hz, 1H), 6.31 (t, J=2.6 Hz, 1H), 5.33-5.24 (m, 2H), 4.42-4.25 (m, 3H), 4.17-3.95 (m, 2H), 1.85 (s, 3H).
LC-MS (Method A): R$_T$=2.76 min, m/z=297.3 [M−H]$^-$.

Step D: Benzyl 3-(1-acetylazetidin-3-yl)-1-({[(benzyloxy)carbonyl]amino}sulfonyl)-1H-pyrrole-2-carboxylate To a solution of benzyl 3-(1-acetylazetidin-3-yl)-1H-pyrrole-2-carboxylate (76 mg, 255 μmol) in anhydrous THF (4 mL) under argon at −10° C. was added sodium hydride (60% in mineral oil, 31 mg, 764 μmol) portionwise and the reaction was allowed to stir for 45 minutes. To the reaction mixture was added benzyl N-chlorosulfonylcarbamate (70 mg, 280 μmol) and stirred at −10° C. and allowed to warm to room temperature for 18 hours. The reaction mixture was quenched with saturated aqueous ammonium chloride (30 mL), extracted with ethyl acetate (2×30 mL) and the combined organics were washed with brine (30 mL), dried over MgSO$_4$, filtered, concentrated to dryness and purified by column chromatography (silica, DCM:methanol, gradient elution from 100:0 to 95:5), then column chromatography (silica, ethyl acetate:methanol, gradient elution from 100:0 to 92:8) to give the desired product as a white solid (27 mg, 21%).

$^1$H NMR (500 MHz, CD$_3$OD) δ 7.51 (d, J=3.1 Hz, 1H), 7.46 (br d, J=7.0 Hz, 2H), 7.40-7.18 (m, 9H), 6.22 (d, J=3.1 Hz, 1H), 5.43-5.23 (m, 2H), 5.01-4.92 (m, 2H), 4.29-4.10 (m, 2H), 4.07-3.97 (m, 2H), 3.87 (br dd, J=9.3, 5.8 Hz, 1H), 1.78 (s, 3H).
LC-MS (Method A): R$_T$=3.10 min, m/z=512.2 [M+H]$^+$.

Step E: 3-(1-Acetylazetidin-3-yl)-1-sulfamoyl-1H-pyrrole-2-carboxylic acid

Benzyl 3-(1-acetylazetidin-3-yl)-1-({[(benzyloxy)carbonyl]amino}sulfonyl)-1H-pyrrole-2-carboxylate (27 mg, 53 μmol) was hydrogenated in a similar manner to 3-(6-aminopyridin-3-yl)-1-sulfamoyl-1H-pyrrole-2-carboxylic acid, sodium salt (Step B) to give the desired product as a pale beige solid (15 mg, 94%).

$^1$H NMR (500 MHz, CD$_3$OD) δ 7.15 (br d, J=2.9 Hz, 1H), 6.18 (br d, J=2.9 Hz, 1H) 4.51-4.33 (m, 1H), 4.30 (br t, J=6.6 Hz, 1H), 4.20 (br t, J=9.2 Hz, 1H), 4.00 (br t, J=7.2 Hz, 1H), 3.90-3.74 (m, 1H), 1.77 (s, 3H).

LC-MS (Method A): R$_T$=1.76 min, m/z=286.2 [M−H]$^−$.

Example 71 (sodium salt): 3-(2-Pyridyl)-1-sulfamoyl-pyrrole-2-carboxylic acid, sodium salt

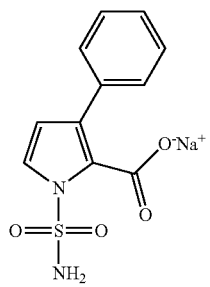

Step A: Benzyl 3-(2-pyridyl)-1H-pyrrole-2-carboxylate

Silver carbonate (567 mg, 2.06 mmol) was added to a degassed solution of 2-ethynylpyridine (0.42 mL, 4.11 mmol) in anhydrous 1,4-dioxane (15 mL) and the reaction mixture heated to 100° C. under nitrogen. A solution of benzyl 2-isocyanoacetate (864 mg, 4.93 mmoL) in anhydrous 1,4-dioxane (2.5 mL) was added dropwise over 30 minutes and the reaction mixture heated for a further 20 hours. The reaction mixture was allowed to cool to room temperature, filtered through a pad of Celite®, and the filter pad was washed alternately with diethyl ether (4×50 mL) and water (3×20 mL). The resulting layers were separated, and the organic layer dried over Na$_2$SO$_4$, filtered and concentrated under reduced pressure. The residue was purified by column chromatography (silica, petroleum ether: ethyl acetate, gradient elution from 80:20 to 40:60) to give the desired product as a colourless oil (746 mg, 65%).

$^1$H NMR (500 MHz, DMSO-d$_6$) δ 12.0 (br s, 1H), 8.56-8.54 (m, 1H), 7.79 (br d, J=7.9 Hz, 1H), 7.66 (td, J=7.7, 1.8 Hz, 1H), 7.37-7.35 (m, 4H), 7.35-7.29 (m, 1H), 7.24-7.21 (m, 1H), 7.06 (t, J=2.7 Hz, 1H), 6.50 (t, J=2.7 Hz, 1H), 5.25 (s, 2H).

LC-MS (Method A): R$_T$=2.05 min, m/z=277.3 [M−H]$^−$.

Step B: Benzyl 1-(benzyloxycarbonylsulfamoyl)-3-(2-pyridyl)pyrrole-2-carboxylate, Sodium Salt A solution of benzyl 3-(2-pyridyl)-1H-pyrrole-2-carboxylate (746 mg, 2.68 mmol) in anhydrous THF (2.5 mL) was added dropwise over a period of 10 minutes to a stirred suspension of sodium hydride (60% in mineral oil, 193 mg, 8.0 mmol) in anhydrous THF (4 mL) at −10° C. under nitrogen. Upon complete addition, the reaction mixture was allowed to warm to room temperature, stirred for 40 minutes and re-cooled to −10° C. Benzyl N-chlorosulfonylcarbamate (733 mg, 2.95 mmol) was added portionwise over a period of 5 minutes and, upon complete addition, the reaction mixture was allowed to warm to room temperature and stirred for 2 hours. The reaction mixture was re-cooled to −10° C. and quenched by the dropwise addition of 1:1 water:brine (10 mL). The solution was extracted with ethyl acetate (3×25 mL) and the combined extracts washed with brine (20 mL), dried over MgSO$_4$, filtered and concentrated under reduced pressure. The residue was purified by column chromatography (silica, petroleum ether:ethyl acetate, gradient elution from 80:20 to 0:100) to afford desired product as a white solid (705 mg, 51%).

$^1$H NMR (500 MHz, DMSO-d$_6$) δ 8.43 (br d, J=4.7 Hz, 1H), 7.70 (td, J=7.8, 1.8 Hz, 1H), 7.48 (d, J=7.8 Hz, 1H), 7.43-7.40 (m, 2H), 7.33-7.26 (m, 8H), 7.21 (d, J=3.1 Hz, 1H), 7.17-7.14 (m, 1H), 6.49 (d, J=3.1 Hz, 1H), 5.19 (s, 2H), 4.83 (s, 2H).

LC-MS (Method A): R$_T$=2.93 min, m/z=490.3 [M−H]$^−$.

Step C: 3-(2-Pyridyl)-1-sulfamoyl-pyrrole-2-carboxylic acid, Sodium Salt

Benzyl 1-(benzyloxycarbonylsulfamoyl)-3-(2-pyridyl) pyrrole-2-carboxylate, sodium salt (705 mg, 1.38 mmol) was hydrogenated in a similar manner to 3-(6-aminopyridin-3-yl)-1-sulfamoyl-1H-pyrrole-2-carboxylic acid, sodium salt (Step B) to give the desired product as a yellow solid (373 mg, 75%).

$^1$H NMR (500 MHz, DMSO-d$_6$) δ 8.93 (br s, 2H), 8.50-4.47 (m, 1H), 8.04 (br d, J=7.8 Hz, 1H), 7.63 (td, J=7.8, 1.8 Hz, 1H), 7.13 (ddd, J=7.4, 4.5, 0.8 Hz, 1H), 7.00 (d, J=3.1 Hz, 1H), 6.51 (d, J=3.1 Hz, 1H).

LC-MS (Method A): R$_T$=1.73 min, m/z=266.2 [M−H]$^−$.

Example 72 (Sodium Salt): 3-(Cyclopropylmethoxy)-1-sulfamoyl-pyrrole-2-carboxylic acid, Sodium Salt

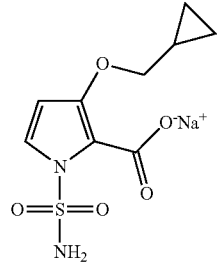

Step A: Methyl 3-(cyclopropylmethoxy)-1H-pyrrole-2-carboxylate (Bromomethyl)cyclopropane (588 mg, 4.36 mmol) was added to a solution of methyl 3-hydroxy-1H-pyrrole-2-carboxylate (615 mg, 4.36 mmol) and potassium carbonate (993 mg, 7.19 mmol) in DMF (5 mL) and the reaction mixture stirred at 90° C. overnight. The reaction mixture was cooled to room temperature and water (100 mL) and diethyl ether (100 mL) were added. The phases were separated and the aqueous phase extracted with diethyl ether (75 mL). The combined organic phases were washed with brine (100 mL), dried over MgSO$_4$ and filtered. The solvent was removed under reduced pressure and purified by column chromatography (silica, petroleum ether:ethyl acetate, gradient elution from 100:0 to 50:50) to give the desired product as a pale yellow oil which solidified upon standing (177 mg, 42%).

$^1$H NMR (500 MHz, CDCl$_3$) δ 8.58 (s, 1H), 6.75 (t, J=3.0 Hz, 1H), 5.91 (t, J=3.0 Hz, 1H), 3.86 (m, 5H), 1.31 (m, 1H), 0.64-0.60 (m, 2H), 0.38-0.35 (m, 2H).

LC-MS (Method B): RT=2.61 min, m/z=194.3 [M–H]$^-$.

Step B: Benzyl 3-(cyclopropylmethoxy)-1H-pyrrole-2-carboxylate

Di-n-butyltin oxide (40 mg, 161 µmol) was added to a solution of methyl 3-(cyclopropylmethoxy)-1H-pyrrole-2-carboxylate (314 mg, 1.61 mmol) in benzyl alcohol (1.7 mL, 16.1 mmol) and the mixture was stirred at 140° C. overnight. The benzyl alcohol was removed by vacuum distillation to afford a brown solid residue. Purification by column chromatography (silica, petroleum ether:ethyl acetate, gradient elution from 100:0 to 50:50) followed by dissolving in a minimum volume of DCM, precipitating with petroleum ether, filtering and drying under vacuum gave the desired product as a white solid (310 mg, 71%).

$^1$H NMR (500 MHz, CDCl$_3$) δ 8.56 (s, 1H), 7.51-7.47 (m, 2H), 7.39-7.33 (m, 2H), 7.33-7.26 (m, 1H), 6.75 (t, J=3.0 Hz, 1H), 5.90 (t, J=3.0 Hz, 1H), 5.33 (s, 2H), 3.86 (d, J=7.0 Hz, 2H), 1.37-1.23 (m, 1H), 0.63-0.59 (m, 2H), 0.37-0.34 (m, 2H).

LC-MS (Method B): R$_T$=3.54 min, m/z=270.3 [M–H]$^-$.

Step C: Benzyl 1-(benzyloxycarbonylsulfamoyl)-3-(cyclopropylmethoxy)pyrrole-2-carboxylate, sodium salt A stirred suspension of sodium hydride (60% in mineral oil, 138 mg, 3.45 mmol) in anhydrous THF (10 mL) was cooled to −10° C. under a nitrogen atmosphere. A solution of benzyl 3-(cyclopropylmethoxy)-1H-pyrrole-2-carboxylate (312 mg, 1.15 mmol) in anhydrous THF (5 mL) was added dropwise over a period of 30 minutes ensuring that the temperature was maintained below −5° C. The reaction mixture was allowed to warm to room temperature and stirred for 1 hour before re-cooling to −10° C. Benzyl N-chlorosulfonylcarbamate (315 mg, 1.26 mmol) was added to the reaction mixture ensuring that the temperature was maintained below −5° C., then allowed to warm to room temperature and stirred for 1 hour. The reaction mixture was re-cooled to −10° C., quenched by the dropwise addition of 50:50 water:brine (100 mL) and extracted with ethyl acetate (3×50 mL). The combined organic phases were washed with brine (100 mL), dried over MgSO$_4$ and the solvent removed under reduced pressure. Purification by column chromatography (silica, petroleum ether:ethyl acetate, gradient elution from 100:0 to 0:100) and trituration with petroleum ether gave the desired product as a white solid (70 mg, 12%).

$^1$H NMR (500 MHz, CD$_3$OD) δ 7.35-7.32 (m, 3H), 7.17 (m, 2H), 7.13-7.07 (m, 6H), 5.88 (d, J=3.5 Hz, 1H), 5.12 (s, 2H), 4.84 (s, 2H), 3.68 (d, J=7.0 Hz, 2H), 1.05 (m, 1H), 0.43-0.40 (m, 2H), 0.17-0.14 (m, 2H).

LC-MS (Method B): R$_T$=2.42 min, m/z=483.3 [M–H]$^-$.

Step D: 3-(Cyclopropylmethoxy)-1-sulfamoyl-pyrrole-2-carboxylic acid, sodium salt Benzyl 1-(benzyloxycarbonylsulfamoyl)-3-(cyclopropylmethoxy)pyrrole-2-carboxylate, sodium salt (30 mg, 61.9 µmol) was hydrogenated in a similar manner to 3-(6-aminopyridin-3-yl)-1-sulfamoyl-1H-pyrrole-2-carboxylic acid, sodium salt (Step B) to give the desired product as a white solid (6 mg, 34%). $^1$H NMR (500 MHz, CD$_3$OD) δ 7.16 (d, J=2.5 Hz, 1H), 6.07 (d, J=2.5 Hz, 1H), 3.86 (s, 2H), 1.24 (br s, 1H), 0.60-0.52 (m, 2H), 0.36-0.30 (m, 2H).

LC-MS (Method A): R$_T$=2.47 min, m/z=259.3 [M–H]$^-$.

Example 73 (sodium salt):
3-Pyrrol-1-yl-1-sulfamoyl-pyrrole-2-carboxylic acid, Sodium Salt

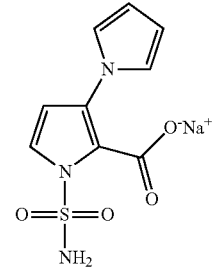

Step A: Ethyl 3-(diallylamino)-1H-pyrrole-2-carboxylate

Allyl bromide (3.72 g, 30.8 mmol) was added to a solution of ethyl 3-amino-1H-pyrrole-2-carboxylate (2.26 g, 14.7 mmol) and potassium carbonate (5.07 g, 36.7 mmol) in anhydrous DMF (10 mL) at room temperature and the reaction mixture allowed to stir for 3 hours. Water (75 mL) was added followed by diethyl ether (100 mL) and the phases separated. The organic phase was dried over MgSO$_4$ and the solvent removed under reduced pressure. Purification by column chromatography (silica, petroleum ether:ethyl acetate, gradient elution from 100:0 to 60:40) gave the desired product as a colourless oil (1.66 g, 48%).

$^1$H NMR (500 MHz, CDCl$_3$) δ 8.59 (br s, 1H), 6.74 (t, J=3.0 Hz, 1H), 5.94-5.86 (m, 3H), 5.19-5.12 (m, 4H), 4.30 (q, J=7.0 Hz, 2H), 3.82 (d, J=6.0 Hz, 4H), 1.34 (t, J=7.0 Hz, 3H).

LC-MS (Method B): R$_T$=3.53 min, m/z=233.4 [M–H]$^-$.

Step B: 1-tert-Butyl 2-ethyl 3-(diallylamino)pyrrole-1,2-dicarboxylate

4-Dimethylaminopyridine (108 mg, 884 µmol) was added to a solution of ethyl 3-(diallylamino)-1H-pyrrole-2-carboxylate (1.04 g, 4.4 mmol) and di-tert-butyl dicarbonate (2.41 g, 11.1 mmol) in DCM (20 mL) at room temperature and the reaction mixture allowed to stir overnight. The reaction mixture was quenched by addition of water (100 mL) and DCM (100 mL) was added. The phases were separated and the aqueous phase extracted with DCM (100 mL). The combined organic phases were dried over MgSO$_4$ and the solvent removed under reduced pressure. Purification by column chromatography (silica, petroleum ether:ethyl acetate, gradient elution from 100:0 to 70:30) gave the desired product as a colourless oil (1.44 g, 97%).

$^1$H NMR (500 MHz, CDCl$_3$) δ 7.12 (d, J=3.5 Hz, 1H), 5.93 (d, J=3.5 Hz, 1H), 5.87-5.80 (m, 2H), 5.16 (m, 1H), 5.14-5.12 (m, 3H), 4.25 (q, J=7.5 Hz, 2H), 3.84 (d, J=6.0 Hz, 4H), 1.55 (s, 9H), 1.31 (t, J=7.5 Hz, 3H).

Step C: 1-tert-Butyl 2-ethyl 3-(2,5-dihydropyrrol-1-yl)pyrrole-1,2-dicarboxylate Hoveyda-Grubbs Catalyst® 2$^{nd}$ generation (30 mg, 47.3 µmol) was added to a solution of 1-tert-butyl 2-ethyl 3-(diallylamino)pyrrole-1,2-dicarboxylate (158 mg, 473 µmol) in DCM (10 mL) and the reaction mixture allowed to stir for 4 hours. The solvent was removed in vacuo and purification by column chromatography (silica, petroleum ether:ethyl acetate, gradient elution from 100:0 to 60:40) gave the desired product as a yellow oil (112 mg, 77%).

$^1$H NMR (500 MHz, CDCl$_3$) δ 7.12 (d, J=3.5 Hz, 1H), 5.84 (m, 2H), 5.79 (d, J=3.5 Hz, 1H), 4.62 (q, J=7.5 Hz, 2H), 4.17 (s, 4H), 1.55 (s, 9H), 1.33 (t, J=7.5 Hz, 3H).

LC-MS (Method B): R$_T$=3.96 min, m/z=207.2 [M+H−Boc]$^+$.

Step D: Ethyl 3-(2,5-dihydropyrrol-1-yl)-1H-pyrrole-2-carboxylate

TFA (2.1 mL, 27.0 mmol) was added to a solution of 1-tert-butyl 2-ethyl 3-(2,5-dihydropyrrol-1-yl)pyrrole-1,2-dicarboxylate (1.3 g, 4.26 mmol) in DCM (10 mL) at room temperature and the reaction mixture allowed to stir for 2 hours. Further TFA (1 mL) was added and the reaction mixture allowed to stir for 1 hour. A saturated aqueous solution of potassium carbonate (30 mL), DCM (75 mL) and water (50 mL) were added. The phases were separated, the organic phase was dried over MgSO$_4$, filtered and the solvent removed under reduced pressure. Purification by column chromatography (silica, petroleum ether:ethyl acetate, gradient elution from 100:0 to 70:30) gave the desired product as a yellow oil (566 mg, 64%).

$^1$H NMR (500 MHz, CDCl$_3$) 58.42 (brs, 1H), 6.75 (t, J=3.0 Hz, 1H), 5.88-5.64 (m, 2H), 5.76 (t, J=3.0 Hz, 1H), 4.30-4.26 (m, 6H), 1.34 (t, J=7.0 Hz, 3H).

Step E: Benzyl 3-pyrrol-1-yl-1H-pyrrole-2-carboxylate

A mixture of ethyl 3-(2,5-dihydropyrrol-1-yl)-1H-pyrrole-2-carboxylate (566 mg, 2.7 mmol), benzyl alcohol (2.97 g, 27.4 mmol) and di-n-butyltin oxide (68 mg, 274 µmol) was heated to 160° C. for 4 days. The solvent was removed in vacuo and purification by column chromatography (silica, petroleum ether:ethyl acetate, gradient elution from 100:0 to 70:30) gave the desired product as a brown oil (135 mg, 18%).

$^1$H NMR (500 MHz, CDCl$_3$) δ 9.01 (brs, 1H), 7.36-7.30 (m, 5H), 7.02 (t, J=2.0 Hz, 2H), 6.88 (t, J=3.0 Hz, 1H), 6.29 (t, J=3.0 Hz, 1H), 6.25 (t, J=2.0 Hz, 2H), 5.27 (s, 2H).

LC-MS (Method B): R$_T$=3.58 min, m/z=265.3 [M−H]$^−$.

Step F: Benzyloxycarbonyl-(2-benzyloxycarbonyl-3-pyrrol-1-yl-pyrrol-1-yl)sulfonyl-azanide, Sodium Salt A suspension of sodium hydride (60% in mineral oil, 61 mg, 1.52 mmol) in anhydrous THF (5 mL) was cooled to −10° C. under a nitrogen atmosphere. A solution of benzyl 3-pyrrol-1-yl-1H-pyrrole-2-carboxylate (135 mg, 507 µmol) in anhydrous THF (5 mL) was added dropwise over a period of 30 minutes ensuring that the temperature was maintained below −5° C. The reaction mixture was allowed to warm to room temperature and stirred for 1 hour before re-cooling to −10° C. Benzyl N-chlorosulfonylcarbamate (139 mg, 558 µmol) was added ensuring that the temperature was maintained below −5° C. The reaction mixture was allowed to warm to room temperature and stirred for 1 hour. The reaction mixture was re-cooled to −10° C. and quenched by the dropwise addition of 50:50 water:brine (100 mL). The aqueous phase was extracted into ethyl acetate (3×50 mL) and the combined organic phases washed with brine (100 mL), dried over MgSO$_4$, filtered and concentrated to dryness under reduced pressure. Purification by column chromatography (silica, petroleum ether:ethyl acetate, gradient elution from 100:0 to 0:100) gave the desired product as a pale brown oil (85 mg, 30%).

$^1$H NMR (500 MHz, DMSO-d$_6$) δ 7.41-7.39 (m, 2H), 7.34-7.27 (m, 9H), 6.92 (t, J=2.0 Hz, 2H), 6.20 (d, J=3.5 Hz, 1H), 6.12 (t, J=2.0 Hz, 2H), 5.14 (s, 2H), 4.87 (s, 2H).

LC-MS (Method B): R$_T$=2.49 min, m/z=478.3 [M−H]$^−$.

Step G: 3-Pyrrol-1-yl-1-sulfamoyl-pyrrole-2-carboxylic acid, sodium salt

Benzyloxycarbonyl-(2-benzyloxycarbonyl-3-pyrrol-1-yl-pyrrol-1-yl)sulfonyl-azanide, sodium salt (85 mg, 177 µmol) was hydrogenated in a similar manner to 3-(6-aminopyridin-3-yl)-1-sulfamoyl-1H-pyrrole-2-carboxylic acid, sodium salt (Step B) to give the desired product as a white solid (20 mg, 32%).

$^1$H NMR (500 MHz, CD$_3$OD) δ 7.17 (d, J=3.0 Hz, 1H), 6.99 (s, 2H), 6.20-6.14 (m, 1H), 6.11 (s, 2H). LC-MS (Method A): R$_T$=2.46 min, m/z=254.2 [M−H]$^−$.

Example 74 (free acid): 4-Ethyl-3-phenyl-1-sulfamoyl-pyrrole-2-carboxylic acid

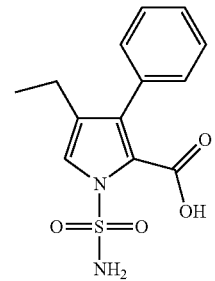 [SMILES: CCc1cn(S(N)(=O)=O)c(C(=O)O)c1-c1ccccc1]

Step A: Benzyl 4-ethyl-3-phenyl-1H-pyrrole-2-carboxylate 1,8-Diazabicyclo[5.4.0]undec-7-ene (1.44 mL, 9.62 mmol) was added dropwise over 5 minutes to a solution of benzyl 2-isocyanoacetate (927 mg, 5.29 mmol) and [2-nitrobut-1-enyl]benzene (8.53 g, 4.81 mmol) in a mixture of THF (7.5 mL) and propan-2-ol (2.5 mL) and the reaction mixture stirred at room temperature for 5 hours. The reaction mixture was concentrated under reduced pressure, the residue taken up in water (50 mL) and extracted with diethyl ether (3×30 mL). The combined organic extracts were washed with brine (50 mL), dried over MgSO$_4$, filtered and concentrated under reduced pressure. The residue was purified by column chromatography (silica, petroleum ether: ethyl acetate, gradient elution from 100:0 to 70:30) to afford the desired product as a pale yellow oil (1.07 g, 73%).

$^1$H NMR (500 MHz, DMSO-d$_6$) δ 11.66 (br s, 1H), 7.35-7.23 (m, 8H), 7.12-7.09 (m, 2H), 6.90 (d, J=3.5 Hz, 1H), 5.11 (s, 2H), 2.28 (q, J=7.5 Hz, 2H), 0.99 (t, J=7.5 Hz, 3H).

LC-MS (Method A): R$_T$=4.09 min, m/z=304.3 [M−H]$^−$.

Step B: Benzyl 1-(benzyloxycarbonylsulfamoyl)-4-ethyl-3-phenyl-pyrrole-2-carboxylate, sodium salt A solution of benzyl 4-ethyl-3-phenyl-1H-pyrrole-2-carboxylate (1.47 g, 4.8 mmol) in anhydrous THF (10 mL) was cooled to −10° C. under a nitrogen atmosphere and sodium hydride (60% in mineral oil, 578 mg, 14.4 mmol) was added portionwise. The reaction mixture was stirred for 5 minutes, allowed to warm to room temperature and stirred for 40 minutes. The reaction mixture was cooled to −10° C., benzyl N-chlorosulfonylcarbamate (1.32 g, 5.30 mmol) added portionwise, stirred for 5 minutes then allowed to warm to room temperature and stirred for a further 30 minutes. The reaction mixture was cooled to −10° C., quenched with the dropwise addition of water (10 mL) and brine (10 mL). The solution was extracted with ethyl acetate (3×20 mL) and the combined organic extracts dried over MgSO$_4$, filtered and concentrated under reduced pressure. The residue was purified by column chromatography (silica, petroleum ether: ethyl acetate:methanol, gradient elution from 95:5:0 to 0:100:0 to 0:80:20) to afford the desired product as a pale yellow solid (349 mg, 13%).

$^1$H NMR (500 MHz, DMSO-d$_6$) δ 7.36-7.29 (m, 8H), 7.25-7.18 (m, 6H), 7.08-7.06 (m, 2H), 5.03 (s, 2H), 5.01 (s, 2H), 2.57 (q, J=7.5 Hz, 2H), 0.96 (t, J=7.5 Hz, 3H).

LC-MS (Method A): R$_T$=4.27 min, m/z=517.3 [M−H]$^-$.

Step C: 4-Ethyl-3-phenyl-1-sulfamoyl-pyrrole-2-carboxylic acid

Benzyl-1-(benzyloxycarbonylsulfamoyl)-4-ethyl-3-phenyl-pyrrole-2-carboxylate, sodium salt (349 mg, 0.64 mmol) was hydrogenated in a similar manner to 3-(6-aminopyridin-3-yl)-1-sulfamoyl-1H-pyrrole-2-carboxylic acid, sodium salt (Step B) to give the desired product as a white solid (161 mg, 84%). $^1$H NMR (500 MHz, DMSO-d$_6$) δ 12.93 (br s, 1H), 8.56 (br s, 2H), 7.37-7.32 (m, 2H), 7.28-7.26 (m, 1H), 7.23-7.22 (m, 2H), 7.10 (br s, 1H), 2.24 (q, J=7.5 Hz, 2H), 0.97 (t, J=7.5 Hz, 3H). LCMS (Method A): R$_T$=3.16 min, m/z=293.3 [M−H]$^-$.

Example 75 (free acid): 4-Methyl-3-phenyl-1-sulfamoyl-1H-pyrrole-2-carboxylic acid

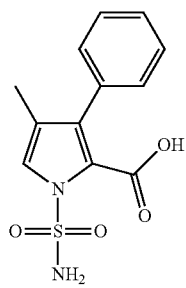 [SMILES: Cc1cn(S(N)(=O)=O)c(C(=O)O)c1-c1ccccc1]

Step A: Benzyl 1-(benzyloxycarbonylsulfamoyl)-4-methyl-3-phenyl-pyrrole-2-carboxylate To a solution of benzyl 4-methyl-3-phenyl-1H-pyrrole-2-carboxylate (500 mg, 1.72 mmol) in anhydrous THF (20 mL) under argon at 0° C. was added sodium hydride (60% in mineral oil, 103 mg, 2.57 mmol) portionwise and allowed to stir for 5 minutes. To the reaction mixture was added [(benzyloxy)carbonyl]({[4-(dimethyliminiumyl)-1,4-dihydropyridin-1-yl]sulfonyl})azanide (633 mg, 1.89 mmol) and heated at 70° C. for 18 hours. The reaction mixture was quenched with saturated ammonium chloride (50 mL) and extracted with ethyl acetate (2×50 mL). The combined organics were washed with water (50 mL), brine (50 mL) dried over MgSO$_4$ and concentrated to dryness under reduced pressure. The crude product was purified via column chromatography (silica, petroleum ether to ethyl acetate) to give the desired product as a beige-yellow solid (120 mg, 14%).

$^1$H NMR (500 MHz, CHLOROFORM-d) δ 7.30-7.40 (m, 11H), 7.10-7.20 (m, 3H) 6.79 (d, J=6.9 Hz, 2H), 5.17 (s, 2H), 5.02 (s, 2H) 1.80-1.90 (m, 3H).

LC-MS (Method A): R$_T$=4.09 min, m/z=505.0 [M+H]$^+$.

Step B: 4-Methyl-3-phenyl-1-sulfamoyl-1H-pyrrole-2-carboxylic acid

To a solution of benzyl 1-(benzyloxycarbonylsulfamoyl)-4-methyl-3-phenyl-pyrrole-2-carboxylate (104 mg, 206 µmol) in methanol (15 mL) was added 10% palladium on carbon (50% wet, 11.0 mg, 103 µmol) and allowed to stir under hydrogen at 20° C. for 6 hours. The reaction mixture was filtered through Celite® and washed with methanol to give a solid. The solid was triturated with pentane and dried to give the desired product as an olive solid (41 mg, 64%).

$^1$H NMR (500 MHz, DMSO-d$_6$) δ 8.25 (br s, 2H), 7.20-7.40 (m, 6H), 1.85 (s, 3H).

LC-MS (Method D): R$_T$=3.96 min, m/z=281.0 [M+H]$^+$.

Example 76 (free tetrazole): 3-(1-Methyl-1H-pyrazol-4-yl)-2-(1H-tetrazol-5-yl)-1H-pyrrole-1-sulfonamide

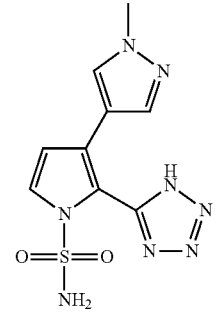 [SMILES: Cn1cc(-c2ccn(S(N)(=O)=O)c2-c2nnn[nH]2)cn1]

Step A: tert-Butyl N-{[3-(1-methyl-1H-pyrazol-4-yl)-2-(1-{[2-(trimethylsilyl)ethoxy]methyl}-1H-tetrazol-5-yl)-1H-pyrrol-1-yl]sulfonyl}carbamate and tert-butyl N-{[3-(1-methyl-1H-pyrazol-4-yl)-2-(2-{[2-(trimethylsilyl)ethoxy]methyl}-2H-tetrazol-5-yl)-1H-pyrrol-1-yl]sulfonyl}carbamate A solution of sodium {[3-bromo-2-(1-{[2-(trimethylsilyl)ethoxy]methyl}-1H-tetrazol-5-yl)-1H-pyrrol-1-yl]sulfonyl}[(tert-butoxy)carbonyl]azanide and sodium {[3-bromo-2-(2-{[2-(trimethylsilyl)ethoxy]methyl}-2H-tetrazol-5-yl)-1H-pyrrol-1-yl]sulfonyl}[(tert-butoxy)carbonyl]azanide (514 mg, 0.94 mmol), 1-methylpyrazole-4-boronic acid pinacol ester (196 mg, 0.95 mmol) and potassium phosphate tribasic (599 mg, 2.8 mmol) in water (3 mL) and 1,4-dioxane (12 mL) was degassed with nitrogen for 5 minutes. To the reaction mixture was added XPhos Pd G2 (148 mg, 0.19 mmol) before heating to 45° C. under microwave irradiation for 2.5 hours. The reaction mixture was diluted with water (20 mL) and ethyl acetate (30 mL) and the resulting layers separated. The aqueous layer was extracted further with ethyl acetate (2×20 mL) and the extracts combined with the original organic layer, washed with 2M HCl$_{(aq)}$ (30 mL), dried over MgSO$_4$, filtered and concentrated under reduced pressure to afford crude product. The crude product was purified by column chromatography (silica, gradient of 10-100% ethyl acetate/petroleum ether then 0-20% methanol/ethyl acetate), triturated with DCM/pentane and dried under reduced pressure to give the desired product mixture as an off-white solid (316 mg, 64%).

LCMS (Method A): R$_T$=3.00 min, m/z=523.3 [M−H]$^−$ and R$_T$=3.48 min, m/z=523.3 [M−H]$^−$.

Step B: 3-(1-Methyl-1H-pyrazol-4-yl)-2-(1H-tetrazol-5-yl)-1H-pyrrole-1-sulfonamide A solution of tert-butyl N-{[3-(1-methyl-1H-pyrazol-4-yl)-2-(1-{[2-(trimethylsilyl)ethoxy]methyl}-1H-tetrazol-5-yl)-1H-pyrrol-1-yl]sulfonyl}carbamate and tert-butyl N-{[3-(1-methyl-1H-pyrazol-4-yl)-2-(2-{[2-(trimethylsilyl)ethoxy]methyl}-2H-tetrazol-5-yl)-1H-pyrrol-1-yl]sulfonyl}carbamate (100 mg, 0.19 mmol) in 5M HCl in propan-2-ol (2 mL) was stirred at room temperature for 17 hours. The reaction mixture was concentrated under reduced pressure to afford a beige solid which was azetroped with methanol (3×5 mL). The resulting solid was triturated with diethyl ether (3×5 mL), the solvent decanted and the remaining solid dried under reduced pressure to afford a beige solid. The solid was purified via preparative HPLC (Method A, 1.0 to 1.11 minutes) to give the desired product as a white solid (27 mg, 46%).

$^1$H NMR (500 MHz, DMSO-d$_6$) δ 8.45 (br s, 2H), 7.57 (br s, 1H), 7.46 (d, J=2.6 Hz, 1H), 7.20 (br s, J=2.1 Hz, 1H), 6.64 (d, J=2.6 Hz, 1H), 3.76 (s, 3H).

LC-MS (Method D): R$_T$=2.67 min, m/z=295.0 [M+H]$^+$.

Further Examples

The following examples were prepared in a similar manner to 3-(1-methyl-1H-pyrazol-4-yl)-2-(1H-tetrazol-5-yl)-1H-pyrrole-1-sulfonamide starting from sodium {[3-bromo-2-(1-{[2-(trimethylsilyl)ethoxy]methyl}-1H-tetrazol-5-yl)-1H-pyrrol-1-yl]sulfonyl}[(tert-butoxy)carbonyl]azanide and sodium {[3-bromo-2-(2-{[2-(trimethylsilyl)ethoxy]methyl}-2H-tetrazol-5-yl)-1H-pyrrol-1-yl]sulfonyl}[(tert-butoxy)carbonyl]azanide or a separated isomer.

| Example | Structure | Name | Analytical Data |
| --- | --- | --- | --- |
| Example 77 (free tetrazole) | 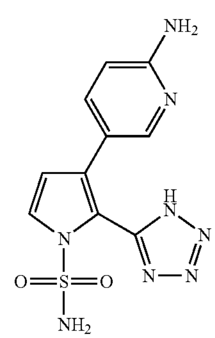 [SMILES: Nc1ccc(-c2ccn(S(N)(=O)=O)c2-c2nnn[nH]2)cn1] | 3-(6-Aminopyridin-3-yl)-2-(1H-tetrazol-5-yl)-1H-pyrrole-1-sulfonamide | $^1$H NMR (500 MHz, DMSO-d$_6$) δ 8.67 (br s, 2H), 8.03 (br s, 2H), 7.82 (br s, 1H), 7.63 (br d, J = 9.1 Hz, 1H), 7.58 (d, J = 3.3 Hz, 1H), 6.90 (br d, J = 9.1 Hz, 1H), 6.74 (d, J = 3.3 Hz, 1H). LC-MS (Method D): R$_T$ = 1.58 min, m/z = 307.0 [M + H]$^+$. |
| Example 78 (free tetrazole) | 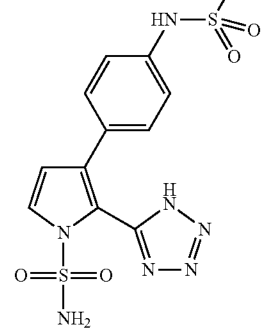 | 3-[4-(Cyclopropylsulfonylamino)phenyl]-2-(1H-tetrazol-5-yl)pyrrole-1-sulfonamide | $^1$H NMR (500 MHz, DMSO-d$_6$) δ 9.77 (s, 1H), 8.48 (br s, 2H), 7.54 (d, J = 3.2 Hz, 1H), 7.14-7.12 (m, 2H), 7.05 (br d, J = 8.5 Hz, 2H), 6.71 (d, J = 3.1 Hz, 1H), 2.64-2.59 (m, 1H), 0.93-0.91 (m, 4H). The multiplet at 2.64-2.59 is partially obscured by residual DMSO peak. LC-MS (Method A): RT = 2.54 min, m/z = 410.1 [M + H]$^+$. Preparative HPLC (Method A, 1.22-1.33 min). |

| Example | Structure | Name | Analytical Data |
|---|---|---|---|
| Example 79 (free tetrazole) | 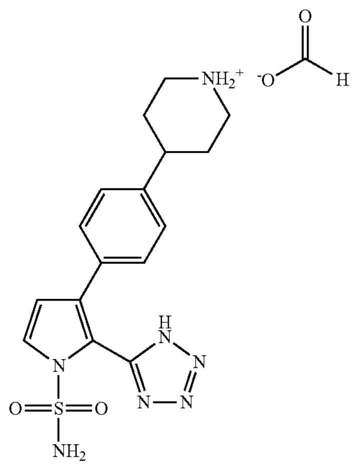 | 3-[4-(4-Piperidyl)phenyl]-2-(1H-tetrazol-5-yl)pyrrole-1-sulfonamide, formate salt | $^1$H NMR (500 MHz, CD$_3$OD) δ 8.45 (s, 1H), 7.30 (d, J = 3.4 Hz, 1H), 7.04-7.02 (m, 2H), 7.00-6.97 (m, 2H), 6.43 (d, J = 3.4 Hz, 1H), 2.74-2.69 (m, 1H), 1.94-1.89 (m, 2H), 1.76-1.68 (m, 2H), 1.24-1.22 (m, 2H), 0.79-0.77 (m, 2H). LC-MS (Method A): R$_T$ = 1.99 min, m/z = 372.3 [M − H]$^−$. Preparative HPLC (Method A, 0.80-1.00 minutes). |

Example 80 (free acid): 1-(4-Fluorophenyl)-3-sulfamoyl-pyrrole-2-carboxylic acid

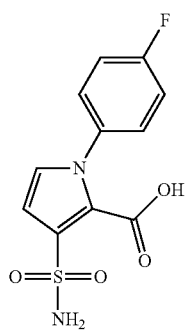 [SMILES: NS(=O)(=O)c1ccn(-c2ccc(F)cc2)c1C(=O)O]

Step A: tert-Butyl 3-(tert-butylsulfamoyl)-1-(4-fluorophenyl)pyrrole-2-carboxylate A mixture of tert-butyl 3-(tert-butylsulfamoyl)-1H-pyrrole-2-carboxylate (100 mg, 0.33 mmol), (4-fluorophenyl)boronic acid (185 mg, 1.32 mmol), copper(II) acetate (90 mg, 0.50 mmol) and pyridine (107 μL, 1.32 mmol) in DCM (1 mL) was stirred at room temperature for 3 days. The reaction mixture was diluted with DCM (3 mL), washed with water (2×3 mL), dried over MgSO$_4$, filtered and concentrated to dryness under reduced pressure. The residue was purified by column chromatography (silica, petroleum ether:ethyl acetate, gradient elution from 100:0 to 70:30) to give the desired product as an off-white solid (100 mg, 76%).

$^1$H NMR (500 MHz, CHLOROFORM-d) δ 7.2-7.3 (m, 2H), 7.1-7.2 (m, 2H), 6.77 (d, J=2.8 Hz, 1H), 6.75 (d, J=2.8 Hz, 1H), 5.99 (s, 1H), 1.27 (s, 9H), 1.23 (s, 9H).

LC-MS (Method A): R$_T$=3.88 min, m/z=419.1 [M+Na]$^+$.

Step B: 1-(4-Fluorophenyl)-3-sulfamoyl-pyrrole-2-carboxylic acid

To a solution of tert-butyl 3-(tert-butylsulfamoyl)-1-(4-fluorophenyl)pyrrole-2-carboxylate (100 mg, 0.25 mmol) in DCM (1 mL) was added trifluoroacetic acid (1 mL) and the resulting solution stirred at room temperature for 5 hours. The mixture was concentrated to dryness under reduced pressure, azeotroped three times with diethyl ether, triturated with diethyl ether (3 mL) and dried at 30° C. under reduced pressure overnight to give the desired product as a white solid (54 mg, 75%).

$^1$H NMR (500 MHz, DMSO-d$_6$) δ 13.50 (br s, 1H), 7.43 (dd, J=4.9, 8.7 Hz, 2H), 7.33 (t, J=8.8 Hz, 2H), 7.20 (d, J=2.5 Hz, 1H), 7.04 (br s, 2H), 6.62 (d, J=2.5 Hz, 1H).

$^{19}$F NMR (471 MHz, DMSO-d$_6$) δ −113.74 (s, 1F).

LC-MS (Method C): R$_T$=4.72 min, m/z=283.1 [M−H]$^−$.

Further Examples

The following examples were prepared in a similar manner to 1-(4-fluorophenyl)-3-sulfamoyl-pyrrole-2-carboxylic acid starting from tert-butyl 3-(tert-butylsulfamoyl)-1H-pyrrole-2-carboxylate.

| Example | Structure | Name | Analytical Data |
|---|---|---|---|
| Example 81 (free acid) | 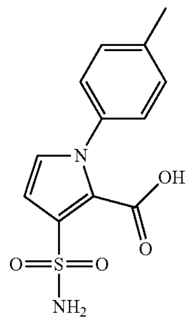 [SMILES: Cc1ccc(-n2ccc(S(N)(=O)=O)c2C(=O)O)cc1] | 1-(p-Tolyl)-3-sulfamoyl-pyrrole-2-carboxylic acid | $^1$H NMR (500 MHz, DMSO-$d_6$) δ 13.42 (br s, 1H), 7.3-7.3 (m, 2H), 7.2-7.3 (m, 2H), 7.14 (d, J = 2.8 Hz, 1H), 7.02 (br s, 2H), 6.60 (d, J = 3.2 Hz, 1H), 2.36 (s, 3H). LC-MS (Method C): $R_T$ = 5.54 min, m/z = 279.1 [M − H]$^-$. |
| Example 82 (sodium salt) | 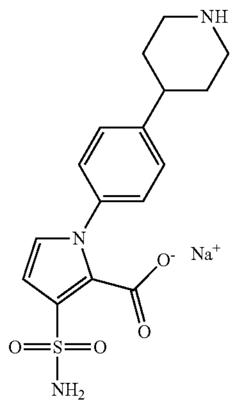 [SMILES: NS(=O)(=O)c1ccn(-c2ccc(C3CCNCC3)cc2)c1C(=O)[O-] ; [Na+]] | 1-[4-(Piperidin-4-yl)phenyl]-3-sulfamoyl-1H-pyrrole-2-carboxylic acid, sodium salt | $^1$H NMR (500 MHz, DMSO-$d_6$) δ 7.19 (s, 4H), 6.57 (br s, 1H), 6.19 (br s, 1H), 3.0-3.1 (m, 2H), 2.5-2.6 (m, 3H), 1.69 (br d, J = 12.3 Hz, 2H), 1.50 (dq, J = 3.9, 12.3 Hz, 2H). LC-MS (Method E): $R_T$ = 1.55 min, m/z = 350.1 [M + H]$^+$. |

Example 83 (free acid): 1-(4-Methoxyphenyl)-3-sulfamoyl-pyrrole-2-carboxylic acid

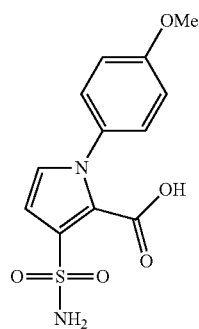 [SMILES: COc1ccc(-n2ccc(S(N)(=O)=O)c2C(=O)O)cc1]

Step A: tert-Butyl 3-(tert-butylsulfamoyl)-1-(4-methoxyphenyl)pyrrole-2-carboxylate A suspension of tert-butyl 3-(tert-butylsulfamoyl)-1H-pyrrole-2-carboxylate (20 mg, 66 µmol), 4-iodoanisole (31 mg, 132 µmol), potassium carbonate (27 mg, 198 µmol), copper(I) iodide (10 mg, 33 µmol) and trans N,N'-dimethylcyclohexane-1,2-diamine (5.6 mg, 40 µmol) in degassed DMF (1 mL) was heated to 100° C. under a nitrogen atmosphere overnight. The reaction mixture was allowed to cool to room temperature, diluted with 50:50 water:brine (10 mL) and extracted into ethyl acetate (3×5 mL). The combined organic phases were washed with 50:50 water:brine (3×5 mL), dried over MgSO$_4$, filtered and concentrated to dryness under reduced pressure.

The reaction was repeated three times and the crude products were combined and purified by column chromatography (silica, petroleum ether:ethyl acetate, gradient elution from 100:0 to 40:60) to give the desired product as a pale orange oil (46 mg total across three reactions, 57%).

$^1$H NMR (500 MHz, CHLOROFORM-d) δ 7.1-7.2 (m, 2H), 6.9-7.0 (m, 2H), 6.75 (d, J=2.8 Hz, 1H), 6.73 (d, J=2.8 Hz, 1H), 6.00 (s, 1H), 3.86 (s, 3H), 1.28 (s, 9H), 1.23 (s, 9H).

LC-MS: $R_T$=3.88 min, m/z=431.0 [M+Na]$^+$.

Step B: 1-(4-Methoxyphenyl)-3-sulfamoyl-pyrrole-2-carboxylic acid

To a solution of tert-butyl 3-(tert-butylsulfamoyl)-1-(4-methoxyphenyl)pyrrole-2-carboxylate (46 mg, 113 µmol) in DCM (1 mL) was added trifluoroacetic acid (1 mL) and the resulting solution stirred at room temperature for 5 hours. The mixture was concentrated to dryness under reduced pressure, azeotroped three times with diethyl ether, triturated with diethyl ether (4 mL) and dried at 30° C. under reduced pressure to give the desired product as a white solid (29 mg, 87%).

$^1$H NMR (500 MHz, DMSO-$d_6$) δ 13.40 (brs, 1H), 7.3-7.3 (m, 2H), 7.13 (d, J=2.8 Hz, 1H), 7.0-7.0 (m, 4H), 6.59 (d, J=2.8 Hz, 1H), 3.80 (s, 3H).

LC-MS (Method C): $R_T$=2.32 min, m/z=295.1 [M−H]$^-$.

Example 84 (free acid):
1-Benzyl-3-sulfamoyl-pyrrole-2-carboxylic acid

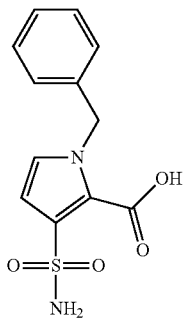 [SMILES: NS(=O)(=O)c1ccn(Cc2ccccc2)c1C(=O)O]

To a solution of tert-butyl 1-benzyl-3-(tert-butylsulfamoyl)pyrrole-2-carboxylate (80 mg, 204 μmol) in DCM (1 mL) was added trifluoroacetic acid (1 mL) and the resulting solution stirred at room temperature for 4 hours. The mixture was concentrated to dryness under reduced pressure, azeotroped three times with diethyl ether, triturated with diethyl ether (4 mL) and dried at 40° C. under reduced pressure to give the desired product as a white solid (35 mg, 61%).

$^1$H NMR (500 MHz, DMSO-$d_6$) δ 13.66 (br s, 1H), 7.3-7.4 (m, 2H), 7.2-7.3 (m, 2H), 7.1-7.1 (m, 2H), 6.86 (br s, 2H), 6.54 (d, J=2.8 Hz, 1H), 5.54 (s, 2H).

LC-MS (Method C): $R_T$=2.13 min, m/z=279.1 [M−H]$^−$.

Example 85 (free acid): 1-(Cyclopropylmethyl)-3-sulfamoyl-pyrrole-2-carboxylic acid

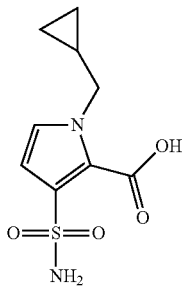 [SMILES: NS(=O)(=O)c1ccn(CC2CC2)c1C(=O)O]

Step A: tert-Butyl 3-(tert-butylsulfamoyl)-1-(cyclopropylmethyl)pyrrole-2-carboxylate A solution of tert-butyl 3-(tert-butylsulfamoyl)-1H-pyrrole-2-carboxylate (100 mg, 331 μmol) in THF (2 mL) was cooled to ° C. and sodium hydride (60% in mineral oil, 16 mg, 400 μmol) was added. After stirring at 0° C. for 5 minutes, (bromomethyl)cyclopropane (47 μL, 496 μmol) was added before allowing the reaction to warm to room temperature and stir overnight. After cooling to 0° C., the reaction mixture was quenched by the dropwise addition of saturated aqueous ammonium chloride (3 mL) and extracted into ethyl acetate (3×3 mL). The combined organic phases were dried over MgSO$_4$, filtered and concentrated to dryness under reduced pressure. The residue was purified by column chromatography (silica, petroleum ether:ethyl acetate, gradient elution from 100:0 to 60:40) to give the desired product as a colourless oil (95 mg, 81%).

$^1$H NMR (500 MHz, CDCl$_3$) δ=6.80 (d, J=2.7 Hz, 1H), 6.65 (d, J=2.7 Hz, 1H), 5.69 (s, 1H), 4.10 (d, J=7.0 Hz, 2H), 1.64 (s, 9H), 1.28-1.24 (m, 1H), 1.23 (s, 9H), 0.64-0.58 (m, 2H), 0.35-0.29 (m, 2H).

LC-MS (Method A): $R_T$=3.88 min, m/z=379.2 [M+Na]$^+$.

Step B: 1-(Cyclopropylmethyl)-3-sulfamoyl-pyrrole-2-carboxylic acid tert-Butyl 3-(tert-butylsulfamoyl)-1-(cyclopropylmethyl)pyrrole-2-carboxylate (95 mg, 267 μmol) in DCM (1 mL) was deprotected in a similar manner to 1-(4-fluorophenyl)-3-sulfamoyl-pyrrole-2-carboxylic acid (Step B) to give the desired product as an off-white solid (36 mg, 55%).

$^1$H NMR (500 MHz, DMSO-$d_6$)=13.68 (br s, 1H), 7.18 (d, J=2.7 Hz, 1H), 6.84 (br s, 2H), 6.48 (d, J=2.7 Hz, 1H), 4.13 (d, J=7.0 Hz, 2H), 1.29-1.19 (m, 1H), 0.52-0.47 (m, 2H), 0.39-0.34 (m, 2H).

LC-MS (Method C): $R_T$=4.83 min, m/z=243.3 [M−H]$^−$.

Biological Data

Compounds of the invention were tested in a metallo-β-lactamase inhibition assay to investigate mechanism of action of the compounds. Results are reported as the concentration of test article required to inhibit enzyme activity by 50% ($IC_{50}$). Compounds exhibited $IC_{50}$ values consistent with potent, specific inhibition of the tested metallo-β-lactamase.

Inhibition of metallo-β-lactamase enzyme function was performed at 37° C. in buffer at pH 7.5 (50 mM HEPES, 150 mM NaCl, 0.1 mM ZnSO4, 20 μg/mL PEG4000), containing 1.5 nM NDM-1, 100 μM nitrocefin, and a range of concentrations of compound. Absorbance at 490 nm was measured using a BMG LABTECH FLUOstar Omega microplate reader every minute for 30 minutes. $IC_{50}$S were determined from the average increase in OD per minute versus the Log 10 concentration of compound using GraphPad Prism. The data is provided in Table 1 below.

TABLE 1

| Example No | NDM-1 $IC_{50}$ (nM) |
| --- | --- |
| 1 | 826.1 |
| 2 | 479.1 |
| 3 | Not tested |
| 4 | Not tested |
| 5 | 444.5 |
| 6 | 2861.0 |
| 7 | Not tested |
| 8 | 448.3 |
| 9 | 1346.8 |
| 10 | Not tested |
| 11 | 4120.5 |
| 12 | Not tested |
| 13 | Not tested |
| 14 | Not tested |
| 15 | Not tested |
| 16 | Not tested |
| 17 | Not tested |
| 18 | 725.1 |
| 19 | 1529.0 |
| 20 | Not tested |
| 21 | 3360.5 |
| 22 | 2089.0 |
| 23 | 548.1 |
| 24 | 608.1 |
| 25 | 1359.0 |
| 26 | 511.8 |
| 27 | Not tested |
| 28 | Not tested |
| 29 | Not tested |
| 30 | Not tested |

TABLE 1-continued

| Example No | NDM-1 IC$_{50}$ (nM) |
|---|---|
| 31 | Not tested |
| 32 | Not tested |
| 33 | Not tested |
| 34 | 150.6 |
| 35 | Not tested |
| 36 | 1012.7 |
| 37 | Not tested |
| 38 | Not tested |
| 39 | Not tested |
| 40 | 264.2 |
| 41 | Not tested |
| 42 | Not tested |
| 43 | Not tested |
| 44 | Not tested |
| 45 | Not tested |
| 46 | 2790 |
| 47 | 655.8 |
| 48 | Not tested |
| 49 | Not tested |
| 50 | Not tested |
| 51 | 262.8 |
| 52 | 2694.0 |
| 53 | 314.3 |
| 54 | Not tested |
| 55 | Not tested |
| 56 | Not tested |
| 57 | Not tested |
| 58 | 1311.9 |
| 59 | Not tested |
| 60 | Not tested |
| 61 | Not tested |
| 62 | 1301.6 |
| 63 | 834.1 |
| 64 | Not tested |
| 65 | Not tested |
| 66 | Not tested |
| 67 | Not tested |
| 68 | Not tested |
| 69 | Not tested |
| 70 | Not tested |
| 71 | Not tested |
| 72 | 3893 |
| 73 | 2573.5 |
| 74 | Not tested |
| 75 | Not tested |
| 76 | 1178.5 |
| 77 | 505.5 |
| 78 | Not tested |
| 79 | Not tested |
| 80 | Not tested |
| 81 | Not tested |
| 82 | Not tested |
| 83 | Not tested |
| 84 | Not tested |
| 85 | Not tested |

MICs were determined by exposing bacteria to serial dilutions of antibacterial agents in MHB-II (cation-adjusted Mueller-Hinton Broth pH 7.4) according to Clinical and Laboratory Standards Institute (CLSI) broth microdilution guidelines (Cockerill et al., 2012).

Combination MIC were performed as described for MIC determinations with the addition of 4 mg/L test article to MHB-II.

Cytotoxicity was evaluated in human Hep G2 cells (ATCC HB-8065) seeded at a density of $2\times10^5$ cells per well and incubated for 24 h at 37° C., 5% $CO_2$. Cells were exposed to a doubling dilution series of test article. After 24 h exposure, the viability of the cells was determined using CellTiter-Glo® (Promega, Wis., USA) according to the manufacturer's instructions. Results are reported as the concentration of test article required to reduce cell viability by 50% ($CC_{50}$).

The following literature references provide additional information on the assay methods used in the assessment of compounds of the invention and the disclosures of these documents in relation to such methods is specifically incorporated herein. For the avoidance of doubt, it is intended that the disclosures of the methods in each of those documents specifically forms part of the teaching and disclosure of this invention. The last two references below provide methodology to establish and demonstrate the existence of synergy and thus the procedures described therein can be used to demonstrate synergistic activity between the compounds of the invention and carbapenems such as meropenem.

COCKERILL, F. R., WICKLER, M. A., ALDER, J., DUDLAY, M. N., ELIOPOULOS, G. M., FERRARO, M. J., HARDY, D. J. ANDHECHT, D. W., HINDLER, J. A., PATEL, J. B., POWEL, M., SWENSON, J. M., THOMPRON, J. B., TRACZEWSKI, M. M., TURNIDGE, J. A., WEINSTEIN, M. P., & ZIMMER, B. L. 2012. Methods for Dilution Antimicrobial Susceptibility Tests for Bacteria that Grow Aerobically (M07-A9). Wayne: Clinical and Laboratory Standards Institute.

PILLAI, S. K., MOELLERING, R. C., & ELIOPOULOS, G. M. 2005. Antimicrobial combinations. In: Antibiotics in Laboratory Medicine. Philadelphia: Lippincott Williams and Wilkins, pp. 365-440.

BURKHART, C. G., BURKHART, C. N., & ISHAM, N. 2006. Synergistic Antimicrobial Activity by Combining an Allylamine with Benzoyl Peroxide with Expanded Coverage against Yeast and Bacterial Species. British Journal of Dermatology 154(2): 341-344.

Biology Data

Compounds of the invention were tested and shown to result in a significant improvement in meropenem activity as presented in the tables below. All of the compounds tested resulted in significant improvement in meropenem activity against a variety of different bacterial strains relative to the baseline study using meropenem only. Some of the compounds tested improved meropenem MICs by more than 10 or 20 times in comparison with meropenem alone. Even the least active compounds of those tested showed activities that improved meropenem MICs by at least 4 times in comparison with meropenem alone. The compounds are effective against a wide range of different bacteria when used in conjunction with meropenem.

The compounds of the invention were tested against a primary panel of bacterial strains, columns I-V of Table 2. As appropriate, compounds considered suitable for further investigation were tested against a secondary panel of bacterial strains, columns VI and VII of Table 2.

TABLE 2

| | Meropenem combination MICs (µg/mL) | | | | | | |
|---|---|---|---|---|---|---|---|
| | I | II | III | IV | V | VI | VII |
| | E. coli | E. coli | K. pneumoniae | A. baumannii | K. pneumoniae | K. pneumoniae | K. pneumoniae |
| | ATCCBAA-2452 | NCTC13476 | ATCC BAA2146 | SG698 | NCTC13440 | NCTC13443 | NCTC13439 |
| Ex No | NDM-1 | IMP | NDM-1 | NDM-1 | VIM-1 | NDM-1 | VIM-1 |
| Meropenem | 1 | 4 | 16 | 8 | 1 | 128 | 0.5 |
| 1 | A | A | B | B | A | D | A |

TABLE 2-continued

| | Meropenem combination MICs (µg/mL) | | | | | | |
|---|---|---|---|---|---|---|---|
| | I | II | III | IV | V | VI | VII |
| | *E. coli* | *E. coli* | *K. pneumoniae* | *A. baumannii* | *K. pneumoniae* | *K. pneumoniae* | *K. pneumoniae* |
| | ATCCBAA-2452 | NCTC13476 | ATCC BAA2146 | SG698 | NCTC13440 | NCTC13443 | NCTC13439 |
| Ex No | NDM-1 | IMP | NDM-1 | NDM-1 | VIM-1 | NDM-1 | VIM-1 |
| 2 | B | A | B | Not tested | A | Not tested | Not tested |
| 3 | A | A | B | Not tested | A | Not tested | Not tested |
| 4 | A | A | C | Not tested | B | E | B |
| 5 | A | A | C | B | B | E | B |
| 6 | A | A | B | C | B | Not tested | Not tested |
| 7 | B | Not tested | Not tested | Not tested | Not tested | Not tested | Not tested |
| 8 | B | A | B | B | A | Not tested | Not tested |
| 9 | B | A | B | B | A | Not tested | Not tested |
| 10 | B | A | C | B | B | Not tested | Not tested |
| 11 | B | A | C | C | A | Not tested | Not tested |
| 12 | B | Not tested | Not tested | Not tested | Not tested | Not tested | Not tested |
| 13 | A | Not tested | Not tested | Not tested | Not tested | Not tested | Not tested |
| 14 | A | A | B | B | A | Not tested | Not tested |
| 15 | A | A | C | C | A | Not tested | Not tested |
| 16 | A | A | C | C | B | Not tested | Not tested |
| 17 | B | B | C | C | B | Not tested | Not tested |
| 18 | A | A | B | B | A | Not tested | Not tested |
| 19 | A | A | B | B | A | Not tested | Not tested |
| 20 | A | Not tested | Not tested | Not tested | Not tested | Not tested | Not tested |
| 21 | A | A | B | B | A | D | A |
| 22 | A | A | B | B | A | Not tested | Not tested |
| 23 | A | A | B | B | B | Not tested | Not tested |
| 24 | A | A | B | E | B | Not tested | Not tested |
| 25 | A | A | B | C | A | Not tested | Not tested |
| 26 | A | A | B | C | A | Not tested | Not tested |
| 27 | A | Not tested | Not tested | Not tested | Not tested | Not tested | Not tested |
| 28 | A | A | B | C | B | Not tested | Not tested |
| 29 | B | A | D | C | B | Not tested | Not tested |
| 30 | B | A | C | D | B | Not tested | Not tested |
| 31 | A | A | B | C | B | Not tested | Not tested |
| 32 | A | Not tested | Not tested | Not tested | Not tested | Not tested | Not tested |
| 33 | A | Not tested | Not tested | Not tested | Not tested | Not tested | Not tested |
| 34 | A | A | B | B | A | E | A |
| 35 | A | A | C | C | B | Not tested | Not tested |
| 36 | A | A | B | B | B | Not tested | Not tested |
| 37 | A | Not tested | Not tested | Not tested | Not tested | Not tested | Not tested |
| 38 | B | Not tested | Not tested | Not tested | Not tested | Not tested | Not tested |
| 39 | B | Not tested | Not tested | Not tested | Not tested | Not tested | Not tested |
| 40 | A | A | C | D | A | Not tested | Not tested |
| 41 | A | A | C | D | A | Not tested | Not tested |
| 42 | A | A | B | C | B | Not tested | Not tested |
| 43 | A | A | B | C | A | Not tested | Not tested |
| 44 | A | Not tested | Not tested | Not tested | Not tested | Not tested | Not tested |
| 45 | A | Not tested | Not tested | Not tested | Not tested | Not tested | Not tested |
| 46 | A | A | C | D | A | Not tested | Not tested |
| 47 | A | A | C | D | A | Not tested | Not tested |
| 48 | B | Not tested | Not tested | Not tested | Not tested | Not tested | Not tested |
| 49 | B | A | D | C | B | Not tested | Not tested |
| 50 | A | A | C | D | B | Not tested | Not tested |
| 51 | A | A | B | C | B | Not tested | Not tested |
| 52 | A | A | C | C | A | D | B |
| 53 | A | A | C | C | A | Not tested | Not tested |
| 54 | B | A | C | C | B | Not tested | Not tested |
| 55 | A | A | Not tested | B | B | Not tested | Not tested |
| 56 | B | A | D | E | B | Not tested | Not tested |
| 57 | B | Not tested | Not tested | Not tested | Not tested | Not tested | Not tested |
| 58 | A | A | B | B | B | Not tested | Not tested |
| 59 | A | A | C | D | B | Not tested | Not tested |
| 60 | B | Not tested | Not tested | Not tested | Not tested | Not tested | Not tested |
| 61 | B | A | C | E | C | Not tested | Not tested |
| 62 | B | A | B | C | A | D | B |
| 63 | A | A | B | C | B | Not tested | Not tested |
| 64 | B | Not tested | Not tested | Not tested | Not tested | Not tested | Not tested |
| 65 | A | Not tested | Not tested | Not tested | Not tested | Not tested | Not tested |
| 66 | A | Not tested | Not tested | Not tested | Not tested | Not tested | Not tested |
| 67 | A | Not tested | Not tested | Not tested | Not tested | Not tested | Not tested |
| 68 | B | A | D | E | B | Not tested | Not tested |
| 69 | B | Not tested | Not tested | Not tested | Not tested | Not tested | Not tested |
| 70 | A | A | B | D | B | Not tested | Not tested |
| 71 | A | A | C | D | B | Not tested | Not tested |
| 72 | A | A | B | D | B | Not tested | Not tested |
| 73 | A | A | B | C | B | Not tested | Not tested |
| 74 | A | B | D | C | B | Not tested | Not tested |

TABLE 2-continued

| | Meropenem combination MICs (μg/mL) | | | | | | |
|---|---|---|---|---|---|---|---|
| | I | II | III | IV | V | VI | VII |
| | E. coli | E. coli | K. pneumoniae | A. baumannii | K. pneumoniae | K. pneumoniae | K. pneumoniae |
| | ATCCBAA-2452 | NCTC13476 | ATCC BAA2146 | SG698 | NCTC13440 | NCTC13443 | NCTC13439 |
| Ex No | NDM-1 | IMP | NDM-1 | NDM-1 | VIM-1 | NDM-1 | VIM-1 |
| 75 | A | A | B | C | B | Not tested | Not tested |
| 76 | A | A | B | B | A | Not tested | Not tested |
| 77 | A | A | B | B | A | C | A |
| 78 | A | Not tested | Not tested | Not tested | Not tested | Not tested | Not tested |
| 79 | A | Not tested | Not tested | Not tested | Not tested | Not tested | Not tested |
| 80 | B | A | C | C | A | Not tested | Not tested |
| 81 | B | A | D | C | B | Not tested | Not tested |
| 82 | B | Not tested | Not tested | Not tested | Not tested | Not tested | Not tested |
| 83 | A | A | C | C | A | Not tested | Not tested |
| 84 | B | Not tested | Not tested | Not tested | Not tested | Not tested | Not tested |
| 85 | B | Not tested | Not tested | Not tested | Not tested | Not tested | Not tested |

Key to Table. The following letters in Table 2 above and Table 3 below represent the MIC (minimum inhibitory concentration) values in μg/ml: A≤01, B≤1, C≤5, D≤10, E≤40 and F≤80.

Compounds of the invention were also tested in combination with imipenem. The results using imipenem as the antibiotic also showed a significant improvement in antibacterial activity as presented in the Table 3 below. All of the compounds tested resulted in significant improvement in imipenem activity against a variety of different bacterial strains relative to the baseline study using imipenem only.

The compounds were tested against the primary panel of bacterial strains, columns I-V as evident from Table 3.

TABLE 3

| | I | II | III | IV | V |
|---|---|---|---|---|---|
| | E. coli | E. coli | K. pneumoniae | A. baumannii | K. pneumoniae |
| | ATCCBAA-2452 | NCTC13476 | ATCC BAA2146 | SG698 | NCTC13440 |
| Compound ID | NDM-1 | IMP | NDM-1 | NDM-1 | VIM-1 |
| Imipenem | D | C | E | F | D |
| AMRC0272 | B | B | B | C | B |
| AMRC0276 | B | B | B | C | B |

Compounds were also tested for cytotoxicity. The data below in Table 4 shows that the tested compounds did not exhibit any significant cytotoxic activity.

TABLE 4

| Cytotoxicity Assay | |
|---|---|
| Example No | HepG2 $CC_{50}$ (μg/mL) |
| 1 | >256 |
| 2 | >128 |
| 3 | >128 |
| 4 | >128 |
| 5 | >256 |
| 6 | >256 |
| 7 | >256 |
| 8 | >256 |
| 9 | >256 |
| 10 | 145.2 |
| 11 | >256 |
| 12 | Not tested |
| 13 | >256 |
| 14 | >256 |
| 15 | >256 |
| 16 | >64 |
| 17 | 251.9 |
| 18 | >256 |
| 19 | >256 |
| 20 | >256 |
| 21 | >256 |
| 22 | >256 |
| 23 | >256 |
| 24 | Not tested |
| 25 | Not tested |
| 26 | Not tested |
| 27 | Not tested |
| 28 | Not tested |
| 29 | Not tested |
| 30 | Not tested |
| 31 | Not tested |
| 32 | Not tested |
| 33 | Not tested |
| 34 | >256 |
| 35 | >256 |
| 36 | >256 |
| 37 | >256 |
| 38 | >256 |
| 39 | Not tested |
| 40 | Not tested |
| 41 | Not tested |
| 42 | Not tested |
| 43 | Not tested |
| 44 | Not tested |
| 45 | Not tested |
| 46 | >256 |
| 47 | Not tested |
| 48 | 158.5 |

TABLE 4-continued

Cytotoxicity Assay

| Example No | HepG2 CC$_{50}$ (µg/mL) |
|---|---|
| 49 | 66.4 |
| 50 | Not tested |
| 51 | Not tested |
| 52 | >256 |
| 53 | Not tested |
| 54 | 247.9 |
| 55 | >256 |
| 56 | Not tested |
| 57 | >256 |
| 58 | >256 |
| 59 | >256 |
| 60 | Not tested |
| 61 | Not tested |
| 62 | >256 |
| 63 | Not tested |
| 64 | Not tested |
| 65 | Not tested |
| 66 | Not tested |
| 67 | Not tested |
| 68 | Not tested |
| 69 | Not tested |
| 70 | Not tested |
| 71 | Not tested |
| 72 | >256 |
| 73 | >256 |
| 74 | 237 |
| 75 | >256 |
| 76 | >256 |
| 77 | >256 |
| 78 | Not tested |
| 79 | Not tested |
| 80 | >256 |
| 81 | >256 |
| 82 | >256 |
| 83 | >256 |
| 84 | >256 |
| 85 | Not tested |

The invention claimed is:

1. A compound of formula (I) or a pharmaceutically acceptable salt, hydrate or solvate thereof:

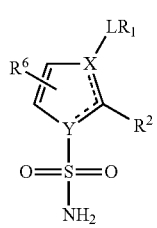

(I)

wherein
one of X and Y is N and the other is C;
L is a linker group selected from —(CH$_2$)$_a$-Q-(CH$_2$)$_b$— in which, Q is selected from the group consisting of: O, NH, SO$_2$, C═C, and C≡C; or Q is absent;
R$^1$ is selected from a ring:

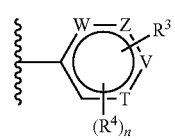

in which: (a) all of T, V, W and Z are C, or (b) T is C and one or two of V, W and Z is N and the remainder of them is/are C, or (c) T is absent, and one of V, W and Z is C and the other two are N; or R$^1$ is a mono- or bicyclic ring substituted by one R$^3$ group and 0, 1, or 2 R$^4$ groups;
R$^2$ is —C(O)OH, —C(O)OM or

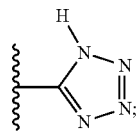

wherein M is a group 1 cation;
R$^3$ is either absent or is selected as appropriate to satisfy valence requirements from the group consisting of: H, halo, CN, oxo, C$_{1-6}$ alkyl, C$_{1-6}$ alkoxy, C$_{2-6}$ alkenyl, C$_{2-6}$ alkynyl, C$_{3-8}$ cycloalkyl, —(CH$_2$)$_d$-aryl, —(CH$_2$)$_d$-heteroaryl, —(CH$_2$)$_e$-heterocyclyl, —OR$^5$, —N(R$^5$)$_2$, —SO$_2$R$^5$, —SO$_2$N(R$^5$)$_2$, —NHSO$_2$R$^7$, —NHCOR$^5$, —CON(R$^5$)$_2$ and —COR$^5$ wherein each of the above substituents apart from H may themselves be optionally substituted where chemically possible with one, two or three groups independently selected at each occurrence from the group consisting of: halo, —N(RS)$_2$, —OH, —C(═O)C$_{1-6}$ alkyl, —SO$_2$N(C$_{1-6}$ alkyl)$_2$, —(CH$_2$)$_h$OR$^5$, C$_{1-6}$ alkyl, C$_{2-6}$ alkenyl, C$_{2-6}$ alkynyl, C$_{3-8}$ cycloalkyl, and C$_{3-8}$ cycloalkenyl;
R$^4$ and R$^5$ are independently selected at each occurrence from the group consisting of: H, halo, —OH, C$_{1-6}$ alkyl, C$_{1-6}$ haloalkyl, C$_{2-6}$ alkenyl, C$_{2-6}$ alkynyl, C$_{3-8}$ cycloalkyl, C$_{3-8}$ cycloalkenyl, —(CH$_2$)$_f$-aryl, —(CH$_2$)$_d$-heteroaryl, and —(CH$_2$)$_g$-heterocyclyl; wherein each of R$^4$ and R$^5$ may themselves be optionally substituted where chemically possible with one, two or three groups independently selected at each occurrence from the group consisting of: halo, —NH$_2$, —N(C$_{1-4}$ alkyl)$_2$, —OH, —SO$_2$N(C$_{1-4}$ alkyl)$_2$, —NHC(═O)OC$_{1-6}$ alkyl, and —C(═O)OC$_{1-6}$ alkyl;
R$^6$ is selected from the group consisting of: H, C$_{1-4}$ alkyl, and C$_{1-4}$ haloalkyl;
R$^7$ is selected from the group consisting of: H, C$_{1-4}$ alkyl, C$_{1-4}$ haloalkyl, C$_{1-4}$ alkyl amine, C$_{3-8}$ cycloalkyl, aryl, and 5 to 10 membered heteroaryl;
a, b, d, e, f, g and h are independently selected as integers from 0 to 3;
and n is an integer selected from: 0 to 2; and
- - - represents a single or a double bond as required to satisfy valence requirements.

2. A compound according to claim 1, wherein Y is N and X is C.

3. A compound according to claim 1, wherein R$^1$ is

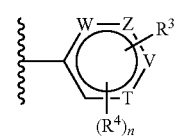

in which: (a) all of T, V, W and Z are C, or (b) T is C and one or two of V, W and Z is N and the remainder of them is/are C, or (c) T is absent, and one of V, W and Z is C and the other two are N; and n is 1 or 2.

4. A compound according to claim 1, wherein $R^2$ is —C(O)OH or —C(O)OM.

5. A compound according to claim 1, wherein $R^2$ is

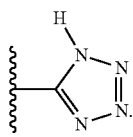

6. A compound as claimed in claim 1, wherein $R^3$ is either absent or is selected as appropriate to satisfy valence requirements from the group consisting of: halo, CN, oxo, $C_{1-6}$ alkyl, $C_{1-6}$ alkoxy, 3 to 10 membered heterocyclyl, —$OR^5$, —$N(R^5)_2$, —$SO_2R^5$, —$SO_2N(R^5)_2$, —$NHSO_2R^7$, and —$COR^5$ wherein each of the above substituents may themselves be optionally substituted where chemically possible with one, two or three groups (preferably 1 or 2 groups) independently selected at each occurrence from the group consisting of: halo, —C(=O)$C_{1-6}$ alkyl or —$SO_2N(C_{1-6}$ alkyl$)_2$.

7. A compound according to claim 1, wherein $R^3$ is substituted or unsubstituted aryl or heterocyclyl.

8. A compound as claimed in claim 1, wherein $R^3$ is selected from: —$NH_2$, methyl, oxo, —$SO_2Me$, —$SO_2N(Me)_2$, and 4-piperidinyl.

9. A compound as claimed claim 1, wherein $R^4$ is selected at each occurrence from the group consisting of: H, halo, substituted or unsubstituted $C_{1-6}$ alkyl, and substituted or unsubstituted $C_{3-8}$ cycloalkyl.

10. A compound as claimed in claim 9, wherein $R^4$ is independently selected at each occurrence from H, fluoro and Me.

11. A compound as claimed in claim 1, wherein $R^5$ is independently selected at each occurrence from the group consisting of: H, —OH, $C_{1-6}$ alkyl, $C_{1-6}$ haloalkyl, 3 to 10 membered heterocyclyl, and $C_{3-8}$ cycloalkyl; wherein each $R^5$ may themselves be optionally substituted where chemically possible with one or two groups independently selected at each occurrence from the group consisting of: —$NH_2$, —OH, —$SO_2N(C_{1-4}$ alkyl$)_2$, —NHC(=O)Otert-butyl and —C(=O)Otert-butyl.

12. A compound as claimed in claim 11, wherein $R^5$ is H.

13. A compound as claimed in claim 1, wherein the compound is selected from:

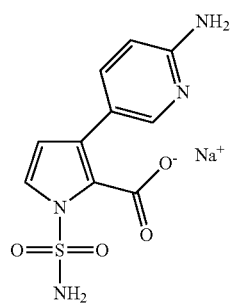
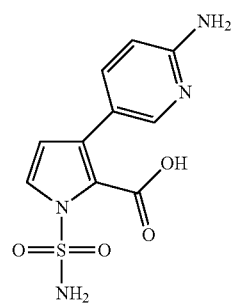

-continued

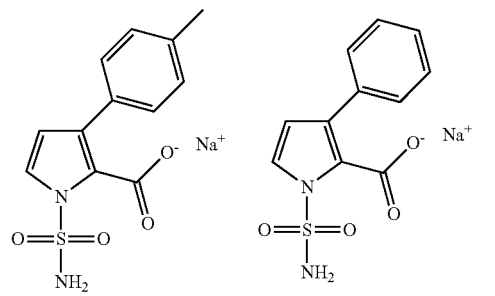
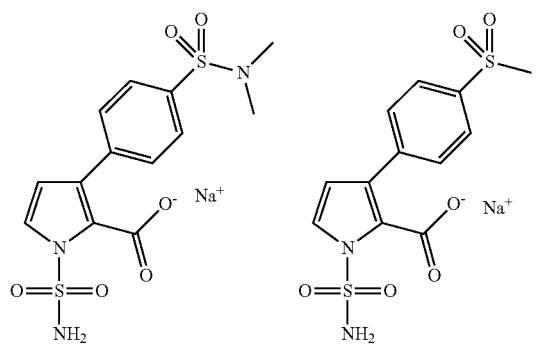
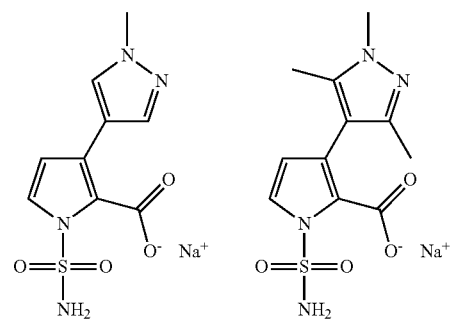
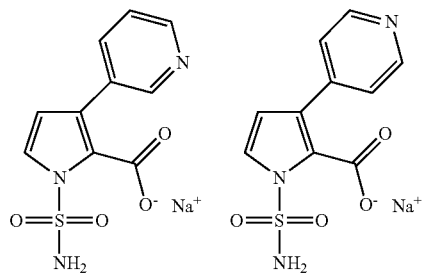
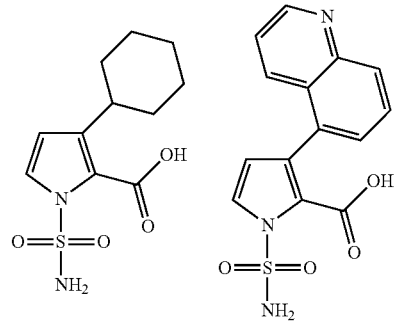

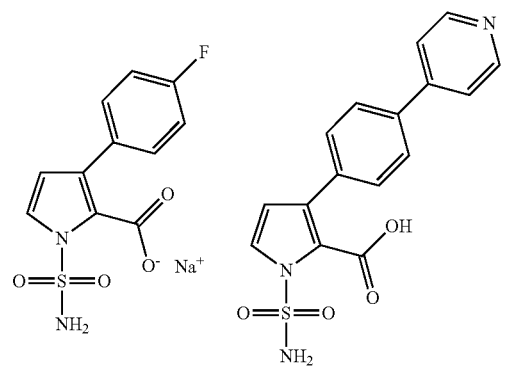
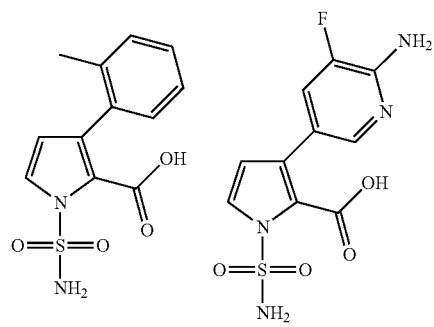
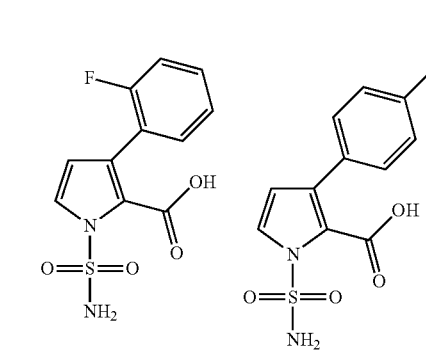
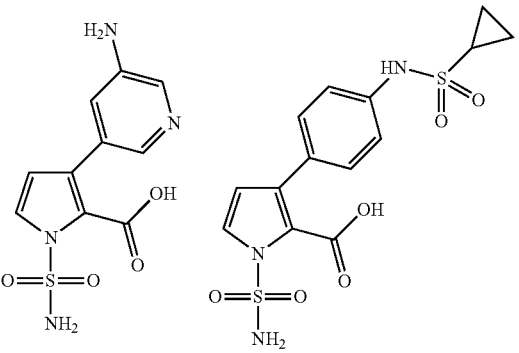
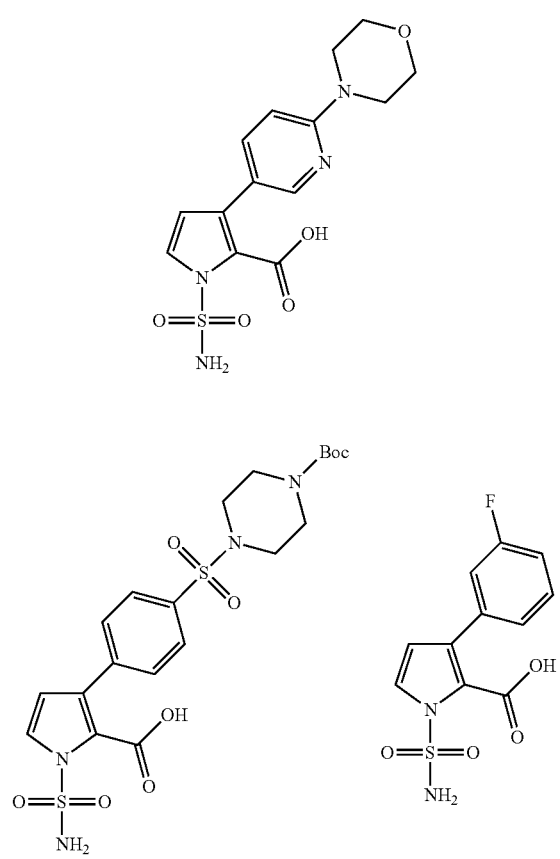
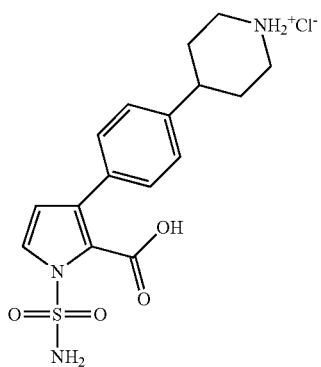
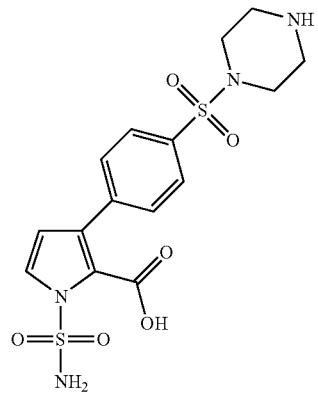

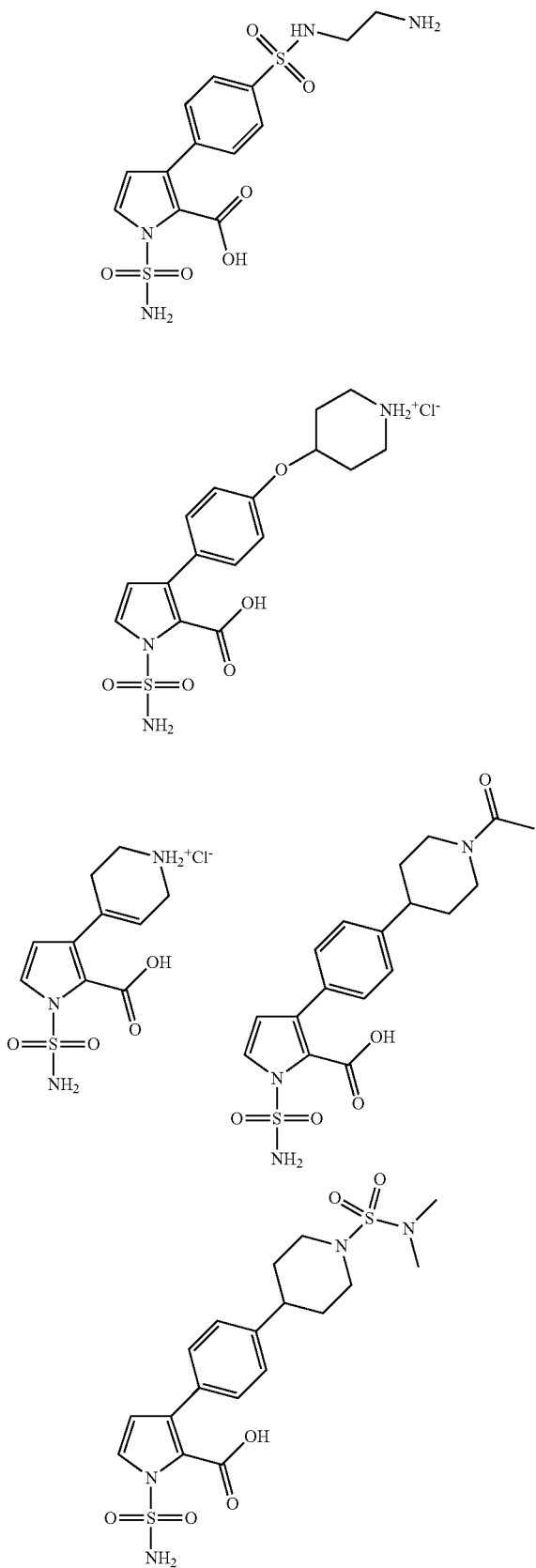
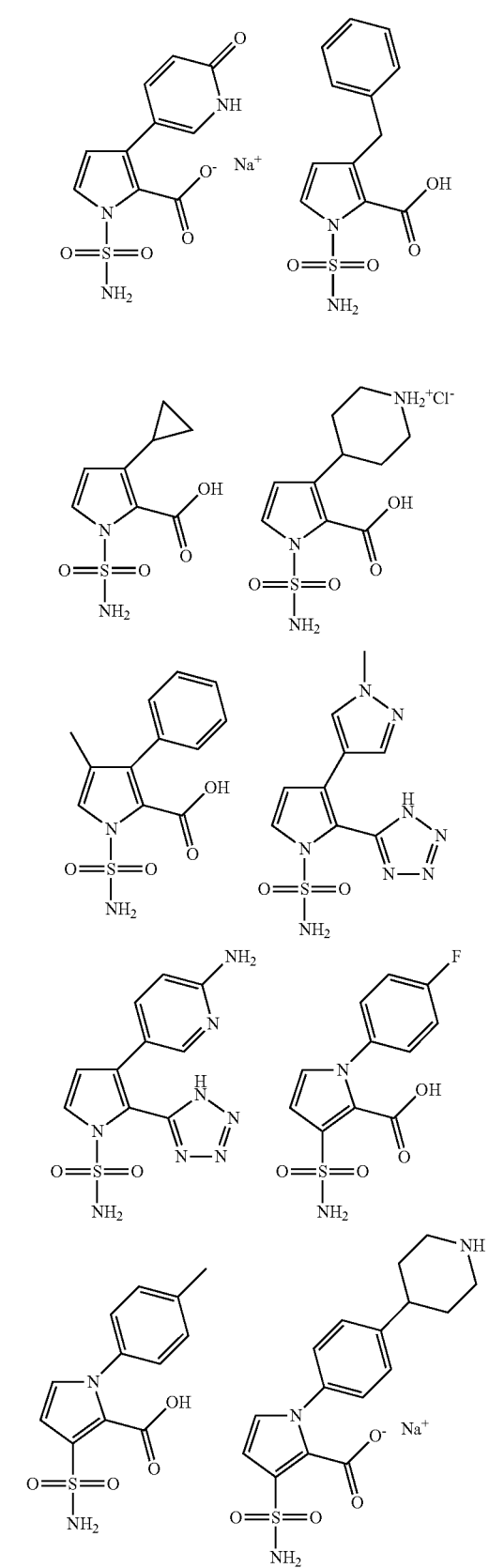

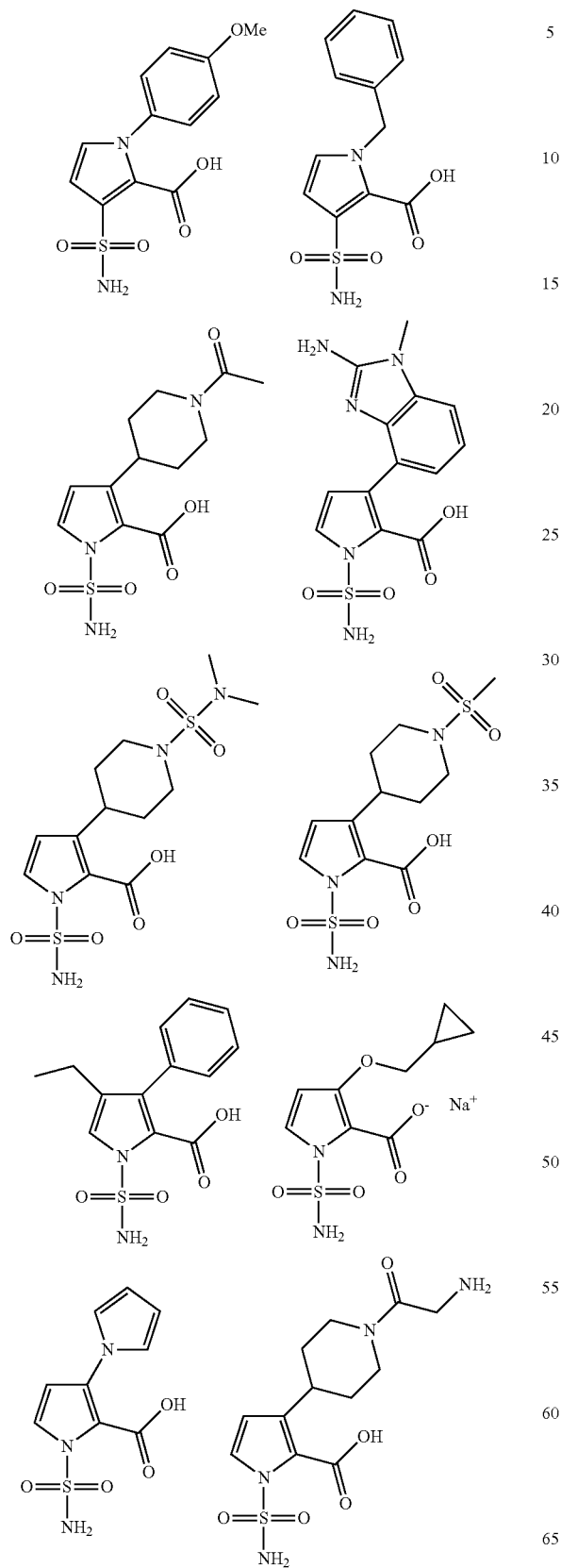
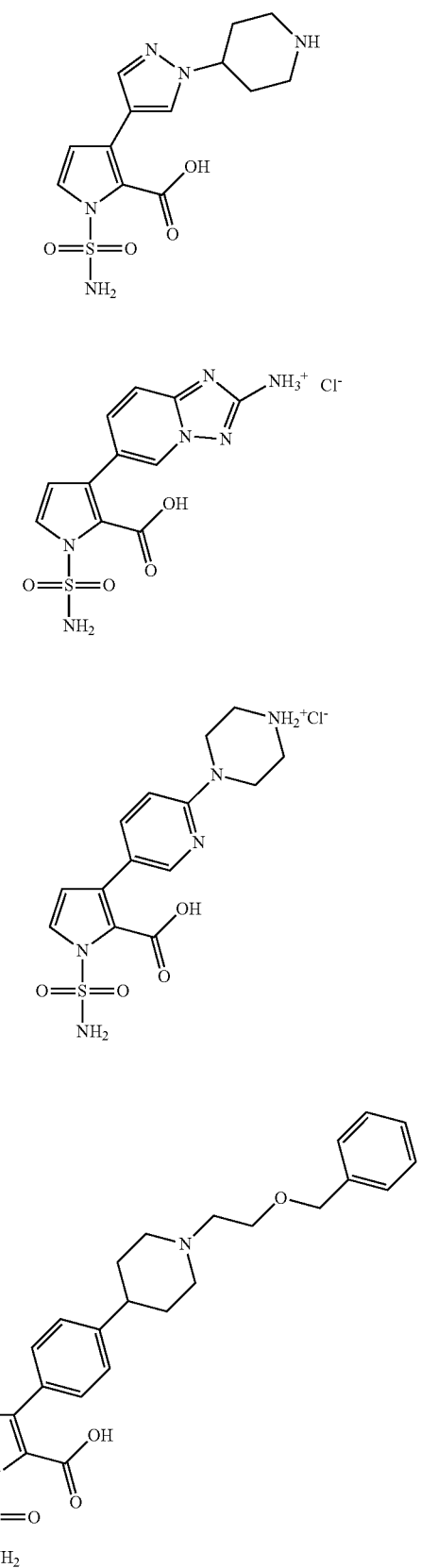

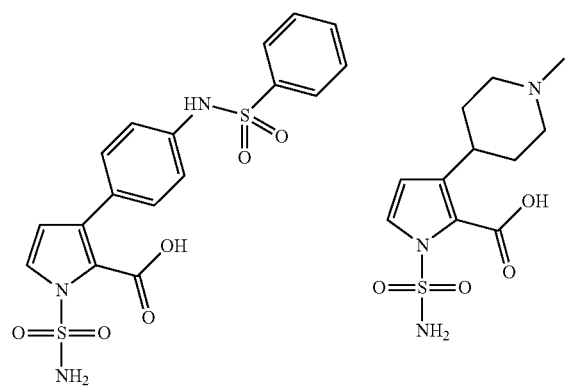
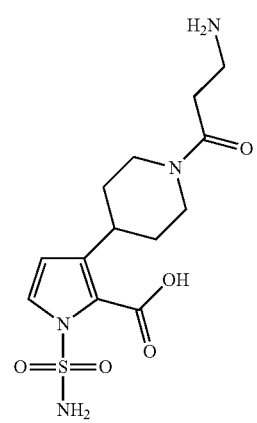
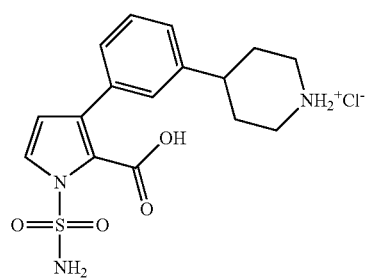
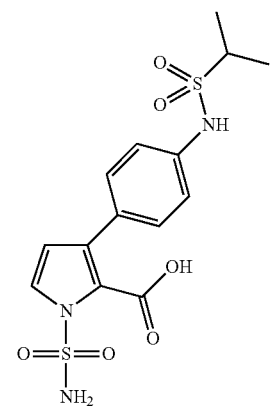
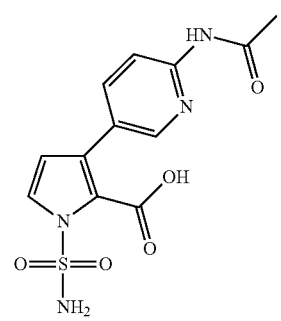
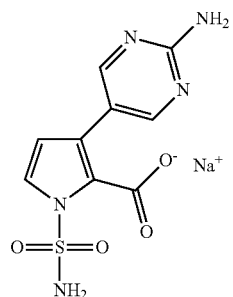
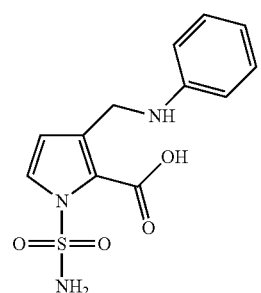
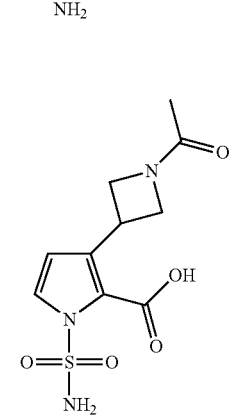
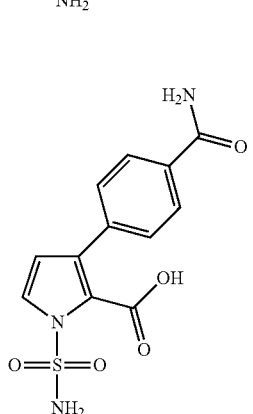
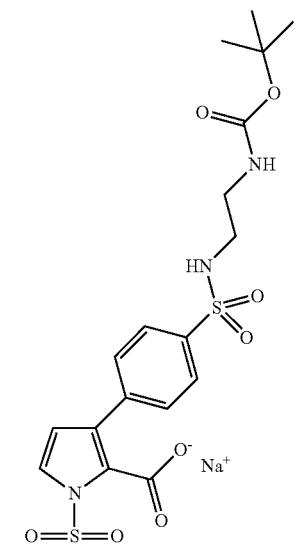
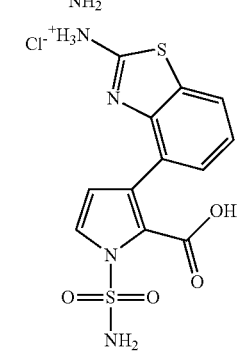

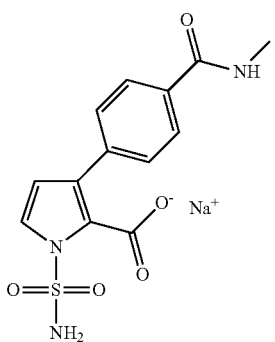
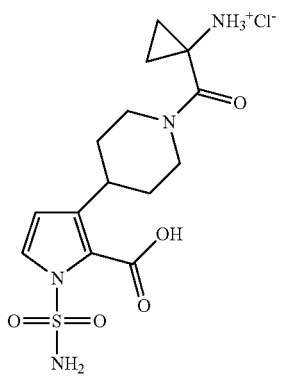
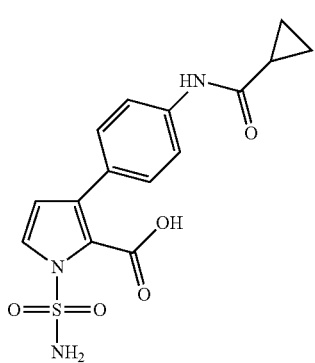
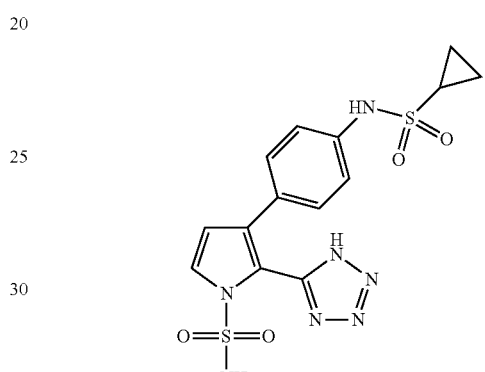
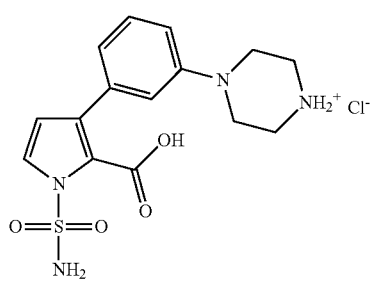
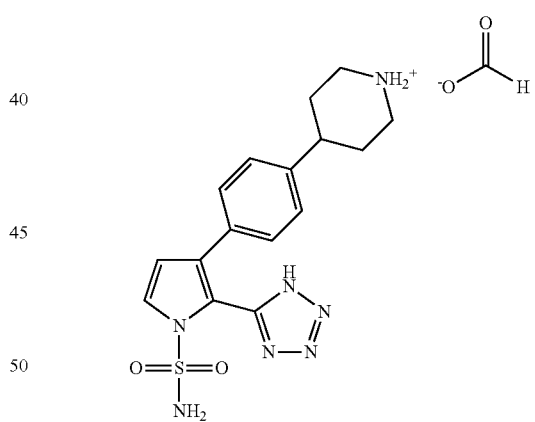
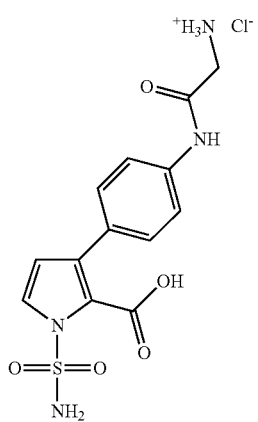
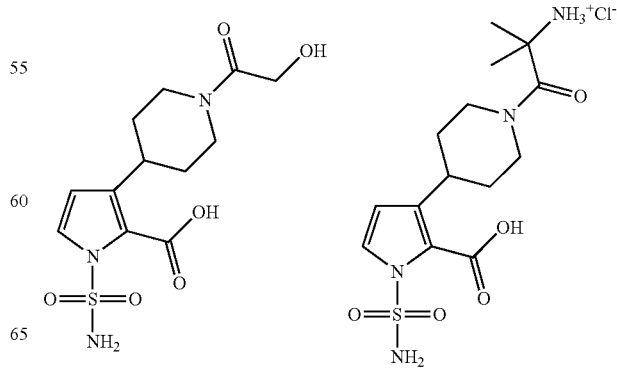

-continued

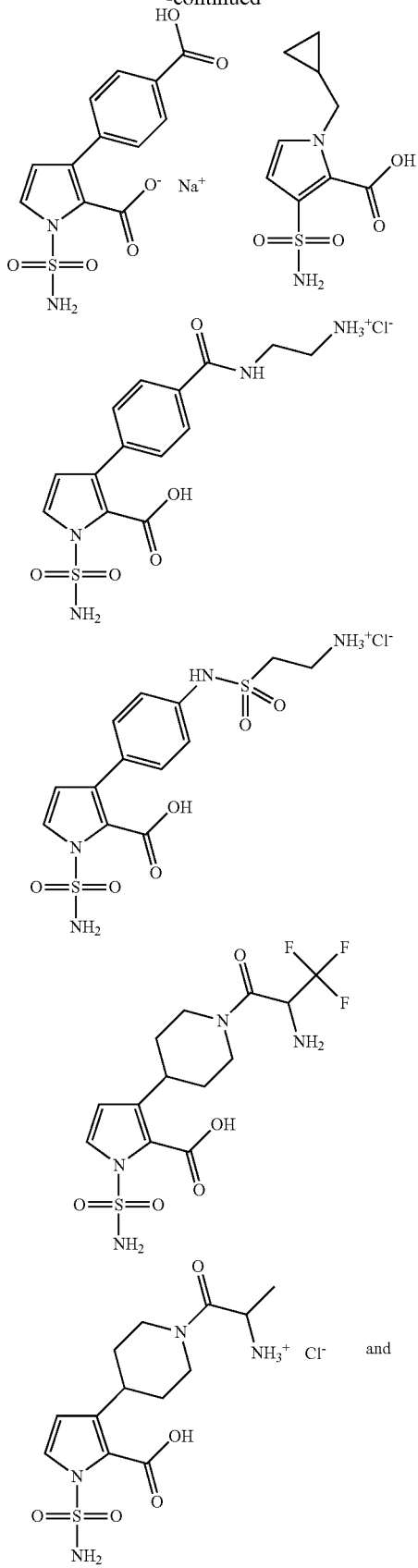

-continued

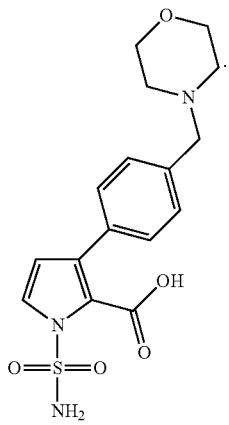 [SMILES: NS(=O)(=O)n1ccc(-c2ccc(CN3CCOCC3)cc2)c1C(=O)O]

14. A pharmaceutical composition which comprises a compound of Formula (I) as claimed in claim 1, or a pharmaceutically acceptable salt, hydrate or solvate thereof, in association with one or more pharmaceutically acceptable excipients.

15. A method for the treatment of a bacterial infection caused by aerobic or anaerobic Gram-positive, or aerobic or anaerobic Gram-negative bacteria, in a patient in need of such treatment, said method comprising administering to said patient a therapeutically effective amount of a combination of an antibacterial agent with a compound of Formula (I) as claimed in claim 1, or a pharmaceutically acceptable salt, hydrate or solvate thereof or administering to said patient a therapeutically effective amount of an antibacterial agent in combination with a pharmaceutical composition, as claimed in claim 14, containing a compound of Formula (I) or a pharmaceutically acceptable salt, hydrate or solvate thereof.

16. The method of claim 15, wherein the bacterial infection is selected from: pneumonia, respiratory tract infections, urinary tract infections, intra-abdominal infections, skin and soft tissue infections, bloodstream infections, septicaemia, intra- and post-partum infections, prosthetic joint infections, endocarditis, acute bacterial meningitis and febrile neutropenia.

17. The method of claim 16, wherein the bacterial infection is selected from: community acquired pneumonia, nosocomial pneumonia, respiratory tract infections associated with cystic fibrosis, non-cystic fibrosis bronchiectasis, COPD, urinary tract infection, intra-abdominal infections, skin and soft tissue infection, bacteraemia, septicaemia, intra- and post-partum infections, prosthetic joint infections, endocarditis, acute bacterial meningitis and febrile neutropenia.

18. The method of claim 17, wherein the bacterial infection is selected from: community acquired pneumonia, nosocomial pneumonia, respiratory tract infections associated with cystic fibrosis, non-cystic fibrosis bronchiectasis, COPD, urinary tract infection, intra-abdominal infections, skin and soft tissue infection, bacteraemia and septicaemia.

\* \* \* \* \*